US008722580B2

(12) United States Patent
Nagasawa et al.

(10) Patent No.: US 8,722,580 B2
(45) Date of Patent: May 13, 2014

(54) AGENT FOR INHIBITING CYTOKININ SIGNALING

(75) Inventors: Asako Nagasawa, Kobe (JP); Yuto Arata, Kobe (JP); Hideki Uneme, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 812 days.

(21) Appl. No.: 12/515,935

(22) PCT Filed: Nov. 22, 2007

(86) PCT No.: PCT/JP2007/073126
§ 371 (c)(1),
(2), (4) Date: May 21, 2009

(87) PCT Pub. No.: WO2008/062907
PCT Pub. Date: May 29, 2008

(65) Prior Publication Data
US 2010/0056377 A1    Mar. 4, 2010

(30) Foreign Application Priority Data

Nov. 22, 2006  (JP) ................................. 2006-315308
Nov. 22, 2006  (JP) ................................. 2206-315309
Feb. 1, 2007   (JP) ................................. 2007-022850
Feb. 1, 2007   (JP) ................................. 2007022849

(51) Int. Cl.
*A01N 43/54*   (2006.01)
*A61K 31/517*  (2006.01)
*C07D 239/72*  (2006.01)
*C07D 401/00*  (2006.01)

(52) U.S. Cl.
USPC ..................... 504/168; 514/266.1; 514/266.2; 544/283; 544/284

(58) Field of Classification Search
USPC ................. 504/168; 544/282, 283; 514/266.1
See application file for complete search history.

(56) References Cited

U.S. PATENT DOCUMENTS

| | | | |
|---|---|---|---|
| 3,509,141 A | | 4/1970 | Walker |
| 4,183,932 A | | 1/1980 | Yamamoto et al. |
| 4,282,361 A | | 8/1981 | Hecht et al. |
| 4,499,092 A | | 2/1985 | Hallot et al. |
| 4,502,880 A | * | 3/1985 | Holyoke ............. 504/168 |
| 5,646,154 A | | 7/1997 | Irie et al. |
| 2002/0177162 A1 | | 11/2002 | Kakimoto et al. |
| 2004/0117871 A1 | | 6/2004 | Meyer et al. |
| 2005/0065166 A1 | | 3/2005 | Gesing et al. |
| 2005/0096327 A1 | | 5/2005 | Caprathe et al. |

FOREIGN PATENT DOCUMENTS

| | | |
|---|---|---|
| JP | 40-20866 B1 | 9/1965 |
| JP | 53-23997 A | 3/1978 |
| WO | WO 02/42440 A2 | 5/2002 |
| WO | WO 03/037878 A1 | 5/2003 |
| WO | WO 2005/021715 A2 | 3/2005 |

OTHER PUBLICATIONS

Kikelj et atl, Product class 13: quinazolines Science of Synthesis (2004), 16, 573-749 CODEN: SSCYJ9; English.*
Hynes et al., Synthesis of 2-aminoquinazolines from ortho-fluoroketones Journal of Heterocyclic Chemistry (1995), 32(4), 1185-7 CODEN: JHTCAD; ISSN: 0022-152X; English.*
Office Action in European Application No. 07832825.9 mailed Sep. 22, 2011.
Karminski et al., "The synthesis of some quinazoline derivatives and their biological properties", Journal of Environmental Science and Health, vol. B18, Nos. 4 & 5, 1983, pp. 599-610.
Russian Office Action for Application No. 2009123470/15 dated Nov. 21, 2011 (with English translation).
Kamal et al., "Synthesis of 5H-Dipyrido[1,2-a:3',2'-e]Pyrimidin-5-One and 5-H-Pyrido-[3',2':5,6]Pyrimido[1,2-a]Quinazolin-5-Ones", Heterocycles, vol. 24, No. 11, 1986, pp. 3075-3078.
Kikelj, "Product Class 13: Quinazolines", Science of Synthesis, Houben-Weyl Methods of Molecular Transformations, Georg Thieme Verlag Stuttgart, New York, vol. 16, 2004, pp. 573-749.
Kwon et al., "Cyclization of Quinazoline Derivatives", Nippon Kagaku Kaishi, No. 10, 1973, pp. 1944-1948.
Schleuder et al., "Antiarrhythmisch wirksame Amidinohydrazone substituierter Benzophenone", Pharmazie, No. 48, H. 1, 1993, pp. 33-37.
Chinese Office Action for Chinese Application No. 200780050202.5 dated Mar. 31, 2012 with English translation.
Australian Office Action for Appl. No. 2007322610 dated Apr. 26, 2012.
EPO Supplementary European Search Report, Application No. EP 07 832 825.9, Nov. 23, 2009, pp. 1-6.

(Continued)

*Primary Examiner* — Paul V. Ward
(74) *Attorney, Agent, or Firm* — Birch, Stewart, Kolasch & Birch, LLP

(57) ABSTRACT

Disclosed are: a substance which has an activity of inhibiting the intracellular signaling from a plant-derived cytokinin receptor and which can control the growth or differentiation of a plant. Also, disclose is a method for searching for a chemical substance capable of promoting the growth of a root of a plant, which comprises measuring the level of intracellular signaling from the receptor in a system where a cell having the receptor is contacted with a chemical substance having an agonistic activity on the receptor and a substance to be tested, comparing the level of intracellular signaling measured in the preceding step with a level of intracellular signaling measured in the absence of the chemical substance, and determining the chemical substance as being a chemical substance capable of promoting the growth of a root of a plant based on the difference obtained by the comparison; and others.

20 Claims, 6 Drawing Sheets

(56) References Cited

OTHER PUBLICATIONS

S. Nishikawa et al, "Synthesis of 4-Mono- and 2, 4-Disubstituted Derivatives of pyrido-[3, 2-d]pyrimidine, pyrido[2, 3-d]pyrimidine and Quinalozine", Bulletin of the Faculty of Agriculture, MIE University, 1985, vol. 71, pp. 89-96.

Chinese Office Action issued in Chinese Application No. 200780050202.5, issued on Feb. 17, 2013, 13 pages.
Canadian Office Action for Canadian Application No. 2,669,275, dated May 24, 2013, 3 pages.
European Office Action for European Application No. 07 832 825.9, dated Jun. 25, 2013, 3 pages.

* cited by examiner

UTC            10ppm
               Ic3-3

SEQUENCE LISTING

<160> NUMBER OF SEQ ID NOS: 8

<210> SEQ ID NO 1
<211> LENGTH: 1057
<212> TYPE: PRT
<213> ORGANISM: Arabidopsis thaliana -continued

```
<400> SEQUENCE: 1

Met Asn Trp Ala Leu Asn Asn His Gln Glu Glu Glu Glu Pro Arg
1               5                   10                  15

Arg Ile Glu Ile Ser Asp Ser Glu Ser Leu Glu Asn Leu Lys Ser Ser
            20                  25                  30

Asp Phe Tyr Gln Leu Gly Gly Gly Ala Leu Asn Ser Ser Glu Lys
        35                  40                  45

Pro Arg Lys Ile Asp Phe Trp Arg Ser Gly Leu Met Gly Phe Ala Lys
50                  55                  60

Met Gln Gln Gln Gln Leu Gln His Ser Val Ala Val Lys Met Asn
65                  70                  75                  80

Asn Asn Asn Asn Asp Leu Met Gly Asn Lys Lys Gly Ser Thr Phe
                85                  90                  95

Ile Gln Glu His Arg Ala Leu Leu Pro Lys Ala Leu Ile Leu Trp Ile
            100                 105                 110

Ile Ile Val Gly Phe Ile Ser Ser Gly Ile Tyr Gln Trp Met Asp Asp
        115                 120                 125

Ala Asn Lys Ile Arg Arg Glu Glu Val Leu Val Ser Met Cys Asp Gln
130                 135                 140

Arg Ala Arg Met Leu Gln Asp Gln Phe Ser Val Ser Val Asn His Val
145                 150                 155                 160

His Ala Leu Ala Ile Leu Val Ser Thr Phe His Tyr His Lys Asn Pro
                165                 170                 175

Ser Ala Ile Asp Gln Glu Thr Phe Ala Glu Tyr Thr Ala Arg Thr Ala
            180                 185                 190

Phe Glu Arg Pro Leu Leu Ser Gly Val Ala Tyr Ala Glu Lys Val Val
        195                 200                 205

Asn Phe Glu Arg Glu Met Phe Glu Arg Gln His Asn Trp Val Ile Lys
210                 215                 220

Thr Met Asp Arg Gly Glu Pro Ser Pro Val Arg Asp Glu Tyr Ala Pro
225                 230                 235                 240

Val Ile Phe Ser Gln Asp Ser Val Ser Tyr Leu Glu Ser Leu Asp Met
                245                 250                 255

Met Ser Gly Glu Glu Asp Arg Glu Asn Ile Leu Arg Ala Arg Glu Thr
            260                 265                 270

Gly Lys Ala Val Leu Thr Ser Pro Phe Arg Leu Leu Glu Thr His His
        275                 280                 285

Leu Gly Val Val Leu Thr Phe Pro Val Tyr Lys Ser Ser Leu Pro Glu
290                 295                 300

Asn Pro Thr Val Glu Glu Arg Ile Ala Ala Thr Ala Gly Tyr Leu Gly
305                 310                 315                 320

Gly Ala Phe Asp Val Glu Ser Leu Val Glu Asn Leu Leu Gly Gln Leu
                325                 330                 335

Ala Gly Asn Gln Ala Ile Val Val His Val Tyr Asp Ile Thr Asn Ala
            340                 345                 350

Ser Asp Pro Leu Val Met Tyr Gly Asn Gln Asp Glu Glu Ala Asp Arg
        355                 360                 365

Ser Leu Ser His Glu Ser Lys Leu Asp Phe Gly Asp Pro Phe Arg Lys
370                 375                 380

His Lys Met Ile Cys Arg Tyr His Gln Lys Ala Pro Ile Pro Leu Asn
385                 390                 395                 400

Val Leu Thr Thr Val Pro Leu Phe Phe Ala Ile Gly Phe Leu Val Gly
                405                 410                 415
```

```
Tyr Ile Leu Tyr Gly Ala Ala Met His Ile Val Lys Val Glu Asp Asp
                420                 425                 430

Phe His Glu Met Gln Glu Leu Lys Val Arg Ala Glu Ala Ala Asp Val
            435                 440                 445

Ala Lys Ser Gln Phe Leu Ala Thr Val Ser His Glu Ile Arg Thr Pro
450                 455                 460

Met Asn Gly Ile Leu Gly Met Leu Ala Met Leu Leu Asp Thr Glu Leu
465                 470                 475                 480

Ser Ser Thr Gln Arg Asp Tyr Ala Gln Thr Ala Gln Val Cys Gly Lys
                485                 490                 495

Ala Leu Ile Ala Leu Ile Asn Glu Val Leu Asp Arg Ala Lys Ile Glu
            500                 505                 510

Ala Gly Lys Leu Glu Leu Glu Ser Val Pro Phe Asp Ile Arg Ser Ile
        515                 520                 525

Leu Asp Asp Val Leu Ser Leu Phe Ser Glu Glu Ser Arg Asn Lys Gly
530                 535                 540

Ile Glu Leu Ala Val Phe Val Ser Asp Lys Val Pro Glu Ile Val Lys
545                 550                 555                 560

Gly Asp Ser Gly Arg Phe Arg Gln Ile Ile Asn Leu Val Gly Asn
                565                 570                 575

Ser Val Lys Phe Thr Glu Lys Gly His Ile Phe Val Lys Val His Leu
            580                 585                 590

Ala Glu Gln Ser Lys Asp Glu Ser Glu Pro Lys Asn Ala Leu Asn Gly
        595                 600                 605

Gly Val Ser Glu Glu Met Ile Val Val Ser Lys Gln Ser Ser Tyr Asn
610                 615                 620

Thr Leu Ser Gly Tyr Glu Ala Ala Asp Gly Arg Asn Ser Trp Asp Ser
625                 630                 635                 640

Phe Lys His Leu Val Ser Glu Glu Gln Ser Leu Ser Glu Phe Asp Ile
                645                 650                 655

Ser Ser Asn Val Arg Leu Met Val Ser Ile Glu Asp Thr Gly Ile Gly
            660                 665                 670

Ile Pro Leu Val Ala Gln Gly Arg Val Phe Met Pro Phe Met Gln Ala
        675                 680                 685

Asp Ser Thr Ser Arg Asn Tyr Gly Gly Thr Gly Ile Gly Leu Ser
690                 695                 700

Ile Ser Lys Cys Leu Val Glu Leu Met Arg Gly Gln Ile Asn Phe Ile
705                 710                 715                 720

Ser Arg Pro His Ile Gly Ser Thr Phe Trp Phe Thr Ala Val Leu Glu
                725                 730                 735

Lys Cys Asp Lys Cys Ser Ala Ile Asn His Met Lys Lys Pro Asn Val
            740                 745                 750

Glu His Leu Pro Ser Thr Phe Lys Gly Met Lys Ala Ile Val Val Asp
        755                 760                 765

Ala Lys Pro Val Arg Ala Ala Val Thr Arg Tyr His Met Lys Arg Leu
770                 775                 780

Gly Ile Asn Val Asp Val Val Thr Ser Leu Lys Thr Ala Val Val Ala
785                 790                 795                 800

Ala Ala Ala Phe Glu Arg Asn Gly Ser Pro Leu Pro Thr Lys Pro Gln
                805                 810                 815

Leu Asp Met Ile Leu Val Glu Lys Asp Ser Trp Ile Ser Thr Glu Asp
            820                 825                 830

Asn Asp Ser Glu Ile Arg Leu Leu Asn Ser Arg Thr Asn Gly Asn Val
```

```
                835              840              845
His His Lys Ser Pro Lys Leu Ala Leu Phe Ala Thr Asn Ile Thr Asn
        850              855              860

Ser Glu Phe Asp Arg Ala Lys Ser Ala Gly Phe Ala Asp Thr Val Ile
865              870              875              880

Met Lys Pro Leu Arg Ala Ser Met Ile Gly Ala Cys Leu Gln Gln Val
                885              890              895

Leu Glu Leu Arg Lys Thr Arg Gln Gln His Pro Glu Gly Ser Ser Pro
            900              905              910

Ala Thr Leu Lys Ser Leu Leu Thr Gly Lys Lys Ile Leu Val Val Asp
        915              920              925

Asp Asn Ile Val Asn Arg Arg Val Ala Ala Gly Ala Leu Lys Lys Phe
    930              935              940

Gly Ala Glu Val Val Cys Ala Glu Ser Gly Gln Val Ala Leu Gly Leu
945              950              955              960

Leu Gln Ile Pro His Thr Phe Asp Ala Cys Phe Met Asp Ile Gln Met
                965              970              975

Pro Gln Met Asp Gly Phe Glu Ala Thr Arg Gln Ile Arg Met Met Glu
            980              985              990

Lys Glu Ala Lys Glu Lys Thr Asn  Leu Glu Trp His Leu  Pro Ile Leu
        995              1000              1005

Ala Met  Thr Ala Asp Val Ile  His Ala Thr Tyr Glu  Glu Cys Leu
    1010              1015              1020

Lys Ser  Gly Met Asp Gly Tyr  Val Ser Lys Pro Phe  Glu Glu Glu
    1025              1030              1035

Asn Leu  Tyr Lys Ser Val Ala  Lys Ser Phe Lys Pro  Asn Pro Ile
    1040              1045              1050

Ser Pro  Ser Ser
    1055

<210> SEQ ID NO 2
<211> LENGTH: 3174
<212> TYPE: DNA
<213> ORGANISM: Arabidopsis thaliana
<220> FEATURE:
<221> NAME/KEY: CDS
<222> LOCATION: (1)..(3174)

<400> SEQUENCE: 2 atg aac tgg gca ctc aac aat cat caa gaa gaa gaa gaa gag cca cga    48
Met Asn Trp Ala Leu Asn Asn His Gln Glu Glu Glu Glu Glu Pro Arg
1               5                   10                  15 aga att gaa att tct gat tcc gag tca cta gaa aac ttg aaa agc agc    96
Arg Ile Glu Ile Ser Asp Ser Glu Ser Leu Glu Asn Leu Lys Ser Ser
            20                  25                  30 gat ttt tat caa ctg ggt ggt ggt ggt gct ctg aat tcg tca gaa aag   144
Asp Phe Tyr Gln Leu Gly Gly Gly Gly Ala Leu Asn Ser Ser Glu Lys
        35                  40                  45 ccg aga aag atc gat ttt tgg cgt tcg ggg ttg atg ggt ttt gcg aag   192
Pro Arg Lys Ile Asp Phe Trp Arg Ser Gly Leu Met Gly Phe Ala Lys
    50                  55                  60 atg cag cag cag caa cag ctt cag cat tca gtg gcg gtg aag atg aac   240
Met Gln Gln Gln Gln Gln Leu Gln His Ser Val Ala Val Lys Met Asn
65                  70                  75                  80 aat aat aat aat aac gat cta atg ggt aat aaa aaa ggg tca act ttc   288
Asn Asn Asn Asn Asn Asp Leu Met Gly Asn Lys Lys Gly Ser Thr Phe
                85                  90                  95 ata caa gaa cat cga gca ttg tta cca aaa gct ttg att ctg tgg atc   336
```

```
Ile Gln Glu His Arg Ala Leu Leu Pro Lys Ala Leu Ile Leu Trp Ile
                100                 105                 110 atc att gtt ggg ttt ata agc agt ggg att tat cag tgg atg gat gat       384
Ile Ile Val Gly Phe Ile Ser Ser Gly Ile Tyr Gln Trp Met Asp Asp
            115                 120                 125 gct aat aag att aga agg gaa gag gtt ttg gtc agc atg tgt gat caa       432
Ala Asn Lys Ile Arg Arg Glu Glu Val Leu Val Ser Met Cys Asp Gln
130                 135                 140 aga gct aga atg ttg cag gat caa ttt agt gtt agt gtt aat cat gtt       480
Arg Ala Arg Met Leu Gln Asp Gln Phe Ser Val Ser Val Asn His Val
145                 150                 155                 160 cat gct ttg gct att ctc gtc tcc act ttt cat tac cac aag aac cct       528
His Ala Leu Ala Ile Leu Val Ser Thr Phe His Tyr His Lys Asn Pro
                165                 170                 175 tct gca att gat cag gag aca ttt gcg gag tac acg gca aga aca gca       576
Ser Ala Ile Asp Gln Glu Thr Phe Ala Glu Tyr Thr Ala Arg Thr Ala
            180                 185                 190 ttt gag aga ccg ttg cta agt gga gtg gct tat gct gaa aaa gtt gtg       624
Phe Glu Arg Pro Leu Leu Ser Gly Val Ala Tyr Ala Glu Lys Val Val
        195                 200                 205 aat ttt gag agg gag atg ttt gag cgg cag cac aat tgg gtt ata aag       672
Asn Phe Glu Arg Glu Met Phe Glu Arg Gln His Asn Trp Val Ile Lys
210                 215                 220 aca atg gat aga gga gag cct tca ccg gtt agg gat gag tat gct cct       720
Thr Met Asp Arg Gly Glu Pro Ser Pro Val Arg Asp Glu Tyr Ala Pro
225                 230                 235                 240 gtt ata ttc tct caa gat agt gtc tct tac ctt gag tca ctc gat atg       768
Val Ile Phe Ser Gln Asp Ser Val Ser Tyr Leu Glu Ser Leu Asp Met
                245                 250                 255 atg tca ggc gag gag gat cgt gag aat att ttg cga gct aga gaa acc       816
Met Ser Gly Glu Glu Asp Arg Glu Asn Ile Leu Arg Ala Arg Glu Thr
            260                 265                 270 gga aaa gct gtc ttg act agc cct ttt agg ttg ttg gaa act cac cat       864
Gly Lys Ala Val Leu Thr Ser Pro Phe Arg Leu Leu Glu Thr His His
        275                 280                 285 ctc gga gtt gtg ttg aca ttc cct gtc tac aag tct tct ctt cct gaa       912
Leu Gly Val Val Leu Thr Phe Pro Val Tyr Lys Ser Ser Leu Pro Glu
290                 295                 300 aat ccg act gtc gaa gag cgt att gca gcc act gca ggg tac ctt ggt       960
Asn Pro Thr Val Glu Glu Arg Ile Ala Ala Thr Ala Gly Tyr Leu Gly
305                 310                 315                 320 ggt gcg ttt gat gtg gag tct cta gtc gag aat tta ctt ggt cag ctt      1008
Gly Ala Phe Asp Val Glu Ser Leu Val Glu Asn Leu Leu Gly Gln Leu
                325                 330                 335 gct ggt aac caa gca ata gtt gtg cat gtg tat gat atc acc aat gca      1056
Ala Gly Asn Gln Ala Ile Val Val His Val Tyr Asp Ile Thr Asn Ala
            340                 345                 350 tca gat cca ctt gtc atg tat ggt aat caa gat gaa gaa gcc gac aga      1104
Ser Asp Pro Leu Val Met Tyr Gly Asn Gln Asp Glu Glu Ala Asp Arg
        355                 360                 365 tct ctc tct cat gag agc aag ctc gat ttt gga gac ccc ttc agg aaa      1152
Ser Leu Ser His Glu Ser Lys Leu Asp Phe Gly Asp Pro Phe Arg Lys
370                 375                 380 cat aag atg ata tgc agg tac cac caa aag gca cca ata cca ttg aat      1200
His Lys Met Ile Cys Arg Tyr His Gln Lys Ala Pro Ile Pro Leu Asn
385                 390                 395                 400 gtg ctc aca act gtg cca ttg ttc ttt gcg att ggt ttc ttg gtg ggt      1248
Val Leu Thr Thr Val Pro Leu Phe Phe Ala Ile Gly Phe Leu Val Gly
                405                 410                 415 tat ata ctg tat ggt gca gct atg cac ata gta aaa gtc gaa gat gat      1296
```

```
Tyr Ile Leu Tyr Gly Ala Ala Met His Ile Val Lys Val Glu Asp Asp
            420                 425                 430 ttc cat gaa atg caa gag ctt aaa gtg cga gca gaa gct gct gat gtc      1344
Phe His Glu Met Gln Glu Leu Lys Val Arg Ala Glu Ala Ala Asp Val
            435                 440                 445 gct aaa tcg cag ttt ctt gct acc gtg tct cac gag atc agg aca cca      1392
Ala Lys Ser Gln Phe Leu Ala Thr Val Ser His Glu Ile Arg Thr Pro
450                 455                 460 atg aat ggc att ctc gga atg ctt gct atg ctc cta gat aca gaa cta      1440
Met Asn Gly Ile Leu Gly Met Leu Ala Met Leu Leu Asp Thr Glu Leu
465                 470                 475                 480 agc tcg aca cag aga gat tac gct caa acc gct caa gta tgt ggt aaa      1488
Ser Ser Thr Gln Arg Asp Tyr Ala Gln Thr Ala Gln Val Cys Gly Lys
                485                 490                 495 gct ttg att gca ttg ata aat gag gtt ctt gat cgc gcc aag att gaa      1536
Ala Leu Ile Ala Leu Ile Asn Glu Val Leu Asp Arg Ala Lys Ile Glu
            500                 505                 510 gct gga aag ctg gag ttg gaa tca gta cca ttt gat atc cgt tca ata      1584
Ala Gly Lys Leu Glu Leu Glu Ser Val Pro Phe Asp Ile Arg Ser Ile
        515                 520                 525 ttg gat gat gtc ctt tct cta ttc tct gag gag tca agg aac aaa ggc      1632
Leu Asp Asp Val Leu Ser Leu Phe Ser Glu Glu Ser Arg Asn Lys Gly
    530                 535                 540 att gag ctc gcg gtt ttc gtt tca gac aaa gta cca gag ata gtc aaa      1680
Ile Glu Leu Ala Val Phe Val Ser Asp Lys Val Pro Glu Ile Val Lys
545                 550                 555                 560 gga gat tca ggg aga ttt aga cag ata atc ata aac ctt gtt gga aat      1728
Gly Asp Ser Gly Arg Phe Arg Gln Ile Ile Ile Asn Leu Val Gly Asn
                565                 570                 575 tcg gtt aaa ttc aca gag aaa gga cat atc ttt gtt aaa gtc cat ctt      1776
Ser Val Lys Phe Thr Glu Lys Gly His Ile Phe Val Lys Val His Leu
            580                 585                 590 gcg gaa caa tca aaa gat gaa tct gaa ccg aaa aat gca ttg aat ggt      1824
Ala Glu Gln Ser Lys Asp Glu Ser Glu Pro Lys Asn Ala Leu Asn Gly
        595                 600                 605 gga gtg tct gaa gaa atg atc gtt gtt tcc aaa cag tca agt tac aac      1872
Gly Val Ser Glu Glu Met Ile Val Val Ser Lys Gln Ser Ser Tyr Asn
    610                 615                 620 aca ttg agc ggt tac gaa gct gct gat ggt cgg aat agc tgg gat tca      1920
Thr Leu Ser Gly Tyr Glu Ala Ala Asp Gly Arg Asn Ser Trp Asp Ser
625                 630                 635                 640 ttc aag cat ttg gtc tct gag gag cag tca tta tcg gag ttt gat att      1968
Phe Lys His Leu Val Ser Glu Glu Gln Ser Leu Ser Glu Phe Asp Ile
                645                 650                 655 tct agc aat gtt agg ctt atg gtt tca atc gaa gac acg ggt att gga      2016
Ser Ser Asn Val Arg Leu Met Val Ser Ile Glu Asp Thr Gly Ile Gly
            660                 665                 670 atc cct tta gtt gca caa ggc cgt gtg ttt atg ccg ttt atg caa gca      2064
Ile Pro Leu Val Ala Gln Gly Arg Val Phe Met Pro Phe Met Gln Ala
        675                 680                 685 gat agc tcg act tca aga aac tat gga ggt act ggt att ggt ttg agt      2112
Asp Ser Ser Thr Ser Arg Asn Tyr Gly Gly Thr Gly Ile Gly Leu Ser
    690                 695                 700 ata agc aag tgt ctt gtt gaa ctt atg cgt ggt cag ata aat ttc ata      2160
Ile Ser Lys Cys Leu Val Glu Leu Met Arg Gly Gln Ile Asn Phe Ile
705                 710                 715                 720 agc cgg cct cat att gga agc acg ttc tgg ttc acg gct gtt tta gag      2208
Ser Arg Pro His Ile Gly Ser Thr Phe Trp Phe Thr Ala Val Leu Glu
                725                 730                 735
```

```
aaa tgc gat aaa tgc agt gcg att aac cat atg aag aaa cct aat gtg      2256
Lys Cys Asp Lys Cys Ser Ala Ile Asn His Met Lys Lys Pro Asn Val
            740                 745                 750 gaa cac ttg cct tct act ttt aaa gga atg aaa gct ata gtt gtt gat      2304
Glu His Leu Pro Ser Thr Phe Lys Gly Met Lys Ala Ile Val Val Asp
                755                 760                 765 gct aag cct gtt aga gct gct gtg act aga tac cat atg aaa aga ctc      2352
Ala Lys Pro Val Arg Ala Ala Val Thr Arg Tyr His Met Lys Arg Leu
    770                 775                 780 gga atc aat gtt gat gtc gta aca agt ctc aaa acc gct gtt gtt gca      2400
Gly Ile Asn Val Asp Val Val Thr Ser Leu Lys Thr Ala Val Val Ala
785                 790                 795                 800 gct gct gcg ttt gaa aga aac ggt tct cct ctc cca aca aaa ccg caa      2448
Ala Ala Ala Phe Glu Arg Asn Gly Ser Pro Leu Pro Thr Lys Pro Gln
                805                 810                 815 ctt gat atg atc tta gta gag aaa gat tca tgg att tca act gaa gat      2496
Leu Asp Met Ile Leu Val Glu Lys Asp Ser Trp Ile Ser Thr Glu Asp
                820                 825                 830 aat gac tca gag att cgt tta ttg aat tca aga acc aac gga aac gtt      2544
Asn Asp Ser Glu Ile Arg Leu Leu Asn Ser Arg Thr Asn Gly Asn Val
            835                 840                 845 cat cac aag tct ccg aaa cta gct cta ttc gca aca aac atc aca aat      2592
His His Lys Ser Pro Lys Leu Ala Leu Phe Ala Thr Asn Ile Thr Asn
850                 855                 860 tcg gag ttc gac aga gct aaa tcc gca gga ttt gca gat acg gta ata      2640
Ser Glu Phe Asp Arg Ala Lys Ser Ala Gly Phe Ala Asp Thr Val Ile
865                 870                 875                 880 atg aaa ccg tta aga gca agc atg att ggg gcg tgt ctg caa caa gtt      2688
Met Lys Pro Leu Arg Ala Ser Met Ile Gly Ala Cys Leu Gln Gln Val
                885                 890                 895 ctc gag ctg aga aaa aca aga caa caa cat cca gaa gga tca tca ccc      2736
Leu Glu Leu Arg Lys Thr Arg Gln Gln His Pro Glu Gly Ser Ser Pro
            900                 905                 910 gca act ctc aag agc ttg ctt aca ggg aag aag att ctt gtg gtt gat      2784
Ala Thr Leu Lys Ser Leu Leu Thr Gly Lys Lys Ile Leu Val Val Asp
                915                 920                 925 gat aat ata gtt aac agg aga gta gct gca gga gct ctc aag aaa ttt      2832
Asp Asn Ile Val Asn Arg Arg Val Ala Ala Gly Ala Leu Lys Lys Phe
            930                 935                 940 gga gca gaa gtg gtt tgt gca gag agt ggt caa gtt gct ttg ggt ttg      2880
Gly Ala Glu Val Val Cys Ala Glu Ser Gly Gln Val Ala Leu Gly Leu
945                 950                 955                 960 ctt cag att cca cac act ttc gat gct tgc ttc atg gat att caa atg      2928
Leu Gln Ile Pro His Thr Phe Asp Ala Cys Phe Met Asp Ile Gln Met
                965                 970                 975 cca cag atg gac gga ttt gaa gca act cgt cag ata aga atg atg gag      2976
Pro Gln Met Asp Gly Phe Glu Ala Thr Arg Gln Ile Arg Met Met Glu
            980                 985                 990 aag gaa gct aaa gag aag acg aat  ctc gaa tgg cat tta  ccg att cta    3024
Lys Glu Ala Lys Glu Lys Thr Asn  Leu Glu Trp His Leu  Pro Ile Leu
                995                  1000                1005 gcg atg act gcg gat gtg ata  cac gcg acc tac gag  gaa tgt ctg        3069
Ala Met Thr Ala Asp Val Ile  His Ala Thr Tyr Glu  Glu Cys Leu
    1010                1015                1020 aaa agt ggg atg gat ggt tac gtc tcc aaa cct ttt  gaa gaa gag         3114
Lys Ser Gly Met Asp Gly Tyr Val Ser Lys Pro Phe  Glu Glu Glu
    1025                1030                 1035 aat ctc tat aaa tcc gtt gcc  aaa tca ttc aaa cct  aat cct atc        3159
Asn Leu Tyr Lys Ser Val Ala  Lys Ser Phe Lys Pro  Asn Pro Ile
    1040                1045                 1050
```

-continued

```
tca cct  tcg tcg taa                                              3174
Ser Pro  Ser Ser
    1055

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 3
tcagatatga actgggcact caac                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 4
ctcaatgctt ttgttccttg actc                                          24

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 5
accatgaact gggcactcaa caatcatcaa g                                  31

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 6
ggattacgac gaaggtgaga taggattagg                                    30

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 7
cgggatccat gaactgggca ctcaacaatc atc                                33

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:Designed
      oligonucleotide primer for PCR
```

```
<400> SEQUENCE: 8
gctctagatt acgacgaagg tgagatagga ttag                    34
```

AGENT FOR INHIBITING CYTOKININ SIGNALING

TECHNICAL FIELD

The present invention relates to an agent which has an activity of inhibiting intracellular signaling from a plant-derived cytokinin receptor and controls the growth or differentiation of a plant, and the like.

BACKGROUND ART

Cytokinin is a plant hormone involved in cell division and differentiation of higher plants, and is an important biologically active substance which is known to exert actions such as induction of division of higher plant cells, differentiation from callus or pith to foliage, prevention of etiolation of leaves, fallen leaves and fallen fruit, and defeat of apical dominance (Cytokinins: Chemistry, Activity, and Function, CRC Press (1994)). As a method of controlling physiological phenomena caused by cytokinin, a method comprising giving cytokinin from the outside, a method comprising controlling biosynthesis of cytokinin in a plant body, a method comprising controlling metabolism of cytokinin in a plant body and the like have been proposed.

A chemical substance serving as the active ingredient of a plant growth regulator has been conventionally found by random screening in which a test chemical substance is directly contacted with a plant and then a biological activity of the plant is tested. In this case, after a chemical substance having a useful biological activity is determined, it is necessary to intensively study what kind of mechanism of action there is for the chemical substance to exert its effect and what is targeted by the chemical substance on the molecular level, in order to predict safety and burden on the environment of the chemical substance.

DISCLOSURE OF INVENTION

An object of the present invention is to provide an agent capable of controlling the growth or differentiation of a plant, and a method for searching a chemical substance having a useful biological activity whose target has been made clear, that is, a method for screening a chemical substance using an activity on a specific target as an indicator so as to chemically control a target site. Specifically, an object of the present invention is to provide an agent which has an activity of inhibiting intracellular signaling from a plant-derived cytokinin receptor and controls the growth or differentiation of a plant, and a method for searching a chemical substance which serves as an active ingredient of the agent.

Thus, the present invention provides;

(1) an agent capable of controlling the growth or differentiation of a plant which has an activity of inhibiting intracellular signaling from a plant-derived cytokinin receptor of a cell;

(2) the agent according to the above (1), wherein the agent capable of controlling the growth or differentiation of a plant is a plant growth regulator;

(3) the agent according to the above (1), wherein the agent capable of controlling the growth or differentiation of a plant is an agent capable of controlling the growth of a plant body;

(4) the agent according to the above (1), wherein the agent capable of controlling the growth or differentiation of a plant is an agent capable of controlling the differentiation of a plant cell;

(5) the agent according to the above (3), wherein the agent capable of controlling the growth of a plant is an agent capable of controlling the growth of a bud of a plant;

(6) the agent according to the above (5), wherein control of the growth of a bud of a plant is inhibition of the growth of an axillary bud;

(7) the agent according to the above (5), wherein control of the growth of a bud of a plant is inhibition of the growth of a flower bud;

(8) the agent according to the above (3), wherein the agent capable of controlling the growth of a plant body is an agent capable of promoting the stand establishment of a plant;

(9) the agent according to the above (3), wherein the agent capable of controlling the growth of a plant body is an agent capable of promoting the tillering of a plant;

(10) the agent according to the above (3), wherein the agent capable of controlling the growth of a plant body is an agent capable of promoting the growth of a root of a plant;

(11) the agent according to any one of the above (1) to (10), wherein the plant-derived cytokinin receptor of a cell is a cytokinin receptor selected from the following group A:

<Group A>

(a) a protein comprising the amino acid sequence of SEQ ID NO:1, (b) a protein comprising an amino acid sequence of SEQ ID NO:1 in which one or more amino acids are deleted, added or substituted, and having an activity of functioning as a cytokinin receptor, (c) a protein comprising an amino acid sequence having a sequence identity of 45% or more with the amino acid sequence of SEQ ID NO:1, and having an activity of functioning as a cytokinin receptor (d) a protein comprising an amino acid sequence encoded by the nucleotide sequence of SEQ ID NO:2

(e) a protein comprising an amino acid sequence encoded by a polynucleotide that hybridizes under a stringent condition with a polynucleotide complementary to a polynucleotide having the nucleotide sequence of SEQ ID NO:2, and having an activity of functioning as a cytokinin receptor;

(12) the agent according to any one of the above (1) to (10), wherein the activity of inhibiting intracellular signaling from a plant-derived cytokinin receptor of a cell is an activity of inhibiting intracellular signaling from a cytokinin receptor selected from the following group A in a contact system of a cell having the cytokinin receptor with a substance having an agonistic activity to the cytokinin receptor;

<Group A>

(a) a protein comprising the amino acid sequence of SEQ ID NO:1, (b) a protein comprising an amino acid sequence of SEQ ID NO:1 in which one or more amino acids are deleted, added or substituted, and having an activity of functioning as a cytokinin receptor, (c) a protein comprising an amino acid sequence having a sequence identity of 45% or more with the amino acid sequence of SEQ ID NO:1, and having an activity of functioning as a cytokinin receptor (d) a protein comprising an amino acid sequence encoded by the nucleotide sequence of SEQ ID NO:2

(e) a protein comprising an amino acid sequence encoded by a polynucleotide that hybridizes under a stringent condition with a polynucleotide complementary to a polynucleotide having the nucleotide sequence of SEQ ID NO:2, and having an activity of functioning as a cytokinin receptor;

(13) a plant growth regulator comprising a chemical substance capable of inhibiting intracellular signaling from a plant-derived cytokinin receptor of a cell, or an agriculturally acceptable salt thereof, as an active ingredient;

(14) the plant growth regulator according to the above (13), wherein the chemical substance has an activity of inhibiting intracellular signaling from a cytokinin receptor selected from the following group A in a contact system comprising a cell having the cytokinin receptor, a substance having an agonistic activity to the cytokinin receptor, and the chemical substance;

<Group A>

(a) a protein comprising the amino acid sequence of SEQ ID NO:1, (b) a protein comprising an amino acid sequence of SEQ ID NO:1 in which one or more amino acids are deleted, added or substituted, and having an activity of functioning as a cytokinin receptor, (c) a protein comprising an amino acid sequence having a sequence identity of 45% or more with the amino acid sequence of SEQ ID NO:1, and having an activity of functioning as a cytokinin receptor (d) a protein comprising an amino acid sequence encoded by the nucleotide sequence of SEQ ID NO:2

(e) a protein comprising an amino acid sequence encoded by a polynucleotide that hybridizes under a stringent condition with a polynucleotide complementary to a polynucleotide having the nucleotide sequence of SEQ ID NO:2, and having an activity of functioning as a cytokinin receptor;

(15) the plant growth regulator according to the above (14), wherein the substance having an agonistic activity to the cytokinin receptor is trans-zeatin;

(16) the plant growth regulator according to the above (13), wherein the chemical substance has an activity of lowering intracellular signaling from a cytokinin receptor selected from the following group A in a contact system comprising a cell having the cytokinin receptor, 0.6 ppm of trans-zeatine and 2 ppm of the chemical substance, as compared with the case where the chemical substance is not present in the contact system;

<Group A>

(a) a protein comprising the amino acid sequence of SEQ ID NO:1, (b) a protein comprising an amino acid sequence of SEQ ID NO:1 in which one or more amino acids are deleted, added or substituted, and having an activity of functioning as a cytokinin receptor, (c) a protein comprising an amino acid sequence having a sequence identity of 45% or more with the amino acid sequence of SEQ ID NO:1, and having an activity of functioning as a cytokinin receptor (d) a protein comprising an amino acid sequence encoded by the nucleotide sequence of SEQ ID NO:2

(e) a protein comprising an amino acid sequence encoded by a polynucleotide that hybridizes under a stringent condition with a polynucleotide complementary to a polynucleotide having the nucleotide sequence of SEQ ID NO:2, and having an activity of functioning as a cytokinin receptor;

(17) the plant growth regulator according to the above (13), wherein the chemical substance has an activity of lowering intracellular signaling from a cytokinin receptor selected from the following group A by 90% or more in a contact system comprising a cell having the cytokinin receptor, 0.6 ppm of trans-zeatine and 2 ppm of the chemical substance, as compared with the case where the chemical substance is not present in the contact system;

<Group A>

(a) a protein comprising the amino acid sequence of SEQ ID NO:1, (b) a protein comprising an amino acid sequence of SEQ ID NO:1 in which one or more amino acids are deleted, added or substituted, and having an activity of functioning as a cytokinin receptor, (c) a protein comprising an amino acid sequence having a sequence identity of 45% or more with the amino acid sequence of SEQ ID NO:1, and having an activity of functioning as a cytokinin receptor (d) a protein comprising an amino acid sequence encoded by the nucleotide sequence of SEQ ID NO:2

(e) a protein comprising an amino acid sequence encoded by a polynucleotide that hybridizes under a stringent condition with a polynucleotide complementary to a polynucleotide having the nucleotide sequence of SEQ ID NO:2, and having an activity of functioning as a cytokinin receptor;

(18) a method for searching a chemical substance capable of promoting the growth of a root of a plant, which comprises:

<1> a first step of measuring the amount of intracellular signaling from a cytokinin receptor selected from the following group A in a contact system comprising a cell having the cytokinin receptor, a substance having an agonistic activity to the cytokinin receptor and a test substance; and <2> a second step of selecting a chemical substance capable of promoting the growth of a root of a plant on the basis of a difference obtained by comparing the amount of intracellular signaling measured in the first step with the amount of intracellular signaling in the absence of the chemical substance;

<Group A>

(a) a protein comprising the amino acid sequence of SEQ ID NO:1, (b) a protein comprising an amino acid sequence of SEQ ID NO:1 in which one or more amino acids are deleted, added or substituted, and having an activity of functioning as a cytokinin receptor, (c) a protein comprising an amino acid sequence having a sequence identity of 45% or more with the amino acid sequence of SEQ ID NO:1, and having an activity of functioning as a cytokinin receptor (d) a protein comprising an amino acid sequence encoded by the nucleotide sequence of SEQ ID NO:2

(e) a protein comprising an amino acid sequence encoded by a polynucleotide that hybridizes under a stringent condition with a polynucleotide complementary to a polynucleotide having the nucleotide sequence of SEQ ID NO:2, and having an activity of functioning as a cytokinin receptor;

(19) the searching method according to the above (18), wherein the cell having the cytokinin receptor is a transformed cell into which a polynucleotide comprising a nucleotide sequence encoding the amino acid sequence of SEQ ID NO:1 is introduced;

(20) the searching method according to the above (18), wherein the cell having the cytokinin receptor is a transformed yeast cell into which a polynucleotide comprising a nucleotide sequence encoding the amino acid sequence of SEQ ID NO:1 is introduced;

(21) the searching method according to the above (18), (19) or (20), wherein the substance having an agonistic activity to the cytokinin receptor is trans-zeatin;

(22) a plant growth regulator comprising a chemical substance selected by the searching method according to the above (18), (19), (20) or (21), or an agriculturally acceptable salt thereof, as an active ingredient;

(23) a plant growth regulating method, which comprises applying an effective amount of the plant growth regulator according to the above (13), (14), (15), (16), (17) or (22) to a plant or a habitat of the plant;

(24) a plant growth regulating method, which comprises determining a chemical substance capable of promoting the growth of a root of a plant by the searching method according to the above (18), (19), (20) or (21), and bringing the chemical substance capable of promoting the growth of a root of a plant thus determined into contact with a plant;

(25) a plant growth regulator comprising a compound represented by the general formula (I):

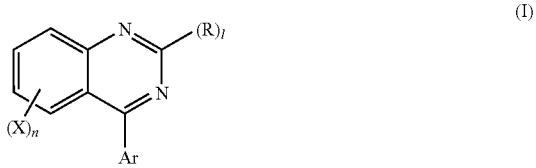

wherein R and X are the same or different and represent an optionally substituted hydrocarbon group, a group represented by $NR^1R^2$, a group represented by $OR^3$, a group represented by $S(O)_mR^4$, a nitro group or a halogen atom, in which $R^1$ represents a hydrogen atom or an optionally substituted hydrocarbon group, $R^2$ represents a hydrogen atom, an optionally substituted hydrocarbon group, a group represented by $NR^5R^6$ (in which $R^5$ and $R^6$ are the same or different and represent a hydrogen atom or an optionally substituted C1-6 alkyl group) or a group represented by $OR^7$ (in which $R^7$ represents a hydrogen atom or an optionally substituted C1-6 alkyl group), or $R^1$ and $R^2$ are taken together with the nitrogen atom to which they are attached to form an optionally substituted cyclic amino group, $R^3$ and $R^4$ each represent an optionally substituted hydrocarbon group, l represents an integer of 0 to 1, m represents an integer of 0 to 2, n represents an integer of 0 to 4, when n is 2 or more, each X is the same or different from each other, and Ar represents an optionally substituted aryl group or an optionally substituted heteroaryl group; or an agriculturally acceptable salt thereof, as an active ingredient;

(26) the plant growth regulator according to the above (25), wherein l is 1 and R is an optionally substituted hydrocarbon group;

(27) the plant growth regulator according to the above (25), wherein l is 1 and R is a C1-3 alkyl group which is optionally substituted with (a) halogen atom(s) or (an) oxo group(s);

(28) the plant growth regulator according to the above (26), wherein the optionally substituted hydrocarbon group is a C1-3 alkyl group which is optionally substituted with (a) halogen atom(s) or (an) oxo group(s);

(29) the plant growth regulator according to the above (25), wherein l is 1 and R is a group represented by $NR^1R^2$;

(30) the plant growth regulator according to the above (29), wherein $R^1$ represents a hydrogen atom or a C1-3 alkyl group, $R^2$ represents a hydrogen atom, an amino group, a C1-3 alkylamino group, a di C1-3 alkylamino group, an amidino group, a C1-3 alkoxy group, a phenyl group, a C1-3 acyl group, a C1-6 alkyl group, a C3-6 alkenyl group or a C3-6 alkynyl group, in which the phenyl group is optionally substituted with 1 to 3 same or different C1-3 alkyl groups, the phenyl group, the acyl group, the alkyl group, the alkenyl group and the alkynyl group are optionally substituted with 1 to 3 same or different substituents selected from a halogen atom, a hydroxyl group, a C1-3 alkoxy group, a hydroxy C1-3 alkoxy group, a carboxyl group, a C1-3 alkoxycarbonyl group, a carbamoyl group, an amino group, a C1-3 alkylamino group, a di C1-3 alkylamino group, a mercapto group, a C1-3 acylthio group, a cyano group, a furyl group and a tetrahydrofuryl group, or $R^1$ and $R^2$ are taken together with the nitrogen atom to which they are attached to form a pyrrolidino group, a piperidino group or a morpholino group;

(31) the plant growth regulator according to the above (29), wherein $R^1$ represents a hydrogen atom, $R^2$ represents a hydrogen atom, a formyl group, a C1-6 alkyl group, a C3-6 alkenyl group or a C3-6 alkynyl group, in which the alkyl group, the alkenyl group and the alkynyl group are optionally substituted with (a) substituent(s) selected from a hydroxyl group, a methoxy group, a methoxycarbonyl group, an ethoxycarbonyl group, a cyano group and a furyl group;

(32) the plant growth regulator according to the above (25); wherein l is 1 and R is a group represented by $OR^3$;

(33) the plant growth regulator according to the above (32), wherein $R^3$ is a C1-3 alkyl group which is optionally substituted with an amino group;

(34) the plant growth regulator according to the above (25), wherein l is 1 and R is a group represented by $S(O)_mR^4$;

(35) the plant growth regulator according to the above (34), wherein $R^4$ is a C1-3 alkyl group which is optionally substituted with an amino group or a hydroxyl group, and m is 0;

(36) the plant growth regulator according to the above (25), wherein l is 1 and R is a halogen atom;

(37) the plant growth regulator according to the above (36), wherein the halogen atom is a chlorine atom;

(38) the plant growth regulator according to any one of the above (25) to (37), wherein n is from 1 to 2 and X is a C1-3 alkyl group, a C1-3 alkoxy group, a C1-3 haloalkyl group, a cyano group, a halogen atom or a nitro group;

(39) the plant growth regulator according to the above (38), wherein X is a chlorine atom, a bromine atom or a nitro group, and X is at the 6-position and/or the 8-position;

(40) the plant growth regulator according to any one of the above (25) to (37), wherein Ar is a phenyl group which is optionally substituted with (a) halogen atom(s) or (a) C1-3 alkyl group(s);

(41) a plant growth regulating method, which comprises applying an effective amount of the plant growth regulator according to any one of the above (25) to (40) to a plant or a habitat of the plant;

(42) a compound represented by the formula (XI):

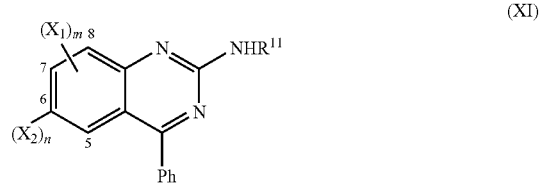

wherein Ph represents a phenyl group, $R^{11}$ represents a hydrogen atom, a formyl group, a C1-6 alkyl group, a C3-6 alkenyl group or a C3-6 alkynyl group, in which the alkyl group, the alkenyl group and the alkynyl group are optionally substituted with at least one substituent selected from a hydroxyl group, a C1-3 alkoxy group, a C1-3 alkoxycarbonyl group, a cyano group, a 2-furyl group and a 2-tetrahydrofuryl group, m represents an integer of 0 to 3, n represents an integer of 0 to 1, at least one of m and n is not 0, $X_1$ and $X_2$ are the same or different and represent a chlorine atom, a bromine atom, a trifluoromethyl group, a cyano group or a nitro group, when m is 2 or more, each $X_1$ is the same or different from each other; provided that
a) when m is 1, $X_1$ is a 5-chlorine atom or a 7-chlorine atom and $R^{11}$ represents a methyl group, n represents an integer of 1, or
b) when n is 1 and any one of conditions (1) to (3) is satisfied, m represents an integer of 1 to 3:
(1) $X_2$ is a chlorine atom, and $R^{11}$ is a group selected from a hydrogen atom, a methyl group, a 2-hydroxyethyl group, a 3-hydroxypropyl group, a 2,2-dimethoxyethyl group and a cyanomethyl group,
(2) $X_2$ is a bromine atom, and $R^{11}$ is a group selected from a 2-hydroxyethyl group, a 3-hydroxypropyl group and a 2-methoxyethyl group, and
(3) $X_2$ is a nitro group, and $R^{11}$ is a 3-hydroxypropyl group; or an agriculturally acceptable salt thereof;

(43) the compound according to the above (42), wherein $R^{11}$ represents a hydrogen atom, a formyl group, a methyl group, an ethyl group, a 2-hydroxyethyl group, a 2-methoxyethyl group, a furfuryl group, a methoxycarbonylmethyl group or an ethoxycarbonylmethyl group, m is 0, n is 1, and $X_2$ is a chlorine atom or a nitro group, or an agriculturally acceptable salt thereof;

(44) the compound according to the above (42), wherein $R^{11}$ represents a hydrogen atom, a formyl group, a methyl group, an ethyl group, a 2-hydroxyethyl group, a 3-hydroxypropyl group, a 2-methoxyethyl group, a furfuryl group, a methoxycarbonylmethyl group or an ethoxycarbonylmethyl group, m is 1, n is 1, $X_1$ is an 8-chlorine atom, and $X_2$ represents a chlorine atom or a nitro group, or an agriculturally acceptable salt thereof;

(45) the compound according to the above (42), wherein m is an integer of 1 to 3 and n is 0, or an agriculturally acceptable salt thereof;

(46) the compound according to the above (42), wherein $R^{11}$ represents a formyl group, a C4-6 alkyl group, a C3-6 alkenyl group or a C3-6 alkynyl group in which the alkyl group, alkenyl group and alkynyl group are optionally substituted with (a) hydroxyl group(s) or (a) C1-3 alkoxy group(s), or $R^{11}$ represents a C1-3 alkoxycarbonylmethyl group, a C1-3 alkoxy C1-3 alkyl group or a furfuryl group, m is 0,
n is 1, and
$X_2$ is a chlorine atom, or an agriculturally acceptable salt thereof;

(47) the compound according to the above (42), wherein n is 1, or an agriculturally acceptable salt thereof;

(48) the compound according to the above (42), wherein m is 1 to 3 and n is 1, or an agriculturally acceptable salt thereof;

(49) the compound according to the above (42), (45), (47) or (48), wherein $R^{11}$ is a C1-3 alkoxycarbonylmethyl group or a furfuryl group, or an agriculturally acceptable salt thereof; and

(50) the compound according to the above (42), wherein n is 1 and $X_2$ is a trifluoromethyl group or a cyano group; and the like.

MODE FOR CARRYING OUT THE INVENTION

Figure 1:
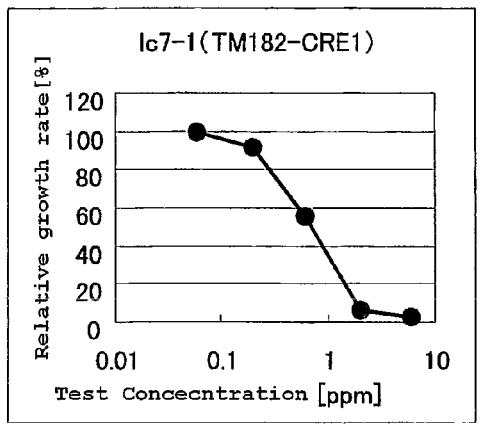
FIG. 1 shows results of a dose-response test using a chemical substance capable of inhibiting intracellular signaling from a plant-derived cytokinin receptor of a cell in Example 8. In the figures, data lines represent dose-response growth inhibition curves, in which X axis represents the concentration of a tested chemical substance and Y axis represents a relative growth rate. The left figures (three subfigures of one left vertical row) show results in test systems using the transformed cell TM182-CRE1. The right figures (three subfigures of one right vertical row) show results in test systems using the transformed cell TM182-p415CYC1. The upper figures, the middle figures, and the lower figures represent results in test systems using the chemical substance Ic7-1, the chemical substance Ic3-1, and the chemical substance Ic3-3, respectively.
Figure 1:
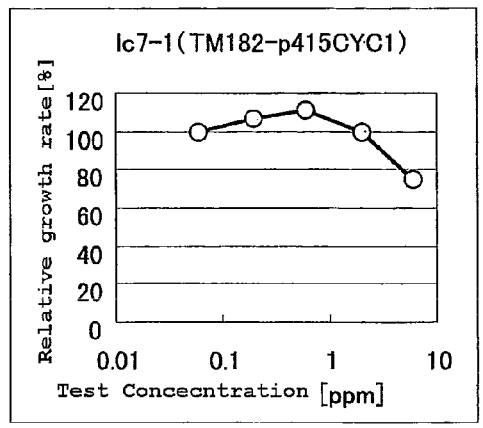
Figure 1:
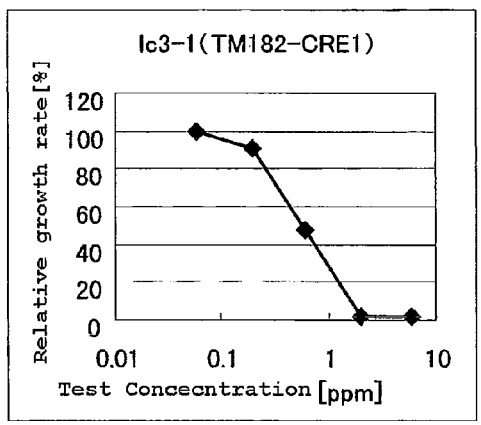
Figure 1:
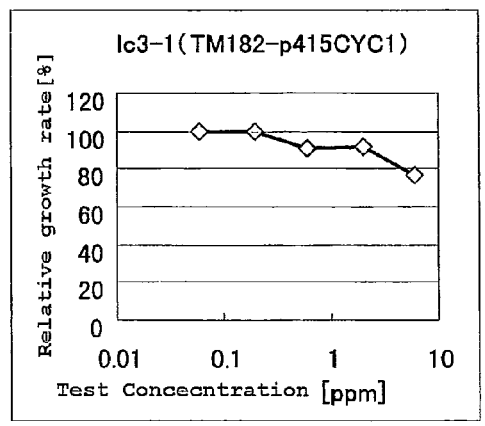
Figure 1:
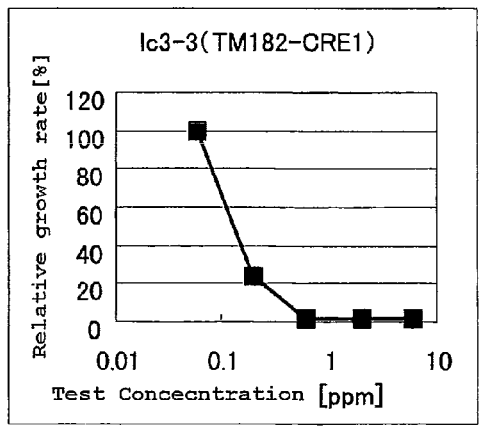
Figure 1:
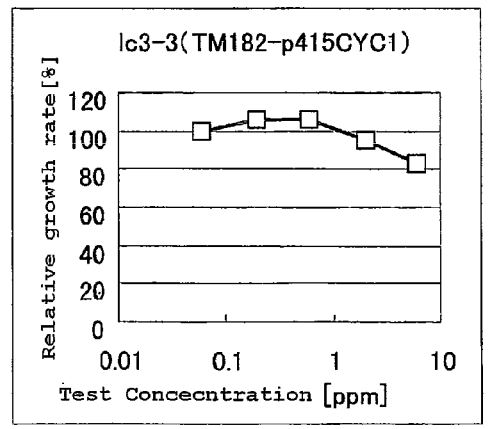

In the present invention, the term "plant" is used in a wide sense which indicates organisms living stationarily through roots, such as grass and trees, and also has a concept including a plant body, a plant tissue, a plant cell and the like. Specifically, the term "plant" means organisms such as higher plants in which an organ referred to as a root can play important roles such as fixation of a plant in soil, and absorption of water and nutrients from the outside, and examples thereof include ornamental plants such as flowering plants and ornamental foliage plants, crops such as grain crops, vegetables and fruit trees, fiberplants, trees, and grasses. Specific examples thereof include cereals such as rice and corn; grasses such as bent grass and Zoysia matrella; cucurbitaceous plants such as tomato, green pepper, red pepper and watermelon; cucurbitaceous plants such as cucumber, pumpkin, melon and watermelon; greens such as cabbage, broccoli and Chinese cabbage; fresh greens such as celery, parsley and lettuce; condiment vegetables; Alliums such as leek, onion and garlic; beans such as soybean, kidney bean, pea and adzuki bean; fruit vegetables such as strawberry; axial roots such as Japanese radish, Japanese turnip, carrot and burdock; potatoes such as taro, potato, sweet potato and yam; soft greens such as asparagus, spinach and honewort; petals such as Eustoma russellianum, stock, carnation and chrysanthemum; oil crops such as rape and peanut; sugar crops such as sugar cane and sugar beet; fiber crops such as cotton and rush; feed crops such as clover and sorghum; deciduous fruit trees such as apple, pear, grape, peach and chestnut; citrus trees such as mandarin orange, lemon and grapefruit; and woody plants such as azalea, rhododendron and cedar.

In the present invention, the term "growth" of a plant means a general process in which already existing vegetative organs (roots, stems, leaves) are newly produced and piled up during a process from the early development of a plant starting at seed germination to the growth and development of roots, stems and leaves, the formation of flowers and then the maturation of seeds. Examples of the growth include germination, growth of roots, extension of buds, extension of stems, formation and extension of terminal buds and axillary buds, development of branches and leaves, formation of flower buds, blooming, seed setting, and maturation of seeds.

In the present invention, the term "differentiation" of a plant means that a plant tissue such as a root, a stem or a leaf is formed from a callus which is a plant cell population acquiring totipotency (redifferentiation), or means that a callus is formed from a cell of a plant tissue such as a root, a stem or a leaf (dedifferentiation).

In the present invention, the "control of the growth of a bud" means promotion or control of the growth of a terminal bud or an axillary bud, and examples thereof include initiation of the axillary bud growth which is suppressed by apical dominance, suppression of the axillary bud growth which is initiated by removing a terminal bud, and suppression of usual terminal bud growth.

In the present invention, the "agent capable of controlling the growth or differentiation of a plant" is an agent which can control the growth or differentiation of a plant by treating the plant with the agent by various methods. Control of the growth or differentiation of a plant is applicable to control of the growth or development of a useful plant such as a farm crop, which makes it possible to enhance early growth, enhance quality, increase a yield, stabilize a yield even under unfavorable conditions, and save labor in the production. Thus, the "agent capable of controlling the growth or differentiation of a plant" can be used as a "plant growth regulator".

In the present invention, the "root" of a plant includes a main root which develops from a radicle existing in an embryo of a seed, and a lateral root which extends from a main root through branching, in the case of dicotyledones and gymnosperms. In the case of monocotyledons, the "root" includes a radicle (seminal root) existing in an embryo of a seed, a crown root (so-called fibrous root) which is formed at the upper portion after termination of the growth of a seminal root, and a lateral root extending from an adventitious root through branching. Also, the "root" occasionally means root hair extending continuously toward the outside which is formed from epidermal cells of a root. The root of a plant is an organ which plays important roles to a plant, such as, fixation of a plant in soil, and absorption of water and nutrients from the outside. The root of a plant is also very important as a place where plant hormone is produced. From an agricultural point of view, many crops propagate through their seeds. Therefore, it is a very important element leading to high quality and high yield that uniform stand establishment is attained at an early stage of the growth of a plant. Promotion of the growth of a root of a plant is expected to have various merits such as improvement in a rate of taking root in soil, improvement in productivity or quality by improvement in stand establishment or the like, weed control at an early stage by improvement in stand establishment, and improvement in efficiency of a seed source. Promotion of root spread is expected to lead to an increase in draught stress resistance or pest resistance, and a decrease in the fertilizer amount by improvement in the nutrient absorption ability.

In the present invention, the "growth of a root" of a plant means that the length of a root and the number of roots increase or that the amount, thickness and activity of a root increase, as a result of division, growth and an increase in weight of root cells.

In the present invention, the "promotion of the growth of a root" of a plant means that the growth of a root of a plant is more activated than usual, and thus the length of a root and the number of roots increase, or the amount, thickness and activity of a root increase as compared with the case of no treatment.

In the present invention, the "agent capable of promoting the growth of a root of a plant" is an agent which can promote the growth of a root of a plant by treating the plant with the substance by various methods. Promotion of the growth of a root of a plant is applicable to control of the growth or development of a useful plant such as a farm crop, which makes it possible to enhance early growth, enhance quality, increase a yield, stabilize a yield even under unfavorable conditions, and save labor in the production. Thus, the "agent capable of promoting the growth of a root of a plant" can be used as a "plant growth regulator".

As used herein, the term "stand establishment" means that a sowed seed germinates and then takes root in soil in a state capable of normally growing as a plant body, or that a transplanted seedling of a plant takes root in soil and then normally grows. Promotion of stand establishment leads to improvement in the early growth of a plant, and thereby it is possible to grow a healthy plant. In addition, as a result of an increase in the number of healthy grown plants, an increase in the final yield is expected. For example, in the case of direct seeding of rice, it is generally difficult to always ensure a given number of established seedlings because of unstable germination and stand establishment. The agent capable of promoting stand establishment of the present invention can promote stand establishment to improve efficiency in direct seeding of rice. The term "stand establishment rate" means the proportion of established plants in the total number of sowed seeds or the total number of transplanted seedlings of a plant. In the case of rice, as used herein, the "stand establishment rate" may be defined by the following equation.

[Stand establishment rate (%)]=[Number of seedlings whose leaf apex appears on the water surface]/ [Number of sowed seeds]×100

The term "tillering" of a plant means branching during the growth of the plant, or branches which arise as a result of tillering. In the case of gramineous plants, for example, the term "tillering" means lateral branches. Promotion of tillering includes earlier tillering and an increase in the number of tillers. For example, when the plant growth regulator of the present invention is used for a plant under stress conditions such as low temperature, high temperature and draught to make the tillering of the plant earlier and thereby healthy seedlings can be early secured by, it is possible to avoid damage of seedlings by stress. For example, earlier tillering results in a shortened cultivation period of a plant. Since formation of tillers of a plant directly influence the number of ears, an increase of yield can be expected depending on cultivation conditions.

An auxin active substance may exhibit unfavorable properties such as epinasty of leaves, stem torsion, stem cracking, and induction of root knots, depending on the kind of a plant, the auxin treatment concentration and the like.

It is believed that cytokinin active substances have both properties of suppressing and promoting the growth of a root of a plant [for example, PNAS 101 (23): 8821-8826 (2004)]. However, in order to utilize such properties in agricultural practice, a lot of findings must be accumulated. Since it is usually difficult to adjust the amount of cytokinin in a plant body (particularly, to reduce the amount of endogenous cytokinin), it is not easy even for a person skilled in the art to specifically investigate roles of cytokinin in a plant.

It is believed that intrinsic cytokinin of a plant can be negatively controlled by inhibiting the cytokinin signaling transduction to weaken the sensitivity to cytokinin. For example, the cytokinin signal transduction can be inhibited by mutating a cytokinin receptor itself, and mutants of cytokinin receptors have been isolated [The Plant Cell 16:1365-1377 (2004), PNAS 101 (23):8821-8826 (2004)]. However, using the mutants, it is difficult to control the degree of inhibition by stages. A single mutant of a cytokinin receptor exhibits the same phenotype as that of the wild type. On the other hand, a triple mutant of a cytokinin receptor exhibits inhibition of root elongation and growth defect of a plant body.

The "plant-derived cytokinin receptor of a cell" in the present invention means a cytokinin receptor existing in a plant. The cytokinin receptor is a protein that specifically binds to cytokinin such as purine cytokinin such as kinetin or zeatin or urea cytokinin such as N-phenyl-N'-(4-pyridyl)urea to control the proliferation and differentiation of higher plant cells through the intracelluler signaling mechanism called a Two-component regulatory system (or His to Asp phosphorelay system). The cytokinin receptor used in the present invention is a protein belonging to the histidine kinase family and composed of an extracellular domain, a transmembrane domain, a histidine kinase domain (a region having a histidine kinase activity in cells and retaining His residues to be an active site) and a receiver domain (a region having a receiving part for phosphate group transfer and retaining Asp residues to be an active site).

The two-component regulatory system is information-receiving and intracellular signaling mechanism that is widely used in eubacteria, ancient bacteria, fungi and plants. In this mechanism, a histidine kinase acts as a receptor and the histidine kinase has an input region for receiving a signal at the N-terminal side and a region relating to phosphate group transfer, which is called a transmitter domain, at the C-terminal side. When the input region realizes a signal; a His residue in the transmitter domain (the above-described histidine kinase domain of a cytokinin receptor) is autophosphorylated. The phosphate group transfers with phosphorylating alternately the conserved specific His and Asp residues, and finally phosphorylates an Asp residue in a receiver domain of a protein called a response regulator. The phosphate group may be transferred directly from the histidine kinase to the response regulator or may be transferred to the response regulator through some stages of phosphate group transfer. A simple Two-Component regulatory system like the former mainly is present in prokaryotes. On the other hand, a multistep phosphate transfer is mainly seen in eukaryotes, and a receiver domain frequently attaches to the histidine kinase of such eukaryotes. A phosphate group transfer mediator is also involved in phosphate group transfer. The phosphorylation of the response regulator controls the activity of an output region which attaches to the response regulator. The output region is frequently a transcriptional regulator.

In the case of a cytokinin receptor of a plant, a receiver domain is present in the same molecule. In other words, in the case of a cytokinin receptor binding to cytokinin, it is known that autophosphorylation of a His residue in the molecule is followed by phoshoylate group transfer from the His residue to an Asp residue in the molecule. Then, it is found that the phosphate group transfers to an Asp residue of the response regulator via a His residue of the phosphate transfer mediator. For example, in the case of *Arabidopsis thaliana*, it is found that a phosphate group transfers from the cytokinin receptor CRE1, AHK2 or AHK3 to the response regulator via the phosphate group mediator AHP.

Examples of a gene encoding a cytokinin receptor that has been known before now include nucleotide sequences of genes derived from *Arabidopsis thaliana* (CRE1: accession No. AB049934, AHK2: accession No. AB046869, AHK3: accession No. AB046870), *Catharanthus roseus* (accession No. AY092025), *Oryza sativa* (accession No. AY572461), and *Zea mays* (ZmHK1: accession No. AB042270, ZmHK2: accession No. AB102956, ZmHK3a: accession No. AB102957, ZmHK3b: accession No. AB121445). Such a gene whose nucleotide sequence is known can be amplified by PCR using the genome DNA or cDNA of an organism having the desired gene as a template and primers which are produced on the basis of a nucleotide sequence corresponding to the vicinity of the amino terminal of a protein encoded by the gene and a nucleotide sequence corresponding to the vicinity of the carboxyl terminal thereof, and then isolated. A gene encoding a cytokinin receptor can also obtained from plants other than the above-described plants. First, mRNA is prepared from the desired plant, and cDNA is synthesized by using the mRNA as a template and a reverse transcriptase. The cDNA is incorporated into a phage vector such as ZAPII or a plasmid vector such as pUC to produce a cDNA library. Then, PCR is performed using the cDNA library as a template and primers which are designed and synthesized on the basis of well-conserved nucleotide sequences among genes whose nucleotide sequences are known as described above, and thereby a DNA fragment containing at least a part of a gene encoding a cytokinin receptor can be amplified. Then, the cDNA library is screened using the DNA fragment as a probe to select a positive clone. The DNA of the selected clone is sequenced, and it can be confirmed that the gene encodes the desired cytokinin receptor.

All of three kinds of cytokinin receptors (CRE1, AHK2, AHK3) of *Arabidopsis thaliana* are histidine kinases to which the receiver domain attaches in the same molecule. Amino acid sequence homology is high among these three cytokinin receptors, and particularly, there is high amino acid sequence homology among their extracellular domains that are thought to bind to cytokinin. Also, in the case of recombinant yeast as described hereinafter, all of the three kinds of cytokinin receptors initiated intracellular signaling in response to cytokinin, and could be confirmed to have the activity of a cytokinin receptor. Cytokinin receptors of the other plants are also histidine kinases, and their amino acid sequences have high homology with the amino acid sequences of the cytokinin receptors of *Arabidopsis thaliana*.

Table 1 shows amino acid sequence identity of other cytokinin receptors with the cytokinin receptor CRE1 of *Arabidopsis thaliana*.

A preferable example of the "plant-derived cytokinin receptor of a cell" includes a protein which consists of an amino acid sequence having a sequence identity of 45% or more, preferably 49% or more, more preferably 53% or more with the amino acid sequence of the cytokinin receptor CRE1 of *Arabidopsis thaliana* and has an activity of functioning as a cytokinin receptor.

TABLE 1

| | Amino acid sequence identity (%) with CRE1 |
|---|---|
| *A. thaliana* AHK2 | 53% |
| *A. thaliana* AHK3 | 54% |
| *Catharanthus roseus* | 52% |
| *Oryza sativa* | 49% |
| *Zea mays* ZmHK1 | 57% |
| *Zea mays* ZmHK2 | 51% |
| *Zea mays* ZmHK3a | 52% |
| *Zea mays* ZmHK3b | 49% |

The "intracellular signaling from a plant-derived cytokinin receptor of a cell" is the above-described signal transduction which is attained by phosphate group transfer starting from autophosphorylation of a cytokinin receptor binding to cytokinin. In a plant cell, a signal of cytokinin response is transmitted by autophosphorylation of a cytokinin receptor induced by binding of cytokinin, transfer of a phosphate group from the autophosphorylated cytokinin receptor to a phosphate group transfer mediator, and then transfer of the phosphate group from the phosphate group transfer mediator to a response regulator. Similarly, in a recombinant cell having a plant-derived cytokinin receptor, intracellular signaling from the cytokinin receptor is attained by transfer of a phosphate group. However, in this case, a phosphate group transfer mediator and a response regulator may be derived from a host cell. All of them may be derived from a host cell or some of them may be derived from a host cell. Moreover, a phosphate group transfer mediator may not exist. For example, in a recombinant budding yeast having a plant-derived cytokinin receptor, intracellular signaling from the cytokinin receptor is attained by transfer of a phosphate group from the cytokinin receptor autophosphorylated by binding of cytokinin to the response regulator Ssk1, which is a response regulator derived from the host budding yeast cell, via the phosphate group transfer mediator Ypd1, which is a phosphate group transfer mediator derived from the host budding yeast cell. In a recombinant fission yeast having a plant-derived cytokinin receptor, intracellular signaling from the cytokinin receptor is attained by transfer of a phosphate group to the response regulator Mcs4 derived from the host fission yeast, via the phosphate group transfer mediator Spy1 derived from the host fission yeast. In a recombinant *Escherichia coli* having a plant-derived cytokinin receptor, intracellular signaling from the cytokinin receptor is attained by transfer of a phosphate group to the response regulator RcsB derived from the host *Escherichia coli* via the phosphate group transfer mediator YojN derived from the host *Escherichia coli*.

An example of a method for determining the presence or absence or the amount of such intracellular signaling from a plant-derived cytokinin receptor includes a method which comprises determining the presence or absence or the amount of expression of a target gene whose transcription is controlled by a response regulator located downstream of the intracellular signaling from the plant-derived cytokinin receptor. This method includes a method comprising directly determining the presence or absence or the amount of expression of the target gene, as well as a method comprising transforming a host cell with a reporter plasmid in which a reporter gene such as a gene of a fluorescent protein or a gene of β-galactosidase is linked to a promoter region of the target gene, and then determining the presence or absence or the amount of expression of the reporter gene by using fluorescence or developed color as an indicator, and a method comprising measuring or observing an increase or decrease of the number of cells relating to expression of the target gene, a change in the characters of the cell, or the like. For example, in the case of the above-described recombinant budding yeast, the growth of the recombinant budding yeast dependent on cytokinin can be used as an indicator to determine the presence or absence or the amount of intracellular signaling from the plant-derived cytokinin receptor. In the case of the recombinant fission yeast, the size of the recombinant fission yeast dependent on cytokinin can be used as an indicator to determine the presence or absence or the amount of intracellular signaling from the plant-derived cytokinin receptor. In the case of the recombinant *Escherichia coli*, color developed due to expression of a β-galactosidase gene which is linked to a promoter region of the target gene cps can be used as an indicator to determine the presence or absence or the amount of intracellular signaling from the plant-derived cytokinin receptor. In the case of *Arabidopsis thaliana* transformed with a reporter plasmid in which a reporter gene is linked to a promoter region of the type-A response regulator ARR5 or ARR6. fluorescence or developed color dependent on cytokinin can be used as an indicator to determine the presence or absence or the amount of intracellular signaling from a cytokinin receptor. The above-described methods are described in, for example, Higuchi et al., Nature 409, 1060-1063 (2001); Suzuki et al., Plant Cell Physiol. 42, 107-113 (2001); Hwang and Sheen, Nature 413, 383-389 (2001), and so forth.

Among various methods for determining intracellular signaling from a plant-derived cytokinin receptor of a cell as described above, a preferable example as a mechanical, quantitative and efficient method is a method which comprises determining the growth of the recombinant budding yeast dependent on cytokinin by measuring turbidity of a liquid medium with a spectrophotometer. A specific example thereof includes the method described in JP-A 2003-079393.

The "activity of inhibiting intracellular signaling from a plant-derived cytokinin receptor of a cell" means the ability to reduce intracellular signaling from a plant-derived cytokinin receptor of a cell. In other words, this means the ability to reduce the amount of phosphate group transfer which is initiated by autophosphorylation of a cytokinin receptor and in which a phosphate group is transferred from the cytokinin receptor to a response regulator. Specific examples of the activity of inhibiting intracellular signaling from a plant-derived cytokinin receptor of a cell include the ability to inhibit the histidine kinase activity of a cytokinin receptor, the ability to inhibit phosphate group transfer from a cytokinin receptor to a phosphate group transfer mediator, the ability to inhibit phosphate group transfer from the phosphate group transfer mediator to a response regulator, and the ability to inhibit transcription control of the response regulator. More specifically, an example of the ability to inhibit the histidine kinase activity of a cytokinin receptor includes the ability to inhibit intracellular signaling from a cytokinin receptor by mechanism in which the presence or absence of inhibition of the intracellular signaling from the cytokinin receptor is determined depending on the presence or absence of inhibition of binding between a substance having a cytokinin agonistic activity and the cytokinin receptor, resulting in inhibition of the histidine kinase activity of the cytokinin receptor. In this case, as an example of a method for determining if a test substance actually inhibits the binding between a substance having a cytokinin agonistic activity and a cytokinin receptor includes a method comprising use of a radiolabeled substance having a cytokinin agonistic activity and a cytokinin receptor. For example, a substance having a cytokinin agonistic activity which is labeled with a radioisotope of hydrogen, tritium so as to become highly radioactive, and a cytokinin receptor protein prepared from a recombinant yeast into which a cytokinin receptor gene is introduced are allowed to coexist in a suitable buffer, and then the cytokinin receptor protein is collected on a glass filter to measure radioactivity. Thus the substance having a cytokinin agonistic activity which is labeled with tritium so as to become highly radioactive and which is binding to the cytokine receptor can be detected. When a test substance is also allowed to coexistent with the radiolabeled substance having a cytokinin agonistic activity and the cytokinin receptor protein in a buffer, it can be determined if the test substance inhibit the binding between the substance having a cytokinin agonistic activity and the cytokinin receptor by using a decrease in the measurement value of radioactivity as an indicator. Then, when the test substance is added to the above-described reaction system for determining the presence or absence or the amount of intracellular signaling from a plant-derived cytokinin receptor, influence of the test substance on the intracellular signaling from the plant-derived cytokinin receptor can be investigated.

The "agent which has an activity of inhibiting intracellular signaling from a plant-derived cytokinin receptor of a cell" means an agent comprising, as the active ingredient, a substance having an activity of inhibiting intracellular signaling from a plant-derived cytokinin receptor of a cell.

In the present invention, the "agent capable of controlling the growth or differentiation of a plant which has an activity of inhibiting intracellular signaling from a plant-derived cytokinin receptor of a cell" means an agent whose ability to inhibit intracellular signaling from a plant-derived cytokinin receptor of a cell is determined by the above-described method and which can control the growth or differentiation of a plant. The agent is desirably an agent in which the agent capable of controlling the growth or differentiation of a plant is a plant growth regulator.

In the present invention, the "plant growth regulator" is an agent capable of controlling the growth or differentiation of a plant.

An example of a method for determining the ability to control the growth or differentiation of a plant includes a method for determining a root growth-promoting activity in a plant as well as the methods disclosed in the present invention. Specifically, the ability to control the growth or differentiation of a plant can be determined, for example, according to the following method.

According to composition described below, an Enshi standard medium is prepared (see Table 2). A solution of a chemical substance in DMSO is dispensed in each 4 µl to cluster tubes so that the final concentration can be 0.001 ppm to 10 ppm. Then, 600 µl of the sterilized Enshi standard medium is added to each cluster tube, followed by mixing. In each tube, 10 to 20 seeds of *Arabidopsis thaliana* are put and cultured at 22° C. for 10 days in a bright place. Then the average length of main roots is measured. An average of eight repeats is determined and then a root growth rate is determined by the following equation.

TABLE 2

| Composition | | Concentration (mg/L) |
|---|---|---|
| Calcium nitrate | $Ca(NO_3)_2 \cdot 4H_2O$ | 950 |
| Potassium nitrate | $KNO_3$ | 810 |
| Magnesium sulfate | $MgSO_4 \cdot 7H_2O$ | 500 |
| Ammonium phosphate | $NH_4H_2PO_4$ | 155 |
| Chelate iron | Fe-EDTA | 22.62 |
| Boric acid | $H_3BO_3$ | 2.86 |
| Manganese sulfate | $MnSO_4 \cdot 4H_2O$ | 1.81 |
| Zinc sulfate | $ZnSO_4 \cdot 7H_2O$ | 0.22 |
| Copper sulfate | $CuSO_4 \cdot 5H_2O$ | 0.08 |
| Sodium molybdate | $Na_2MoO_4 \cdot 2H_2O$ | 0.025 |

Adjusted to pH 5.8

Root growth rate (%)=(Average main root length in chemical substance-treated section)/(Average main root length in control section)×100

It can be said that a test substance exhibiting a significantly high root growth rate has a root growth-promoting activity. More preferably, a test substance having a root growth rate of 120% or more can be judged to have a root growth-promoting activity.

The plant growth regulator in the present invention comprises a chemical substance capable of inhibiting intracellular signaling from a plant-derived cytokinin receptor of a cell, or an agriculturally acceptable salt thereof as an active ingredient.

In the present invention, the "agriculturally acceptable salt" means a salt in the form which does not make it impossible to produce a plant growth regulator and to apply the product, and may be a salt in any form. Specific examples of the salt include mineral acid salts such as hydrochloride, hydrobromide, hydroiodide, sulfate, nitrate and phosphate; organic acid salts such as formate, acetate, propionate, oxalate, malonate, succinate, fumarate, maleate, lactate, malate, tartrate, citrate, methanesulfonate and ethanesulfonate; acid addition salts, for example, acidic amino acid salts such as aspartate and glutamate; metal salts such as alkali metal salts (sodium salt, potassium salt, etc.), alkali earth metal salts (magnesium salt, etc.), and aluminum salts; addition salts of organic bases such as methylamine, ethylamine and ethanolamine and of basic amino acids such as lysine and ornithine; and ammonium salts.

The plant growth regulator is usually used in the form of a formulation such as an emulsifiable concentrate, a wettable powder, a suspension or a water soluble powder which is obtainable by mixing with a solid carrier, a liquid carrier or the like and, if necessary, adding (a) surfactant(s) and other formulation auxiliaries thereto. The formulation contains usually 0.5 to 90% by weight, preferably 1 to 80% by weight of a substance capable of inhibiting cytokanin signaling.

Examples of the solid carrier used for formulation include fine powders and granules of clays (kaolinite, diatomaceous earth, synthetic hydrous silicon oxide, Fubasami clay, bentonite, acid clay, etc.), talc, other inorganic minerals (sericite, quarts powder, sulfur powder, activated carbon, calcium carbonate, etc.) and chemical fertilizers (ammonium sulfate, ammonium phosphate, ammonium nitrate, ammonium chloride, urea, etc.). Examples of the liquid carrier include water, alcohols (methanol, ethanol, etc.), ketones (acetone, methyl ethyl ketone, cyclohexanone, etc.), aromatic hydrocarbons (toluene, xylene, ethylbenzene, methylnaphthalene, etc.), non-aromatic hydrocarbons (hexane, cyclohexane, kerosene, etc.), esters (ethyl acetate, butyl acetate, etc.), nitriles (acetonitrile, isobutyronitrile, etc.), ethers (dioxane, diisopropyl ether, etc.), acid amides (dimethylformamide, dimethylacetamide, etc.) and halogenated hydrocarbons (dichloroethane, trichloroethylene, etc.).

Examples of the surfactant include alkyl sulfates, alkyl sulfonates, alkyl aryl sulfonates, alkyl aryl ethers and their polyoxyethylene compounds, polyethylene glycol ethers, polyhydric alcohol esters, and sugar alcohol derivatives.

Examples of other formulation auxiliaries include sticking agents and dispersing agents such as casein, gelatin, polysaccharides (starch, gum Arabic, cellulose derivatives, alginic acid, etc.), lignin derivatives, bentonite, synthetic water-soluble polymers (polyvinyl alcohol, polyvinyl pyrrolidone, polyacrylic acid, etc.), and stabilizing agents such as PAP (acidic isopropyl phosphate), BHT (2,6-tert-butyl-4-methylphenol), BHA (2-/3-tert-butyl-4-methoxyphenol), vegetable oils, mineral oils, fatty acids and fatty acid esters.

In the present invention, the "plant growth regulator comprising a chemical substance capable of inhibiting intracellular signaling from a plant-derived cytokinin receptor of a cell, or an agriculturally acceptable salt thereof, as an active ingredient" is an agent which can control the growth or differentiation of a plant by containing, as an active ingredient, a chemical substance whose ability to inhibit intracellular signaling from a plant-derived cytokinin receptor of a cell is determined by the above-described method or an agriculturally acceptable salt of the chemical substance. The chemical substance is desirably a chemical substance having the ability to inhibit intracellular signaling from a cytokinin receptor in a contact system of the above-described recombinant budding yeast which comprises a cytokinin receptor and a substance having an agonistic activity for the cytokinin receptor. More desirably, an example of the chemical substance includes a chemical substance having the ability to inhibit the activity of a cytokinin receptor in a contact system of the above-described recombinant budding yeast which comprises a cytokinin receptor and a substance having an agonistic activity for the cytokinin receptor, so that the activity of the cytokinin receptor can be reduced in the presence of 0.6 ppm of trans-zeatine and 2 ppm or more of the chemical substance as compared with the case in the absence of the chemical substance. Still more desirably, an example of the chemical substance includes a chemical substance having the ability to inhibit the activity of a cytokinin receptor in a contact system of the above-described recombinant budding yeast which comprises a cytokinin receptor and a substance having an agonistic activity for the cytokinin receptor, so that the activity of the cytokinin receptor can be reduced by 90% or more in the presence of 0.6 ppm of trans-zeatine and 2 ppm or more of the chemical substance as compared with the case in the absence of the chemical substance.

In the present invention, a "method for testing the ability of a test substance to promote the growth of a root of a plant, which comprises:

(1) a first step of measuring an activity of inhibiting intracellular signaling from a cytokinin receptor selected from the following group A (or the presence or absence or the amount of the intracellular signaling) in a contact system comprising a cell having the cytokinin receptor, a substance having an agonistic activity to the cytokinin receptor and the test substance; and (2) a second step of evaluating the ability of the test substance to promote the growth of a root of a plant on the basis of a difference obtained by comparing the activity measured in the first step with the activity in control" is a method comprising the first step and the second step among various methods for testing the ability to promote the growth of a root of a plant of a test substance.

The "Group A" represents as follows:
(a) a protein comprising the amino acid sequence of SEQ ID NO:1,
(b) a protein comprising an amino acid sequence of SEQ ID NO:1 in which one or more amino acids are deleted, added or substituted, and having an activity of functioning as a cytokinin receptor,
(c) a protein comprising an amino acid sequence having a sequence identity of 45% or more with the amino acid sequence of SEQ ID NO:1, and having an activity of functioning as a cytokinin receptor
(d) a protein comprising an amino acid sequence encoded by the nucleotide sequence of SEQ ID NO:2
(e) a protein comprising an amino acid sequence encoded by a polynucleotide that hybridizes under a stringent condition with a polynucleotide complementary to a polynucleotide having the nucleotide sequence of SEQ ID NO:2, and having an activity of functioning as a cytokinin receptor.

The first step is a step of measuring an activity of inhibiting intracellular signaling from the cytokinin receptor (or the presence or absence or the amount of the intracellular signaling) in a contact system comprising a cell having the above-described various cytokinin receptors, a substance having an agonistic activity to the cytokinin receptor and the test substance. The second step is a step of evaluating the ability of the test substance to promote the growth of a root of a plant on the basis of a difference obtained by comparing the activity measured in the first step with the activity in control. As used herein, for example in the case where a solution of a test substance in a solvent is added to a reaction system, the control means a test in which only the solvent is added.

The plant-derived cytokinin receptor of a cell used in the method for testing the ability of a test substance to promote the growth of a root of a plant which comprises the first step and the second step is a protein shown in the above-described group A. Among the proteins of the above-described group A, in the amino acid sequences of proteins shown in (b), (c), (d) and (e), differences from the amino acid sequence of (a) that may be occasionally found are due to deletion, substitution, addition, and the like of some amino acids. The differences include deletion caused by processing which a protein having the amino acid sequence of (a) undergoes in cells. Moreover, the differences include deletion, substitution, addition, and the like of amino acids caused by naturally occurring genetic mutation due to species difference, individual difference or the like of organisms from which the protein is derived, or genetic mutation artificially introduced by site-directed mutagenesis, random mutagenesis, mutagenesis treatment or the like.

The number of such amino acid deletion, substitution, addition or the like may be within the range in which the histidine kinase activity of a cytokinin receptor can be found. Examples of the amino acid substitution include substitutions with amino acids having analogous characteristics such as hydrophobicity, charge, pK and space structure. Specific examples of such substitution include substitutions within the groups of (1) glycine, alanine; (2) valine, isoleucine, leucine; (3) aspartic acid, glutamic acid, asparagine, glutamine; (4) serine, threonine; (5) lysine, arginine; (6) phenylalanine, tyrosine; and the like.

An example of a method for artificially performing such deletion, addition or substitution of amino acid (hereinafter, occasionally referred to as alternation of amino acid, in general) includes a method which comprises subjecting DNA encoding the amino acid sequence of (a) to site-specific mutagenesis and then expressing the DNA by a conventional technique. Examples of the site-specific mutagenesis method include a method comprising use of amber mutation (gapped duplex method, Nucleic Acids Res., 12, 9441-9456 (1984)), and a method comprising PCR using primers for introducing mutation. An example of a method for artificially performing alternation of amino acid includes a method which comprises subjecting DNA encoding the amino acid sequence of (a) to random mutagenesis and then expressing the DNA by a conventional method. An example of a method for random mutagenesis includes a method comprising PCR using DNA coding any one of the above-described amino acid sequences as a template and using a primer pair by which the full length of DNA can be amplified, in a reaction condition that the addition concentration of each of dATP, dTTP, dGTP and dCTP used as substrates is changed from the usual condition or in a reaction condition that the concentration of $Mg^{2+}$ for promoting polymerase reaction is increased from the general condition. Example of such a PCR technique include a method described in Method in Molecular Biology, (31), 1994, 97-112, as well as a method described in WO0009682.

As used herein, the "sequence identity" means identity between two nucleotide sequences or two amino acid sequences. The "sequence identity" is determined by comparing two optimally aligned sequences over their all regions. The optimal alignment of the nucleotide sequences or the amino acid sequences may contain addition or deletion (for example, gap). Such sequence identity can be calculated by performing homology analysis using programs such as FASTA [Pearson & Lipman, Proc Natl Acad Sci. USA, 4, 2444-2448 (1988)], BLAST [Altschul et al., Journal of Molecular Biology, 215, 403-410 (1990)], and CLUSTAL W [Thompson, Higgins & Gibson, Nucleic Acid Research, 22, 4673-4680 (1994a)] to construct alignments. The above-described programs are generally available in the homepage (http://www.ddbj.nig.ac.jp) of DNA Data Bank of Japan [international DNA data bank operated in Center for Information Biology and DNA Data Bank of Japan; CIB/DDBJ of National Institute of Genetics] or the like. The sequence identity can also be obtained by using commercially available sequence analysis software. Specifically, for example, homology analysis is performed by Lipman-Pearson method [Lipman, D. J. and Pearson, W. R., Science, 227, 1435-1441, (1985)] and using GENETYX-WIN Ver.5 (manufactured by Software Development Co., Ltd.) to construct alignments, and thereby, sequence identity can be calculated.

The "stringent condition" described in (e) includes such a condition that hybridization is performed at 45° C. in a solution containing 6×SSC (10×SSC contains 1.5M NaCl and 0.15M trisodium citrate) followed by washing with 2×SSC at 50° C. (Molecular Biology, John Wiley & Sons, N.Y. (1989), 6.3.1-6.3.6), in hybridization performed according to a conventional method, for example, as described in Molecular Cloning 2nd edition written by Sambrook J., Frisch E. F., Maniatis T. issued by Cold Spring Harbor Laboratory Press. The salt concentration in the washing step can be selected from, for example, the range of 2×SSC (low stringent condition) to 0.2×SSC (high stringent condition). The temperature in the washing step can be selected from, for example, the range of room temperature (low stringent condition) to 65° C. (high stringent condition). Both the salt concentration and the temperature can be changed.

Each of these proteins is a protein having an activity functioning as a cytokinin receptor. Desirably, the following protein is used: a protein comprising an amino acid sequence wherein amino acid residues corresponding to the positions (I) 459 and (II) 973 of SEQ ID NO: 1 are respectively (I) histidine at position 459 and (II) aspartic acid at position 973, when the amino acid sequence of the protein is aligned with the amino acid sequence of SEQ ID NO: 1 so that the maximum sequence identity can be obtained. As used herein, "the amino acid sequence of the protein is aligned with the amino acid sequence of SEQ ID NO: 1 so that the maximum sequence identity can be obtained" means that sequence identity analysis of plural amino acid sequences of interest including the amino acid sequence of SEQ ID NO: 1 is performed by using the above-described program such as FASTA, BLAST, or CLUSTAL W to align the amino acid sequences. As a result of alignment of plural sequences by such a method, it is possible to determine the positions of homologous amino acid residues in each of the amino acid sequences despite insertion or deletion existing in the amino acid sequences. The homologous positions are thought to be the same position in three-dimensional structure, and can be estimated to have analogous effects for the specific function of the protein of interest. For example, in the case of known cytokinin receptors including the cytokinin receptor whose sequence is disclosed in the present invention, amino acid residues corresponding to the positions (I) 459 and (II) 973 of SEQ ID NO: 1 are respectively (I) histidine at position 459 and (II) aspartic acid at position 973, when the amino acid sequence of the cytokinin receptor is aligned with the amino acid sequence of SEQ ID NO: 1 so that the maximum sequence identity can be obtained.

The active ingredient of the agent capable of controlling the growth or differentiation of a plant can be searched, for example, by determining the ability to promote the growth of a root of the plant.

The method for testing the ability to promote the growth of a root of a plant which comprises using a plant-derived cytokinin receptor of a cell as described above can be also used to search a substance having the ability to control the growth or differentiation of a plant. Specifically, when the ability of a test substance to promote the growth of a root of a plant is determined to be a certain value or more or a certain value or less by using the method for testing the ability to promote the growth of a root of a plant which comprises using a plant-derived cytokinin receptor of a cell, the substance is selected. Thus, a substance having the ability to promote the growth of a root of a plant can be searched.

Because a substance selected by the searching method has the ability to control the growth or differentiation of a plant, a composition containing the substance or an agriculturally acceptable salt thereof as an active ingredient can be a plant growth regulator.

Specific examples of the substance capable of inhibiting cytokinin signaling include cytokinin antagonists, and cytokinin agonists.

The cytokinin signaling-inhibiting substance selected by the above-described searching method may promote the growth of a root of a plant. The growth of a root includes elongation of the main root, elongation of a lateral root, and elongation of root hair.

The root growth-promoting activity of the cytokinin signaling-inhibiting substance selected by the above-described searching method can be tested by using, for example, the following method. For example, aqueous solutions, hydroponic culture media or tissue culture media containing the cytokinin signaling-inhibiting substance at different concentrations within the range of 0.0001 to 100 ppm are prepared depending on the kind of a plant and an assay method. In the case of a petri dish test, a filter paper spread on a petri dish is impregnated with the solution, and plant seeds are put thereon. In the case of a pouch test, a heavy paper is impregnated with the solution, wherein the heavy paper is placed in a pouch which allows for observation of root growth such as a pouch for seed growth, and plant seeds are sowed thereon. A solid medium is prepared by adding agarose, agar or the like to the solution in a plastic petri dish or a plastic centrifuge tube, and plant seeds are sowed therein. After incubation for a certain period at 10 to 30° C. in the light, the lengths of the main root and lateral roots, the number of lateral roots, the wet weight of the root, the dry weight of the root, and so forth are measured.

The cytokinin signaling-inhibiting substance selected by the above-described searching method may be used as a plant growth regulator.

In groups represented by R, X, $R^1$, $R^2$, $R^3$, $R^4$, $R^5$, $R^6$ and $R^7$ in the compound represented by the general formula (I) used in the present invention (hereinafter, sometimes, referred to as the compound (I)), examples of the "hydrocarbon group" include an aliphatic hydrocarbon group, a monocyclic saturated hydrocarbon group and an aromatic hydrocarbon group, and a hydrocarbon group having 1 to 16 carbon atoms is preferred. Specific examples thereof include an alkyl group, an alkenyl group, an alkynyl group, a cycloalkyl group, an aralkyl group and an aryl group.

The "alkyl group" is preferably, for example, a lower alkyl group. Specific examples of the alkyl group include C1-6 alkyl groups such as methyl, ethyl, propyl, isopropyl, butyl, isobutyl, sec-butyl and tert-butyl, pentyl and hexyl.

The "alkenyl group" is preferably, for example, a lower alkenyl group. Specific examples of the alkenyl group include C2-6 alkenyl groups such as vinyl, 1-propenyl, allyl, isopropenyl, butenyl and isobutenyl.

The "alkynyl group" is preferably, for example, a lower alkynyl group. Specific examples of the alkynyl group include C2-6 alkynyl groups such as ethynyl, propargyl and 1-propynyl.

The "cycloalkyl group" is preferably, for example, a lower cycloalkyl group. Specific examples of the cycloalkyl group include C3-6 cycloalkyl groups such as cyclopropyl, cyclobutyl, cyclopentyl and cyclohexyl. The "aralkyl group" is preferably, for example, a C7-11 aralkyl group such as benzyl or phenethyl. Specifically, for example, a benzyl group is used.

The "aryl group" is preferably, for example, a C6-14 aryl group such as phenyl, 1-naphthyl, 2-naphthyl, biphenylyl or 2-anthryl. Specifically, for example, a phenyl group is used.

Examples of a substituent for the "hydrocarbon group" and the "C1-6 alkyl group" of the "optionally substituted hydrocarbon group" and the "optionally substituted C1-6 alkyl group" include a halogen atom (for example, fluorine, chlorine, bromine, iodine, etc.), a nitro group, a cyano group, a hydroxyl group, a lower alkyl group (for example, a C1-6 alkyl group such as methyl, ethyl, propyl, isopropyl, butyl, isobutyl, sec-butyl, tert-butyl, pentyl, isopentyl, neopentyl, or hexyl, etc.), a lower alkoxy group (for example, a C1-6 alkoxy group such as methoxy, ethoxy, propoxy, isopropoxy, butoxy, isobutoxy, pentyloxy or hexyloxy, etc.), an amino group, a mono-lower alkylamino group (for example, a mono-C1-6 alkylamino group such as methylamino or ethylamino, etc.), a di-lower alkylamino group (for example, a di-C1-6 alkylamino group such as dimethylamino or diethylamino, etc.), an imino group, a carboxyl group, a lower alkylcarbonyl group (for example, a C1-6 alkylcarbonyl group such as acetyl or propionyl, etc.), a lower alkoxycarbonyl group (for example, a C1-6 alkoxycarbonyl group such as methoxycarbonyl, ethoxycarbonyl, propoxycarbonyl or butoxycarbonyl, etc.), a carbamoyl group, a thiocarbamoyl group, a mono-lower alkylcarbamoyl group (for example, a mono-C1-6 alkylcarbamoyl group such as methylcarbamoyl or ethylcarbamoyl, etc.), a di-lower alkylcarbamoyl group (for example, a di-C1-6 alkylcarbamoyl group such as dimethylcarbamoyl or diethylcarbamoyl, etc.), an arylcarbamoyl group (for example, a C6-10 arylcarbamoyl group such as phenylcarbamoyl or naphthylcarbamoyl, etc.), an aryl group (for example, a C6-10 aryl group such as phenyl or naphthyl, etc.), an aryloxy group (for example, a C6-10 aryloxy group such as phenyloxy or naphthyloxy, etc.), a heterocyclic group (for example, 2- or 3-thienyl, 2- or 3-tetrahydrothienyl, 2- or 3-furyl, 2- or 3-tetrahydrofuryl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 4- or 5-1H-1,2,3-triazolyl, 3- or 5-1,2,4-triazolyl, 5-1H- or 5-2H-tetrazolyl, 2-, 3- or 4-pyridyl, 2-, 4- or 5-pyrimidinyl, 1-, 2- or 3-thiomorpholinyl, 1-, 2- or 3-morpholinyl, 1-, 2-, 3- or 4-piperidino, 2-, 3- or 4-piperidyl, 2-, 3- or 4-thiopyranyl, 2-, 3- or 4-4H-1,4-oxadinyl, 2-, 3- or 4-4H-1,4-thiazinyl, 1,3-thiazinyl, 1- or 2-piperazinyl, 3-, 5- or 6-1,2,4-triazinyl, 2-1,3,5-triazinyl, 3- or 4-pyridazinyl, 2-pyrazinyl, etc.), a lower alkylcarbonylamino group (for example, a C1-6 alkylcarbonylamino group such as acetylamino, etc.), a mercapto group, a C1-6 alkylthio group (for example, a C1-6 alkylthio group such as methylthio, etc.), an alkylsulfinyl group (for example, a C1-6 alkylsulfinyl group such as methylsulfinyl, etc.), an alkylsulfonyl group (for example, a C1-6 alkylsulfonyl group such as methylsulfonyl, etc.), an arylthio group (for example, a C6-10 arylthio group such as phenylthio, etc.), an arylsulfinyl group (for example, a C6-10 arylsulfinyl group such as phenylsulfinyl, etc.), an arylsulfonyl group (for example, a C6-10 arylsulfonyl group such as phenylsulfonyl, etc.), an oxo group and a thioxo group.

The acyl group (for example, formyl, acetyl, propionyl, pivaloyl, acryloyl, benzoyl, etc.) is a kind of a hydrocarbon group substituted with an oxo group and is included in the "optionally substituted hydrocarbon group" and the "optionally substituted C1-6 alkyl group".

The "hydrocarbon group" and the "C1-6 alkyl group" of the "optionally substituted hydrocarbon group" and the "optionally substituted C1-6 alkyl group" may have 1 or more, preferably 1 to 3 of the above-described substituents at substitutable positions When the substituent is a halogen atom, the hydrocarbon group and the C1-6 alkyl group may have the substitutable maximum number of substituents. When they have 2 or more substituents, the substituents are the same or different.

When the substituent is a lower alkyl group, a lower alkoxy group, a mono-lower alkylamino group, a di-lower alkylamino group, a lower alkylcarbonyl group, a lower alkoxycarbonyl group, a mono-lower alkylcarbamoyl group, a di-lower alkylcarbamoyl group, an arylcarbamoyl group, an aryl group, an aryloxy group, a heterocyclic group, a lower alkylcarbonylamino group, an alkylthio group, an alkylsulfinyl group, an alkylsulfonyl group, an arylthio group, an arylsulfinyl group, an arylsulfonyl group or the like, the substituent is optionally substituted with 1 to 3 substituents selected from the group consisting of a halogen atom (for example, fluorine, chlorine, bromine, iodine, etc.), a nitro group, a cyano group, a hydroxyl group, a C1-4 alkoxy group (for example, methoxy, ethoxy, propoxy, isopropyloxy, butoxy, isobutyloxy), an aryl group, an oxo group and the like. When the substitute is an arylcarbamoyl group, an aryl group, an aryloxy group, a heterocyclic group, a C6-10 arylthio group, a C6-10 arylsulfinyl group, a C6-10 arylsulfonyl group or the like, the substituent is optionally substituted with one to three C1-4 alkyl groups (for example, methyl, ethyl, propyl, isopropyl, butyl, isobutyl, sec-butyl, tert-butyl, etc.).

Examples of the "C1-6 alkyl group" include methyl, ethyl, propyl, isopropyl, butyl, isobutyl, sec-butyl and tert-butyl, pentyl, and hexyl.

Examples of the "C1-3 alkyl group" (including the C1-3 alkyl group contained in a C1-3 alkylamino group and a di C1-3 alkylamino group) include methyl, ethyl, propyl and isopropyl.

Examples of the "C3-6 alkenyl group" include 1-propenyl, allyl, isopropenyl, butenyl and isobutenyl.

Examples of the "C3-6 alkynyl group" include propargyl and 1-propynyl.

Examples of the "C1-3 alkoxy group" (including the C1-3 alkyl group contained in a hydroxy C1-3 alkoxy group and a C1-3 alkoxycarbonyl group) include methoxy, ethoxy, propoxy and isopropyloxy.

Examples of the "C1-3 acyl group" (including the C1-3 acyl group contained in a C1-3 acylthio group) include formyl, acetyl and propionyl.

Examples of the "C1-3 haloalkyl group" include chloromethyl, trifluoromethyl, 2-bromoethyl, 2,2,2-trifluoroethyl and 2,2,3,3,3-pentafluoropropyl.

Examples of the "cyclic amino group" of the "$R^1$ and $R^2$ are taken together with the nitrogen atom to which they are attached to form an optionally substituted cyclic amino group" include 1-aziridinyl, pyrrolidino, piperidino, morpholino and thiomorpholino. Examples of a substituent for the "cyclic amino group" include 1 to 3 of substituents described above such as a C1-3 alkyl group, a C1-3 alkoxy group and a hydroxyl group.

Examples of the "aryl group" in the groups represented by Ar include aryl groups described as examples of the "hydrocarbon group" represented by R, X, $R^1$, $R^2$, $R^3$, $R^4$, $R^5$, $R^6$ and $R^7$.

Examples of the "heteroaryl group" in the groups represented by Ar include 2- or 3-thienyl, 2- or 3-furyl, 1-, 2- or 3-pyrrolyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 4- or 5-imidazolyl, 4- or 5-1H-1,2,3-triazolyl, 3- or 5-1,2,4-triazolyl, 5-1H- or 5-2H-tetrazolyl, 2-, 3- or 4-pyridyl, 2-, 4- or 5-pyrimidinyl, 1- or 2-piperazinyl, 3-, 5- or 6-1,2,4-triazinyl, 2-1,3,5-triazinyl, 3- or 4-pyridazinyl, and 2-pyrazinyl.

Examples of a substituent for the "aryl group" and the "heteroaryl group" include groups described as examples of a substituent for the "optionally substituted hydrocarbon group" and the "optionally substituted C1-6 alkyl group" represented by R, X, $R^1$, $R^2$, $R^3$, $R^4$, $R^5$, $R^6$ and $R^7$.

The compound of the general formula (I) in which l is 0 is the compound in which the 2-position of the quinazoline skeleton is unsubstituted, that is, a compound of the general formula (I-1):

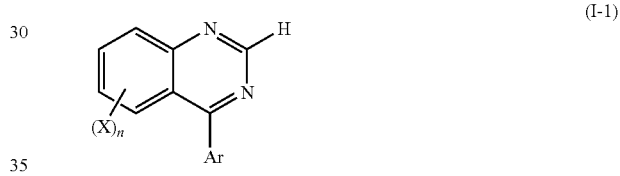

wherein X represents an optionally substituted hydrocarbon group, a group represented by $NR^1R^2$, a group represented by $OR^3$, a group represented by $S(O)_mR^4$, a nitro group or a halogen atom, in which $R^1$ represents a hydrogen atom or an optionally substituted hydrocarbon group, $R^2$ represents a hydrogen atom, an optionally substituted hydrocarbon group, a group represented by $NR^5R^6$ (in which $R^5$ and $R^6$ are the same or different and represent a hydrogen atom or an optionally substituted C1-6 alkyl group) or a group represented by $OR^7$ (in which $R^7$ represents a hydrogen atom or an optionally substituted C1-6 alkyl group), or $R^1$ and $R^2$ are taken together with the nitrogen atom to which they are attached to form an optionally substituted cyclic amino group, $R^3$ and $R^4$ each represent an optionally substituted hydrocarbon group, m represents an integer of 0 to 2, n represents an integer of 0 to 4, when n is 2 or more, each X is the same or different from each other, and Ar represents an optionally substituted aryl group or an optionally substituted heteroaryl group.

The compound of the general formula (I) in which l is 1 is the compound in which the 2-position of the quinazoline skeleton is substituted with R, that is, a compound of the general formula (I-2):

(I-2)

wherein R and X are the same or different and represent optionally substituted hydrocarbon group, a group represented by NR$^1$R$^2$, a group represented by OR$^3$, a group represented by S(O)$_m$R$^4$, a nitro group or a halogen atom, in which R$^1$ represents a hydrogen atom or an optionally substituted hydrocarbon group, R$^2$ represents a hydrogen atom, an optionally substituted hydrocarbon group, a group represented by NR$^5$R$^6$ (in which R$^5$ and R$^6$ are the same or different and represent a hydrogen atom or an optionally substituted C1-6 alkyl group) or a group represented by OR$^7$ (in which R$^7$ represents a hydrogen atom or an optionally substituted C1-6 alkyl group), or R$^1$ and R$^2$ are taken together with the nitrogen atom to which they are attached to form an optionally substituted cyclic amino group, R$^3$ and R$^4$ each represent an optionally substituted hydrocarbon group, m represents an integer of 0 to 2, n represents an integer of 0 to 4, when n is 2 or more, each X is the same or different from each other, and Ar represents an optionally substituted aryl group or an optionally substituted heteroaryl group.

The compound (I) may be in the form of the above-described "agriculturally acceptable salt".

When the compound (I) has one or more asymmetric centers, the compound includes two or more stereoisomers (for example, enantiomer, diastereomer, etc.). The compound of the present invention includes all stereoisomers and a mixture of two or more stereoisomers.

When the compound (I) has geometrical isomerism based on a double bond and the like, the compound (I) includes two or more geometrical isomers (for example, E/Z or trans/cis isomers, S-trans/S-cis isomers, etc.). The compound (I) includes all geometrical isomers and a mixture of two or more geometrical isomers.

Preferable examples of the compound (I) include the following compounds.

(1) A compound of the general formula (I), wherein l is 1 and R is an optionally substituted hydrocarbon group.

(2) A compound of the general formula (I), wherein l is 1 and R is a C1-3 alkyl group which is optionally substituted with (a) halogen atom(s) or (an) oxo group(s).

(3) A compound of the general formula (I), wherein the optionally substituted hydrocarbon group is a C1-3 alkyl group which is optionally substituted with (a) halogen atom(s) or an (oxo) groups.

(4) A compound of the general formula (I), wherein l is 1 and R is a group represented by NR$^1$R$^2$.

(5) A compound of the above (4), wherein R$^1$ represents a hydrogen atom or a C1-3 alkyl group, R$^2$ represents a hydrogen atom, an amino group, a C1-3 alkylamino group, a di C1-3 alkylamino group, an amidino group, a C1-3 alkoxy group, a phenyl group, a C1-3 acyl group, a C1-6 alkyl group, a C3-6 alkenyl group or a C3-6 alkynyl group, in which the phenyl group is optionally substituted with the same or different one to three C1-3 alkyl groups, and the phenyl group, the acyl group, the alkyl group, the alkenyl group and the alkynyl group are optionally substituted with the same or different 1 to 3 substituents selected from the group consisting of a halogen atom, a hydroxyl group, a C1-3 alkoxy group, a hydroxy C1-3 alkoxy group, a carboxyl group, a C1-3 alkoxycarbonyl group, a carbamoyl group, an amino group, a C1-3 alkylamino group, a di C1-3 alkylamino group, a mercapto group; a C1-3 acylthio group, a cyano group, a furyl group and a tetrahydrofuryl group, or R$^1$ and R$^2$ are taken together with the nitrogen atom to which they are attached to form a pyrrolidino group, a piperidino group or a morpholino group.

(6) A compound of the above (4), wherein R$^1$ represents a hydrogen atom, R$^2$ represents a hydrogen atom, a formyl group, a C1-6 alkyl group, a C3-6 alkenyl group or a C3-6 alkynyl group, in which the alkyl group, the alkenyl group and the alkynyl group are optionally substituted with (a) substituent(s) selected from the group consisting of a hydroxyl group, a methoxy group, a methoxycarbonyl group, an ethoxycarbonyl group, a cyano group and a furyl group.

(7) A compound of the general formula (I), wherein l is 1 and R is a group represented by OR$^3$.

(8) A compound of the above (7), wherein R$^3$ is a C1-3 alkyl group which is optionally substituted with an amino group.

(9) A compound of the general formula (I), wherein l is 1 and R is a group represented by S(O)$_m$R$^4$.

(10) A compound of the above (9), wherein R$^4$ is a C1-3 alkyl group which is optionally substituted with an amino group or a hydroxyl group, and m is 0.

(11) A compound of the general formula (I), wherein l is 1 and R is a halogen atom.

(12) A compound of the above (11), wherein the halogen atom is a chlorine atom.

(13) A compound of the general formula (I), wherein n is from 1 to 2 and X is a C1-3 alkyl group, a C1-3 alkoxy group, a C1-3 haloalkyl group, a cyano group, a halogen atom or a nitro group.

(14) A compound of the above (13), wherein X is a chlorine atom, a bromine atom or a nitro group, and X is substituted at the 6-position and/or the 8-position.

(15) A compound of the general formula (I), wherein Ar is a phenyl group which is optionally substituted with (a) halogen atom(s) or (a) C1-3 alkyl group(s).

The compound (I) includes known compounds and can be prepared by a known method or a method analogous thereto.

For example, a compound (Ia) in which l is 1 and R is a chlorine atom can be prepared by heating a compound (II) with phosphorus oxychloride according to the following production process 1.

Document Example: JP-A 62-145073

Production Process 1

(II) + POCl$_3$ ⟶

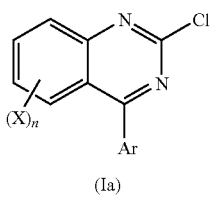

(Ia)

wherein symbols are as defined above.

The reaction may be carried out in a solvent which does not adversely affect the reaction, and is usually carried out in the absence of a solvent and using an excess amount of phosphorus oxychloride (5 equivalents to 30 equivalents based on the compound (II)). The reaction temperature is usually from 80 to 200° C., preferably from 90° C. to the reflux temperature (105° C.). The reaction time is usually from 0.1 to 96 hours, preferably from 0.5 to 5 hours, more preferably 0.5 to 2 hours. When the reaction proceeds slowly even under reflux, the reaction can also be heated to about 200° C. and pressurized (for example, at 1.1 to 100 atmospheric pressure) in a pressure-resistant closed vessel.

A compound (Ib) wherein l is 1 and R is a group $R^a$ which is other than a halogen atom can be prepared, for example, by reacting a compound (III) with a compound (IV) according to the following production process 2.

Document Example: Journal of the Chemical Society of Japan, 1973, p 1944; JP-A 58-88369

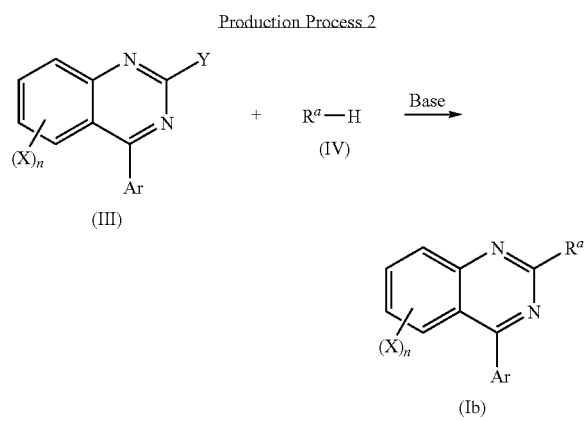

wherein Y represents a leaving group (for example, a halogen atom such as fluorine, chlorine, bromine or iodine; an alkane- or arene-sulfonyloxy group such as a methanesulfonyloxy group, a benzenesulfonyloxy group or a p-toluenesulfonyloxy group; an alkane-, arene- or arenealkane-sulfonyl group such as methanesulfonyl, benzenesulfonyl, or phenylmethanesulfonyl, etc.); $R^a$ has the same meaning as that of R, provided that $R^a$ is not a halogen atom; and other symbols are as defined above.

The reaction may be carried out with or without using a solvent. Examples of the solvent include aliphatic hydrocarbon such as pentane, hexane, heptane, petroleum ether, or cyclohexane; ester such as methyl acetate, ethyl acetate, ethyl formate, or ethyl propionate; ketone such as acetone, or methyl ethyl ketone; ether such as diethyl ether, methyl tert-butyl ether, diisopropyl ether, dibutyl ether, tetrahydrofuran, or dioxane; alcohol such as methanol, ethanol, or isopropanol; nitrile such as acetonitrile, or propionitrile; acid amide such as dimethylformamide, or dimethylacetamide; cyclic amide such as 1-methyl-2-pyrrolidone; phosphoric amide such as hexamethylphosphoramide; cyclic urea such as 1,3-dimethyl-2-imidazolidinone; sulfoxide such as dimethyl sulfoxide; sulfone such as sulfolane; halogenated hydrocarbon such as dichloromethane, chloroform, 1,2-dichloroethane, or carbon tetrachloride; aromatic amine such as pyridine, picoline, lutidine, or quinoline; their mixtures, water, and mixtures of the solvents and water.

When a mixture of the solvent and water is used and the reaction is not a homogeneous reaction system, a phase transfer catalyst (for example, a quaternary ammonium salt such as benzyltriethylammonium chloride, or benzyltriethylammonium bromide, crown ether such as 18-crown-6, etc.) may be used.

Examples of the base include alkali metal alcoholate such as sodium ethylate, sodium methylate, or potassium tert-butoxide; an organic base such as pyridine, picoline, lutidine, quinoline, triethylamine, diisopropylethylamine, 4-dimethylaminopyridine, or N,N-dimethylaniline; an inorganic base such as potassium carbonate, sodium carbonate, sodium hydroxide, potassium hydroxide, sodium hydrogen carbonate, or potassium hydrogen carbonate; metal hydride such as lithium hydride, sodium hydride, or potassium hydride; and an organic lithium reagent such as butyl lithium, or lithium diisopropylamide.

The amount of the base to be used is not particularly limited as long as it does not adversely influence the reaction. A large excess amount of the base can also be used as a solvent.

When the compound (IV) is an amine, an excess amount of the compound (IV) can also be used as both a base and a solvent.

The reaction temperature is usually from −50 to 200° C. preferably from room temperature to 150° C. The reaction time is usually from 0.1 to 96 hours, preferably from 0.1 to 72 hours, more preferably from 0.1 to 24 hours.

When the compound (IV) is a low boiling point-compound such as ammonia, methylamine or ethylamine or when the reaction proceeds slowly, the reaction can also be heated to a temperature of about 40 to 150° C. and pressurized (for example, at 1.1 to 100 atmospheric pressure) in a pressure-resistant closed vessel.

The compound (II) includes a known compound and can be prepared by a known method or a method analogous thereto.

For example, the compound (II) can be prepared by reacting a compound (V) with a compound (VI) and methyl chlorocarbonate according to the following reference production process 1.

Document Example: Tetrahedron 42, 3697(1986)

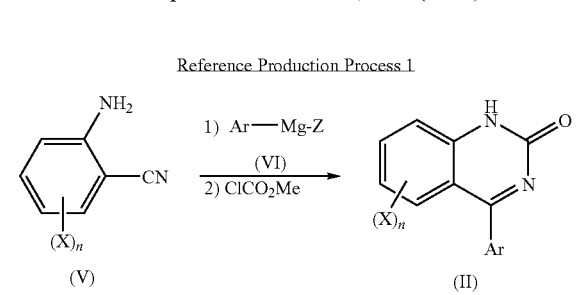

wherein Z represents a halogen atom such as chlorine, bromine or iodine, and other symbols are as defined above.

In this reaction, first, the compound (V) is reacted with the compound (VI). A solvent is usually used. Examples of the solvent include aliphatic hydrocarbon such as pentane, hexane, heptane, or petroleum ether; aromatic hydrocarbon such as benzene, toluene, or xylene; ether such as diethyl ether, methyl tert-butyl ether, diisopropyl ether, dibutyl ether, tetrahydrofuran, or dioxane, and a mixture of two or more kinds of them.

The compound (VI) is usually used in an amount of 1 to 5 equivalents, preferably 2 to 2.5 equivalents based on the compound (V).

At this stage, the reaction temperature is usually from 40 to 100° C., preferably from 50 to 70° C.

The reaction time is usually from 0.2 to 96 hours, preferably from 0.5 to 24 hours, more preferably from 1 to 3 hours.

Next, methyl chlorocarbonate is added to the reaction system. Methyl chlorocarbonate is usually used in an amount of 1 to 5 equivalents, preferably 1 to 2 equivalents based on the compound (V). At this stage, it is preferred that methyl chlorocarbonate is added after cooling to a temperature of 0 to 20° C., followed by heating. The reaction temperature upon heating is usually from 40 to 200° C., preferably from 50 to 70° C. The total reaction time is usually from 0.2 to 96 hours, preferably from 0.5 to 10 hours, more preferably from about 1 to 3 hours.

The compound (II) can also be prepared by reacting a compound (VII) with trichloroacetyl chloride to give a compound (VIII) and reacting the compound (VIII) with ammonia or a salt of ammonia with a weak acidic substance according to the following reference production process 2.

Document Example: Chem. Pharm. Bull., 26, 1633 (1978)

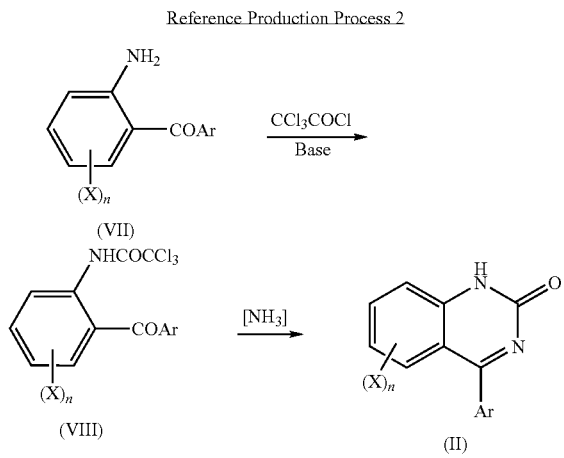

Reference Production Process 2 wherein symbols are as defined above.

In the first reaction, trichloroacetyl chloride is reacted with the compound (VII) in the presence of a base. The reaction may be carried out in the absence of a solvent, and is usually carried out in the presence of a solvent. Examples of the solvent include aliphatic hydrocarbon, aromatic hydrocarbon, ester, ketone, ether, nitrile, acid amide, cyclic amide, phosphoric amide, cyclic urea, sulfoxide, sulfone, halogenated hydrocarbon described in Production Example 2, and their mixtures. Examples of the base include the bases described in Production Example 2. Among these bases, an organic base or an inorganic base is preferred, and triethylamine is commonly used.

The reaction temperature is usually from −50 to 100° C., preferably 0 to 20° C. The reaction time is usually from about 0.1 to 96 hours, preferably from 0.2 to 5 hours, more preferably from 0.5 to 3 hours.

In the second reaction, the compound (VIII) prepared in the first reaction is reacted with ammonia or a compound which generates ammonia in the system. Examples of the compound include salts with weak acidic substances of ammonia, such as ammonium carbonate, ammonium formate, or ammonium acetate. In the reaction, the solvent as described in Production Example 2 is usually used. Preferable examples of the solvent include acid amide, cyclic amide, phosphoric amide, cyclic urea, sulfoxide, and sulfone.

The reaction temperature is usually from 20 to 200° C., preferably from 50 to 120° C.

The reaction time is usually from 0.2 to 96 hours, preferably from 0.5 to 10 hours, more preferably from 1 to 5 hours.

The compound (III) includes a known compound and can be prepared by a known method or a method analogous thereto.

For example, the compound (III) wherein Y is a chlorine atom is a compound (Ia) included in the compound (I) and can be prepared by the method described above.

The compound (IV), the compound (V), the compound (VI) and the compound (VII) are usually known compounds, and are commercially available or can be prepared by a known production process. Particularly, the compound (VI) is a compound called a Grignard reagent. The compound (VI) may be a commercially available product, or may be prepared by a known production process and then used as it is without isolation and purification.

Compounds prepared by the production processes 1, 2 and the reference production processes 1, 2 described above can be isolated and purified by a known means, for example, concentration, concentration under reduced pressure, extraction, dissolution, crystallization, recrystallization, or chromatography.

A compound represented by the general formula (XI) (hereinafter, sometimes, referred to as the compound (XI)) or an agriculturally acceptable salt thereof can also be used as the active ingredient of a plant growth regulator. A certain quinazoline compound having a substituted amino group at the 2-position is known (WO 2005/042501 pamphlet).

Examples of the "C1-6 alkyl group" represented by $R^{11}$ in a compound represented by the general formula (XI) of the present invention (hereinafter may be referred to as a compound (XI)), include methyl, ethyl, propyl, isopropyl, butyl, isobutyl, sec-butyl, tert-butyl, pentyl, 3-methylbutyl, and hexyl. Examples of the "C3-6 alkenyl group" include allyl, 2-butenyl, 3-butenyl, and 3-methyl-2-butenyl. Examples of the "C3-6 alkynyl group" include propargyl, 2-butynyl, and 3-pentynyl. Examples of the "C4-6 alkyl group" include butyl, isobutyl, sec-butyl, tert-butyl, pentyl, 3-methylbutyl, and hexyl. Examples of the "C1-3 alkoxycarbonylmethyl group" include methoxycarbonylmethyl, ethoxycarbonylmethyl, propyloxycarbonylmethyl, and isopropyloxycarbonylmethyl. Examples of the "C1-3 alkoxy C1-3 alkyl group" include 2-methoxyethyl, 2-methoxypropyl, 3-methoxypropyl, 2-ethoxyethyl, and 3-ethoxypropyl.

The "C1-6 alkyl group", "C3-6 alkenyl group", "C3-6 alkynyl group" and "C4-6 alkyl group" described above may have one or more substituents, preferably one to three substituents selected from a hydroxyl group, a C1-3 alkoxy group, a C1-3 alkoxycarbonyl group, a cyano group, a 2-furyl group and a 2-tetrahydrofuryl group at substitutable positions. When the number of substituents is 2 or more, the substituents may be the same or different.

Examples of the "C1-3 alkoxy group" described as an example of the substituent include methoxy, ethoxy, propyloxy, and isopropyloxy. Examples of the "C1-3 alkoxycarbonyl group" include methoxycarbonyl, ethoxycarbonyl, propyloxycarbonyl, and isopropyloxycarbonyl.

The compound (XI) may form an acid addition salt. Examples of the acid addition salt include an inorganic acid salt such as hydrochloride, hydrobromide, hydroiodide, phosphate, sulfate, nitrate, or perchlorate; and an organic acid salt such as formate, acetate, tartrate, malate, citrate, oxalate, succinate, benzoate, picrate, methanesulfonate, or p-toluenesulfonate.

When the compound (XI) has an acidic group such as a carboxyl group, a phenolic hydroxyl group or an active methylene group, examples of the salt that may be formed include metal salts such as alkali metal salts (lithium salt, sodium salt, potassium salt, etc.) and alkali earth metal salts (magnesium salt, calcium salt, barium salt, etc.); ammonium salts; and addition salts with organic bases (for example, dimethylamine, triethylamine, piperazine, pyrrolidine, piperidine, 2-phenylethylamine, benzylamine, ethanolamine, diethanolamine, pyridine, collidine, etc.).

Thus, the compound (XI) may be in the form of an agriculturally acceptable salt as described above.

When the compound (XI) has one or more asymmetric centers, the compound includes two or more stereoisomers (for example, enantiomer, diastereomer, etc.). The compound of the present invention includes all stereoisomers and a mixture of two or more stereoisomers.

When the compound (XI) has geometrical isomerism based on a double bond and the like, the compound includes two or more geometrical isomers (for example, E/Z or trans/cis isomer, S-trans/S-cis isomer, etc.). The compound (XI) includes all geometrical isomers and a mixture of two or more geometrical isomers.

The compound of the general formula (XI) in which m is an integer of 1 to 3 and n is 0 is the compound in which the 6-position of the quinazoline skeleton is unsubstituted, that is, a compound of the general formula (XI-1):

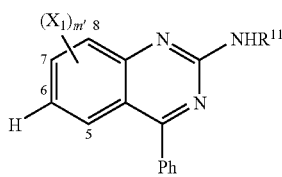

(XI-1)

wherein Ph represents a phenyl group, $R^{11}$ represents a hydrogen atom, a formyl group, a C1-6 alkyl group, a C3-6 alkenyl group or a C3-6 alkynyl group, and the alkyl group, the alkenyl group and the alkynyl group are optionally substituted with at least one substituent selected from a hydroxyl group, a C1-3 alkoxy group, a C1-3 alkoxycarbonyl group, a cyano group, a 2-furyl group and a 2-tetrahydrofuryl group, m' represents an integer of 1 to 3, $X_1$ represents a chlorine atom, a bromine atom, a trifluoromethyl group, a cyano group or a nitro group, when m' is 2 or more, each $X_1$ is the same or different from each other, provided that when m' is 1, $X_1$ is a chlorine atom and $R^{11}$ represents a methyl group; $X_1$ is an 8-chlorine atom.

The compound of the general formula (XI) in which n is 1 is the compound in which the 6-position of the quinazoline skeleton is substituted with $X_2$, that is, a compound of the general formula (XI-2):

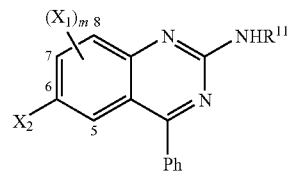

(XI-2)

wherein Ph represents a phenyl group, $R^{11}$ represents a hydrogen atom, a formyl group, a C1-6 alkyl group, a C3-6 alkenyl group or a C3-6 alkynyl group, and the alkyl group, the alkenyl group and the alkynyl group are optionally substituted with at least one substituent selected from a hydroxyl group, a C1-3 alkoxy group, a C1-3 alkoxycarbonyl group, a cyano group, a 2-furyl group and a 2-tetrahydrofuryl group, m represents an integer of 0 to 3, $X_1$ and $X_2$ may be the same or different and represent a chlorine atom, a bromine atom, a trifluoromethyl group, a cyano group or a nitro group, when m is 2 or more, each $X_1$ is the same or different from each other, provided that when any one of the following conditions (1) to (3) is satisfied, m represents an integer of 1 to 3:

(1) $X_2$ is a chlorine atom, and $R^{11}$ is a group selected from a hydrogen atom, methyl group, a 2-hydroxyethyl group, a 3-hydroxypropyl group, a 2,2-dimethoxyethyl group and a cyanomethyl group, (2) $X_2$ is a bromine atom, and $R^{11}$ is selected from a 2-hydroxyethyl group, a 3-hydroxypropyl group and a 2-methoxyethyl group, and (3) $X_2$ is a nitro group, and $R^{11}$ is a 3-hydroxypropyl group.

Preferable examples of the compound (XI) include the following compounds.

(1) A compound of the general formula (XI), wherein $R^{11}$ is a hydrogen atom, a formyl group, a methyl group, an ethyl group, a 2-hydroxyethyl group, a 3-hydroxypropyl group, a 2-methoxyethyl group, a furfuryl group, a methoxycarbonylmethyl group or an ethoxycarbonylmethyl group, m is 0, n is 1, and $X_2$ is a chlorine atom or a nitro group.

(2) A compound of the general formula (XI), wherein $R^{11}$ is a hydrogen atom, a formyl group, a methyl group, an ethyl group, a 2-hydroxyethyl group, a 2-methoxyethyl group, a furfuryl group, a methoxycarbonylmethyl group or an ethoxycarbonylmethyl group, m is 1, n is 1, $X_1$ is an 8-chlorine atom, and $X_2$ is a chlorine atom or a nitro group.

(3) A compound of the general formula (XI), wherein m is an integer of 1 to 3, and n is 0.

(4) A compound of the general formula (XI), wherein $R^{11}$ is a formyl group, a C4-6 alkyl group, a C3-6 alkenyl group or a C3-6 alkynyl group, in which the alkyl group, the alkenyl group and the alkynyl group are optionally substituted with (a) hydroxyl group(s) or (a) C1-3 alkoxy group(s), or $R^{11}$ is a C1-3 alkoxycarbonylmethyl group, a C1-3 alkoxy C1-3 alkyl group or a furfuryl group, m is 0, n is 1, and $X_2$ is a chlorine atom.

(5) A compound of the general formula (XI), wherein n is 1.

(6) A compound of the general formula (XI), wherein m is 1 to 3, and n is 1.

(7) A compound of the general formula (XI), wherein $R^{11}$ is a C1-3 alkoxycarbonylmethyl group or a furfuryl group.

(8) A compound of the general formula (XI), wherein n is 1, and $X_2$ is a trifluoromethyl group or a cyano group.

The compound (XI) is a novel substance and can be prepared by reacting a compound (XII) with a compound (XIII) according to the following production process 11.

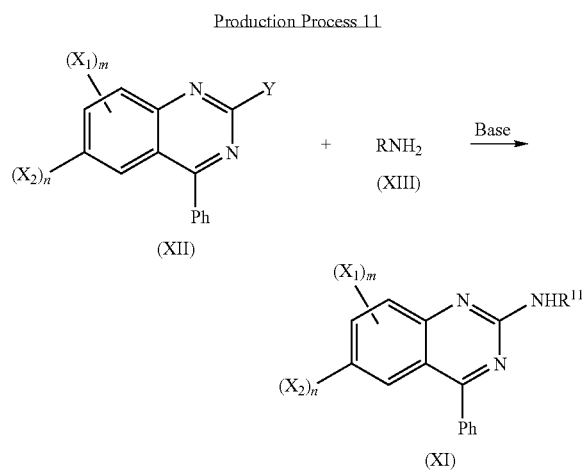

Production Process 11 wherein Y represents a leaving group (for example, a halogen atom such as fluorine, chlorine, bromine or iodine; an alkane- or arene-sulfonyloxy group such as a methanesulfonyloxy group, a benzenesulfonyloxy group or a p-toluenesulfonyloxy group; or an alkane-, arene- or arenealkane-sulfonyl group such as methanesulfonyl, benzenesulfonyl or phenylmethanesulfonyl), and other symbols are as defined above.

The reaction may be carried out with or without using a solvent. Examples of the solvent include aliphatic hydrocarbon such as pentane, hexane, heptane, petroleum ether, or cyclohexane; ester such as methyl acetate, ethyl acetate, ethyl formate, or ethyl propionate; ketone such as acetone, or methyl ethyl ketone; ether such as diethyl ether, methyl tert-butyl ether, diisopropyl ether, dibutyl ether, tetrahydrofuran, or dioxane; alcohol such as methanol, ethanol, or isopropanol; nitrile such as acetonitrile, or propionitrile; acid amide such as dimethylformamide, or dimethylacetamide; cyclic amide such as 1-methyl-2-pyrrolidone; phosphoric amide such as hexamethylphosphoramide; cyclic urea such as 1,3-dimethyl-2-imidazolidinone; sulfoxide such as dimethyl sulfoxide; sulfone such as sulfolane; halogenated hydrocarbon such as dichloromethane, chloroform, 1,2-dichloroethane, or carbon tetrachloride; aromatic amine such as pyridine, picoline, lutidine, or quinoline; their mixtures, water, and mixtures of the solvents and water.

When a mixture of the solvent with water is used and the reaction is not a homogeneous system, a phase transfer catalyst (for example, a quaternary ammonium salt such as benzyltriethylammonium chloride, or benzyltriethylammonium bromide, crown ether such as 18-crown-6, etc.) may be used.

Examples of the base include alkali metal alcoholate such as sodium ethylate, sodium methylate, or potassium tert-butoxide; an organic base such as pyridine, picoline, lutidine, quinoline, triethylamine, diisopropylethylamine, 4-dimethylaminopyridine, or N,N-dimethylaniline; an inorganic base such as potassium carbonate, sodium carbonate, sodium hydroxide, potassium hydroxide, sodium hydrogen carbonate, or potassium hydrogen carbonate; metal hydride such as lithium hydride, sodium hydride, or potassium hydride; and an organic lithium reagent such as butyl lithium, or lithium diisopropylamide.

The amount of the base to be used is not particularly limited as long as it does not adversely influence the reaction. A large excess amount of the base can also be used as a solvent.

When the compound (XIII) is an amine, an excess amount of the compound (XIII) can also be used as both a base and a solvent.

The reaction temperature is usually from −50 to 200° C., preferably from room temperature to 150° C. The reaction time is usually from 0.1 to 96 hours, preferably from 0.1 to 72 hours, more preferably from 0.1 to 24 hours.

When the compound (XIII) is a low boiling point-compound such as ammonia, methylamine or ethylamine or when the reaction proceeds slowly, the reaction can also be heated to a temperature of about 40 to 150° C. and pressurized (for example, at 1.1 to 100 atmospheric pressure) in a pressure-resistant closed vessel.

The compound (XII) includes a known compound and can be prepared by a known method or a method analogous thereto. For example, a compound (XIIa) in which Y is a chlorine atom can be prepared by reacting a compound (XIV) with phosphorus oxychloride according to the following reference production process 11.

Document Example: JP-A 62-145073

Reference Production Process 11

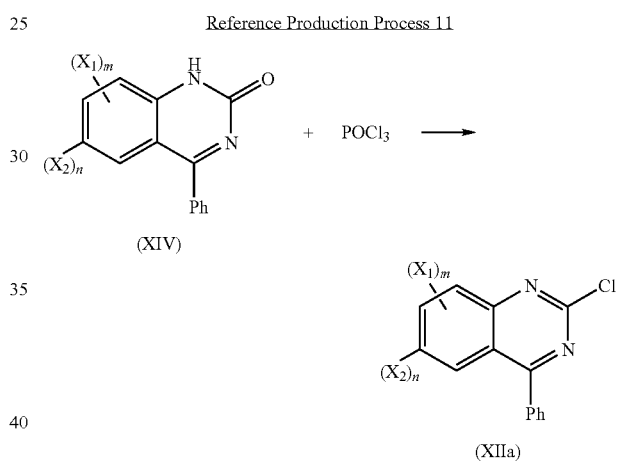

wherein symbols are as defined above.

The above reaction may be carried out in a solvent which does not adversely affect the reaction, and is usually carried out in the absence of a solvent using an excess amount of phosphorus oxychloride (5 equivalents to 30 equivalents based on the compound (XIV)).

The reaction temperature is usually from 80 to 200° C., preferably from 90° C. to the reflux temperature (105° C.).

The reaction time is usually from 0.1 to 96 hours, preferably from 0.5 to 5 hours, more preferably 0.5 to 2 hours. When the reaction proceeds slowly even under reflux, the reaction can also be heated to a temperature of about 200° C. and pressurized (for example, at 1.1 to 100 atmospheric pressure) in a pressure-resistant closed vessel.

The compound (XIV) includes a known compound and can be prepared by a known method or a method analogous thereto. For example, the compound (XIV) can be prepared by reacting a compound (XV) with a compound (XVI) and methyl chlorocarbonate according to the following reference production process 12.

Document Example: Tetrahedron 42, 3697 (1986)

Reference Production Process 12

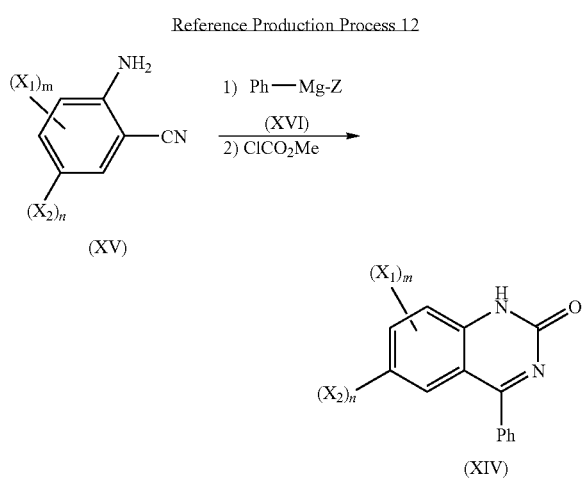

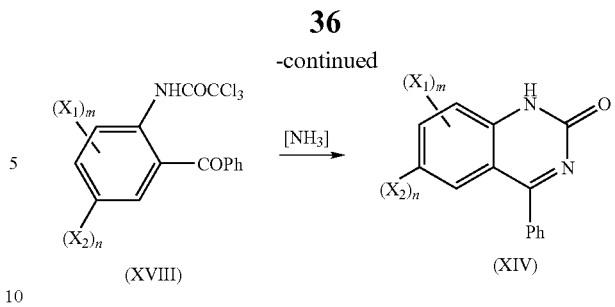

wherein symbols are as defined above.

In the first reaction, trichloroacetyl chloride is reacted with the compound (XVII) in the presence of a base. The reaction may be carried out in the absence of a solvent, and is usually carried out in the presence of a solvent. Examples of the solvent include aliphatic hydrocarbon, aromatic hydrocarbon, ester, ketone, ether, nitrile, acid amide, cyclic amide, phosphoric amide, cyclic urea, sulfoxide, sulfone, halogenated hydrocarbon described in Production Example 11, and their mixtures.

Examples of the base include the bases described in Production Example 11. Among these bases, an organic base or an inorganic base is preferred, and triethylamine is commonly used.

The reaction temperature is usually from −50 to 100° C., preferably 0 to 20° C.

The reaction time is usually from about 0.1 to 96 hours, preferably from 0.2 to 5 hours, more preferably from 0.5 to 3 hours.

wherein Z represents a halogen atom such as chlorine, bromine, or iodine, and other symbols are as defined above.

In the reaction, first, a compound (XV) is reacted with a compound (XVI). A solvent is usually used, and examples thereof include aliphatic hydrocarbon such as pentane, hexane, heptane, or petroleum ether; aromatic hydrocarbon such as benzene, toluene, or xylene; ether such as diethyl ether, methyl tert-butyl ether, diisopropyl ether, dibutyl ether, tetrahydrofuran, or dioxane, and a mixture of two or more kinds of them.

The compound (XVI) is usually used in the amount of 1 to 5 equivalents, preferably 2 to 2.5 equivalents based on the compound (XV).

The reaction temperature is usually from 40 to 100° C., preferably from 50 to 70° C.

The reaction time is usually from 0.2 to 96 hours, preferably from 0.5 to 24 hours, more preferably from 1 to 3 hours.

Next, methyl chlorocarbonate is added to the reaction system. Methyl chlorocarbonate is usually used in an amount of 1 to 5 equivalents, preferably 1 to 2 equivalents based on the compound (XV). At this stage, it is preferred that methyl chlorocarbonate is added after cooling to a temperature of 0 to 20° C., followed by heating. The reaction temperature upon heating is usually from 40 to 200° C., preferably from 50 to 70° C. The total reaction time is usually from 0.2 to 96 hours, preferably from 0.5 to 10 hours, more preferably from about 1 to 3 hours.

The compound (XIV) can also be prepared by reacting a compound (XVII) with trichloroacetyl chloride to give a compound (XVIII) and reacting the compound (XVIII) with ammonia or a weak acidic substance of ammonia according to the following reference production process 13.

Document Example: Chem. Pharm. Bull., 26, 1633 (1978)

Reference Production Process 13

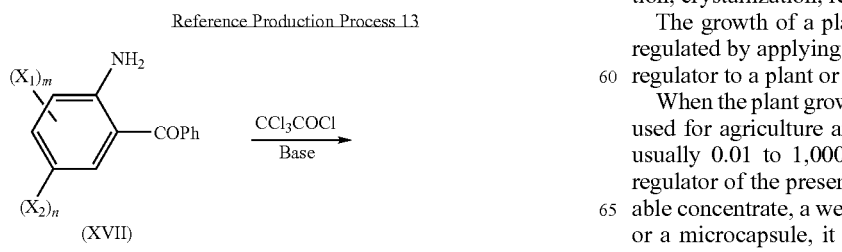

In the second reaction, the compound (XVIII) prepared in the first reaction is reacted with ammonia or a compound which generates ammonia in the system. Examples of the compound include salts with weak acidic substances of ammonia, such as ammonium carbonate, ammonium formate, or ammonium acetate. In the reaction, the solvent as described in Production Example 11 is usually used. Preferable examples of the solvent include acid amide, cyclic amide, phosphoric amide, cyclic urea, sulfoxide, and sulfone.

The reaction temperature is usually from 20 to 200° C., preferably from 50 to 120° C.

The reaction time is usually from 0.2 to 96 hours, preferably from 0.5 to 10 hours, more preferably from 1 to 5 hours.

The compound (XIII), the compound (XV), the compound (XVI) and the compound (XVII) are usually known compounds, and are commercially available or can be prepared by a known production process.

Particularly, the compound (XVI) is a compound called a Grignard reagent. The compound (XVI) may be a commercially available product, or may be prepared by a known production process and then used as it is without isolation and purification.

Compounds prepared by the production process 11 and the reference production processes 11, 12 and 13 can be isolated and purified by a known means, for example, concentration, concentration under reduced pressure, extraction, dissolution, crystallization, recrystallization, or chromatography.

The growth of a plant in the present invention is usually regulated by applying an effective amount of a plant growth regulator to a plant or habitat of the plant.

When the plant growth regulator of the present invention is used for agriculture and forestry, the application amount is usually 0.01 to 1,000 g/1000 m². When the plant growth regulator of the present invention is the form of an emulsifiable concentrate, a wettable powder, a flowable formulation, or a microcapsule, it is usually sprayed after dilution with water so as to have an active ingredient concentration of 0.001 to 10,000 ppm. When the plant growth regulator of the present invention is the form of a powder or a granule, it is usually applied as it is.

For the purpose of promoting the growth of roots of plants in soil of a cultivated field, the soil may be treated with directly the plant growth regulator thus formulated of the present invention or with a dilution of the plant growth regulator. Further, the plant growth regulator may be formulated into a resin formulation in the form of a sheet or string. The resin formulation can be applied by winding around plants, stretching in the vicinity of plants, laying on the soil surface at the plant feet, or the like. The plant growth regulator of the present invention can also be used by foliage treatment or treatment of buds. Seedbeds before planting or planting holes or plant feet in planting can be also treated with the plant growth regulator of the present invention. Target plants are treated with the plant growth regulator once or plural times.

When the plant growth regulator of the present invention is used for foliage treatment of a plant body or soil treatment, the application amount may vary depending upon the formulation type, the timing, method and place of application, and the target plant, and is usually from 0.1 to 10,000 g per hectare. When the plant growth regulator is used as a dilution with water, the concentration of the plant growth regulator may vary depending upon the formulation type, the timing, method and place of application, and the target plant, and is usually from 0.001 to 10,000 ppm, preferably from 0.01 to 1,000 ppm.

The plant growth regulator of the present invention can be also used for a treatment of a plant before transplantation. When the plant growth regulator of the present invention is directly absorbed into a plant before transplantation, the root portion or all of the plant can be immersed in a solution or suspension of the plant growth regulator with a concentration of 0.001 ppm to 10,000 ppm.

Seeds of the target plant can be directly treated with a formulation of the plant growth regulator of the present invention. Examples of such a treatment method include a method which comprises immersing seeds of a plant in the plant growth regulator of the present invention prepared so that the concentration of an active ingredient can be 1 to 10,000 ppm, a method which comprises spraying or coating seeds of a plant with the plant growth regulator of the present invention prepared so that the concentration of an active ingredient can be 1 to 10,000 ppm, and a method which comprises coating seeds of a plant with powder of the plant growth regulator of the present invention.

The plant growth regulator of the present invention may be mixed with a water culture medium for water culture, or may be used as one of medium components for tissue culture. When the plant growth regulator of the present invention is used for water culture, the plant growth regulator can be dissolved or suspended in a water culture medium such as Enshi at a concentration of 0.001 ppm to 10,000 ppm. When the plant growth regulator of the present invention is used for tissue culture or cell culture, the plant growth regulator can be dissolved or suspended in a plant tissue culture medium conventionally used, such as an MS medium at a concentration of 0.001 ppm to 10,000 ppm. In this case, saccharides as a carbon source and various plant hormones can be conventionally added to the medium.

The plant growth regulator of the present invention can be also used in combination with a fungicide, an insecticide, an acaricide, a nematocide, a herbicide, a plant growth regulator and/or a fertilizer.

Their application amounts and application concentrations may vary depending upon the formulation type, the timing, place and method of application, the kind of a plant and effect to be expected, and therefore they can be increased or decreased without limitation to the above ranges.

In the plant growth regulating method as described above, the plant growth regulator can be used.

It is also possible to specify a substance having the ability to promote the growth of a root of a plant evaluated by the method for testing the ability of a test substance to promote the growth of a root of a plant which comprises the first step and the second step using a cytokinin receptor selected from the group A, and then to bring the specified substance having the ability to promote the growth of a root of a plant into contact with a plant to promote the growth of a root of the plant. A method for bringing the specified substance having the ability to promote the growth of a root of a plant into contact with a plant includes the formulation method and the application method as described above.

The plant growth regulator of the present invention can be used for the purpose of improvement in seedling establishment and improvement in a rate of taking root in soil by promotion of the growth of roots upon direct seeding cultivation of rice. The plant growth regulator of the present invention can also be used for the purpose of promotoin of the growth of roots upon raising of rice seedlings in a nursery box. The plant growth regulator of the present invention can also be used for the purpose of improvement in root swelling and heat- and dry-resistance of green of a golf course. In the case of crops such as soybean, corn and wheat, the plant growth regulator of the present invention can be used for the purpose of improvement in root swelling, improvement productivity by seedling establishment at an early stage or reduction in the application amount of herbicides. In the case of culture of tomato, paper or the like, the plant growth regulator of the present invention can be used for the purpose of improvement in a rate of taking root in soil upon transplantation. In the case of production of seedlings of vegetables, the use of the plant growth regulator of the present invention can be expected to lead to uniform seedling establishment and therefore improvement in efficiency of mechanical transplantation.

The plant growth regulator of the present invention can be used to control of apical dominance of a plant. For example, the plant growth regulator of the present invention can be used to inhibit the growth of axillary buds of tobacco, rose and the like. The plant growth regulator of the present invention can control the formation of flower buds of fruit crops, flowering plants and the like, and therefore can be used as a flower thinning agent. The plant growth regulator of the present invention can also increase flower buds, and thereby increase in yield of fruit crops or improvement in quality of flowering plants can be achieved. The plant growth regulator of the present invention can also inhibit the growth of branches of fruit crops to decrease the number of branches or can promote the growth of branches of fruit crops to increase the number of branches, and therefore it can be utilized for control of the growth of a tree body.

The plant growth regulator of the present invention can be used for tissue culture technologies such as dedifferentiation to callus or redifferentiation from callus. For example, the plant growth regulator of the present invention can be used to promote callus formation from plant tissues. The plant growth regulator of the present invention can be also used to improve efficiency of redifferentiation from an adventive embryo of soybean or the like.

The plant growth regulator of the present invention can be used to control aging of a plant. For example, the plant growth regulator of the present invention can be used to inhibit aging of and improve keeping of cut flowers of flowering plants such as carnation. The plant growth regulator of the present invention can also be used to inhibit the maturation of fruits. The plant growth regulator of the present invention can also prevent aging of leaves of seedlings of paddy rice, and thus good seedlings can be grown. A plants such as cotton can be treated with the plant growth regulator of the present invention before harvesting to promote aging of leaves.

The plant-derived cytokinin receptor consisting of an amino acid sequence shown in the above group B can be used as a study tool. For example, it can be used as a study tool for carrying out study such as the testing for the ability to promote the growth of a root of a plant or the searching for a chemical substance having the ability to control the growth or differentiation of a plant as described above. The cytokinin receptor can be also used as a study tool in study for analyzing a mechanism of action of a drug which acts on a cytokinin receptor.

A polynucleotide encoding an amino acid sequence shown in the group B and a polynucleotide having a nucleotide sequence complementary thereto, a partial nucleotide sequence of a polynucleotide encoding an amino acid sequence shown in the group B or a polynucleotide having a nucleotide sequence complementary to the partial nucleotide sequence, and a polypeptide comprising a nucleotide sequence of SEQ ID NO: 3 or 4 can be also used as study tools. For example, a portion of them can function as a polynucleotide to be used in the production process of a cytokinin receptor as described above. Also a portion of them can be used as an important study tool for obtaining a polynucleotide shown in the polynucleotide group B using PCR, or obtaining a polynucleotide shown in the polynucleotide group B using hybridization, as described above.

When screening of a plant growth regulator is carried out, they can be used as a test tool in experiments for screening. Specifically, they can be used as a test tool in experiments for the testing of the ability to promote the growth of a root of a plant and the searching of a chemical substance having the ability to control the growth or differentiation of a plant as described above.

The present invention further includes a system (hereinafter, sometimes, referred to as the system of the present invention) which comprises a means for inputting, storing and managing data information on an activity (or the presence or absence of intracellular signaling or the amount thereof) of a test substance for inhibiting intracellular signaling from a plant-derived cytokinin receptor of a cell (hereinafter, sometimes, referred to as the means a), a means for inquiring and searching the data information based on desired conditions (hereinafter, sometimes, as the means b), and a means for displaying and outputting the inquired and searched data (hereinafter, sometimes, referred to as the means c).

First, the means a is described. As described above, the means a is a means which inputs data information of an activity of a test substance for inhibiting intracellular signaling from a plant-derived cytokinin receptor of a cell, and then stores and manages the input information. Such information is input by an input means 1 and is usually memorized in a memory means 2. The input means includes a means capable of inputting the information, such as a keyboard or a mouse. When input, storage and management of the information are completed, the information proceeds to the subsequent means b. In the storage and management of the information, a lot of data may be efficiently stored and managed by inputting information having a data structure using hardware such as a computer and software such as OS and database, and storing the information in a proper storage device, for example, a computer-readable recording medium such as a flexible disk, a photomagnetic disk, a CD-ROM, a DVD-ROM, or a hard disk.

The means b is described. As described above, the means b is a means which inquires and searches the data information stored and managed by the means a based on conditions for obtaining the desired results. When conditions for inquiry and research are input by the input means 1 and information corresponding to the conditions is usually selected from the information stored in the storage means 2, the information proceeds to the subsequent means c. The selected results are usually stored in the storage means 2 and can be displayed by the display and output means 3.

The means c is described. As described above, the means c is a means which displays and outputs the inquired and searched results. The display and output means 3 includes a display, and a printer, and the results may be displayed on a display device of a computer, or output on a paper by printing.

EXAMPLES

Hereinafter, the present invention will be described in detail by way of Examples, but the present invention is not limited thereto.

The compound (I) used in the present invention will be described in more specifically by way of Synthesis Examples and Reference Synthesis Examples, but the compound (I) is not limited to these examples.

In Synthesis Examples and Reference Synthesis Examples, "room temperature" usually means a temperature of 10 to 30° C. "$^1$H NMR" means a proton magnetic resonance spectrum. Using tetramethylsilane as an internal standard, the measurement was carried out with a spectrometer (400 MHz), Model JNM-AL400, manufactured by JEOL Ltd. and chemical shifts (δ) were expressed as ppm. "Mp" means a melting point and was measured with a melting point meter, Model Mettler FP61.

Abbreviations used in the following Synthesis Examples, Reference Synthesis Examples and Tables 3 to 7 have the following meanings. $CDCl_3$: deuterated chloroform, DMSO-$d_6$: deuterated dimethyl sulfoxide, s: singlet, d: doublet, t: triplet, q: quartet, dd: double doublet, m: multiplet, br: broad, J: coupling constant, Me: methyl; Et: ethyl, Pr: propyl, i-Pr: isopropyl, t-Bu: tertiary butyl, Ph: phenyl, Ac: acetyl, THF: tetrahydrofuran, DMF: N,N-dimethylformamide, DMSO: dimethyl sulfoxide and MTBE: methyl tertiary butyl ether Synthesis Example 1

Preparation of 2,8-dichloro-4-phenylquinazoline (compound No. Ia1-11)

To 1.24 g of 8-chloro-4-phenyl-2(1H)-quinazolinone (compound No. II-11) was added 6.65 g of phosphorus oxychloride, followed by stirring at 95° C. for 1 hour. The resulting reaction solution was poured into 200 ml of ice water, and sodium bicarbonate was then added, thereby adjusting the pH to 9. Then, precipitated crystals were collected by filtration. The collected product was recrystallized from ethanol to obtain 1.07 g of the titled compound. Mp.154.4.° C. $^1$H NMR ($CDCl_3$): 7.52-7.65 (4H, m), 7.76-7.80 (2H, m), 8.02-8.08 (2H, m).

Synthesis Example 2

Preparation of 2-amino-6,8-dichloro-4-phenylquinazoline (compound No. Ic12-4)

A mixture of 300 mg of 2,6,8-trichloro-4-phenylquinazoline (compound No. Ia1-12), 30 g of an aqueous 28% ammonia solution and 6 ml of acetonitrile was reacted at 105° C. for 1.5 hours in a pressure-resistant reaction vessel. The resulting reaction solution was cooled and then poured into 100 ml of water. The mixture was extracted with 60 ml of ethyl acetate and the resultant extract was concentrated. The resulting residue was purified by silica gel column chromatography (chloroform) to obtain 230 mg of the titled compound. Mp.212.7° C. $^1$H NMR (CDCl$_3$): 5.56 (2H, br. s), 7.54-7.60 (3H, m), 7.63-7.68 (2H, m), 7.74 (1H, d, J=2.3 Hz), 7.79 (1H, d, J=2.3 Hz).

Synthesis Example 3

Preparation of 6-chloro-2-furfurylamino-4-phenylquinazoline (compound No. Ic3-16)

A mixture of 275 mg of 2,6-dichloro-4-phenylquinazoline (compound No. Ia1-3) and 486 mg of furfurylamine was stirred at 85° C. for 40 minutes and then poured into 50 ml of water. The mixture was extracted with ethyl acetate and the resultant extract was washed with water and then concentrated. The resulting residue was recrystallized from ethanol to obtain 280 mg of the titled compound. Mp.142.0° C. $^1$H NMR (CDCl$_3$): 4.77 (2H, d, J=5.6 Hz), 5.70 (1H, br. t, J=5.6 Hz), 6.29-6.32 (2H, m), 7.36 (1H, dd, J=1.8, 0.9 Hz), 7.53-7.70 (7H, m), 7.78 (1H, d, J=2.2 Hz).

Synthesis Example 4

Preparation of 6-chloro-2-ethoxycarbonylmethylamino-4-phenylquinazoline (compound No. Ic3-33)

To 550 mg of 2,6-dichloro-4-phenylquinazoline (compound No. Ia1-3) and 419 mg of glycine ethyl ester hydrochloride were added 3 ml of DMF and 607 mg of triethylamine, followed by stirring at 85° C. for 5.5 hours. The resulting reaction solution was poured into 100 ml of water and extracted with ethyl acetate. The extract was concentrated. The resulting residue was purified by silica gel column chromatography (hexane:ethyl acetate=6:1 to 3:1 to obtain 503 mg of the titled compound. Mp.146.1° C. $^1$H NMR (CDCl$_3$): 1.30 (3H, t, J=7.2 Hz), 4.25 (2H, q, J=7.2 Hz), 4.31 (2H, d, J=5.2 Hz), 5.97 (1H, br. s), 7.54-7.63 (5H, m), 7.67-7.70 (2H, m), 7.79 (1H, s).

Synthesis Example 5

Preparation of 6-chloro-2-methoxyamino-4-phenylquinazoline (compound No. Ic3-32)

To a mixture of 275 mg of 2,6-dichloro-4-phenylquinazoline (compound No. Ia1-3), 10 ml of acetonitrile and 334 mg of methoxyamine hydrochloride was added dropwise 506 mg of triethylamine at room temperature to obtain a mixture. The mixture was charged in a pressure-resistant reaction vessel made of stainless steel and the reaction was carried out at 105° C. for 3.5 hours. After cooling, the reaction solution was poured into 100 ml of water. The mixture was extracted with ethyl acetate and the resultant extract was washed with water and then concentrated. The resulting residue was purified by silica gel column chromatography (hexane:ethyl acetate=3:1) to obtain 156 mg of crude crystals. The crude crystals were recrystallized from ethyl acetate to obtain 55 mg of the titled compound. Mp.173.9° C. $^1$H NMR (CDCl$_3$): 3.98 (3H, s), 7.47-7.72 (6H, m), 7.87 (1H, d, J=9.0 Hz), 7.89 (1H, d, J=2.2 Hz), 8.03 (1H, br. s).

Synthesis Example 6

Preparation of 6-chloro-2-(2-hydroxyethylthio)-4-phenylquinazoline (compound No. Ie3-1)

To a solution of 86 mg of 2-mercaptoethanol in DMF (7.5 ml) was added 44 mg of sodium hydride (60%), followed by stirring at room temperature for 30 minutes. To the reaction mixture was added 275 mg of 2,6-dichloro-4-phenylquinazoline (compound No. Ia1-3), followed by stirring at room temperature for 2 hours. The reaction solution was poured into 100 ml of water and extracted with ethyl acetate. The resultant extract was concentrated. The resulting residue was purified by silica gel column chromatography (ethyl acetate:hexane=1:5) to obtain 266 mg of the titled compound. Mp.124.4° C. $^1$H NMR (CDCl$_3$): 3.50 (2H, t, J=5.5 Hz), 3.64 (1H, br. t), 4.07 (2H, q-like, J=5.5 Hz), 7.57-7.61 (3H, m), 7.71-7.74 (2H, m), 7.77 (1H, dd, J=8.9, 2.3 Hz), 7.85 (1H, d, J=8.9 Hz), 7.97 (1H, d, J=2.3 Hz).

Synthesis Example 7

Preparation of 6-chloro-2-formamido-4-phenylquinazoline (compound No. Ic3-35)

To a solution of 54 mg of dry formamide in DMF (5 ml) was added 48 mg of sodium hydride (60%), followed by stirring at room temperature for 30 minutes. To the reaction mixture was added 275 mg of 2,6-dichloro-4-phenylquinazoline (compound No. Ia1-3), followed by warming to 85° C. and further stirring for 3 hours. The resulting reaction solution was poured into 100 ml of water and extracted with ethyl acetate. The extract was concentrated. The resulting residue was purified by silica gel column chromatography (ethyl acetate:hexane=1:3) to obtain 64 mg of the titled compound. Mp.252.1° C. $^1$H NMR: 7.59-7.66 (3H, m), 7.72-7.81 (3H, m), 7.88 (1H, d, J=8.8 Hz), 8.02 (1H, d, J=2.0 Hz), 8.37 (1H, br. d, J=10.4 Hz), 9.71 (1H, d, J=10.4 Hz).

Synthesis Example 8

Preparation of 6-chloro-2-(1-methylhydrazino)-4-phenylquinazoline (compound No. Ic3-27)

A mixture of 275 mg of 2,6-dichloro-4-phenylquinazoline (compound No. Ia1-3) and 461 mg of monomethylhydrazine was stirred at 85° C. for 30 minutes. The resulting reaction product was cooled and 200 ml of water was added thereto. Precipitated crystals were collected by filtration and the collected product was purified by column chromatography (ethyl acetate) to obtain 225 mg of the titled compound. Mp. 155.9° C. $^1$H NMR (CDCl$_3$): 3.52 (3H, s), 4.65 (2H, s), 7.54-7.63 (5H, m), 7.70-7.74 (2H, m), 7.80 (1H, d, J=2.0 Hz).

Synthesis Example 9

Preparation of 2-(2-aminoethoxy)-6-chloro-4-phenylquinazotine (compound No. Id3-1)

In the same manner as in Synthesis Example 6, 500 mg of 2,6-dichloro-4-phenylquinazoline (compound No. Ia1-3) and 382 mg of N-(2-hydroxyethyl)phthalimide were reacted to obtain 380 mg of 6-chloro-4-phenyl-2-(2-phthalimidoethoxy)quinazoline. Mp. 154.7° C. $^1$H NMR (CDCl$_3$): 4.25 (2H, t, J=5.8 Hz), 4.84 (2H, t, J=5.8 Hz), 7.53-7.60 (3H, m), 7.67-7.71 (3H, m), 7.72-7.76 (3H, m), 7.78-7.82 (2H, m), 7.97 (1H, d, J=2.2 Hz).

A mixture of 380 mg of 6-chloro-4-phenyl-2-(2-phthalimidoethoxy)quinazoline, 70 mg of hydrazine hydrate and 6 ml of ethanol was heated under reflux for 2 hours. To the resulting reaction solution was added 1.2 ml of water, and ethanol was then distilled off. To the resulting residue was added 1.5 ml of concentrated hydrochloric acid, followed by heating under reflux for 1 hour. The resulting reaction product was cooled and poured into a saturated solution of sodium bicarbonate in water and extracted with ethyl acetate. The extract was concentrated to obtain 240 mg of the titled compound. Mp.134.9° C. $^1$H NMR (CDCl$_3$): 3.59-3.63 (2H, m), 3.84 (2H, t, J=4.6 Hz), 6.15 (2H, br. s), 7.53-7.59 (5H, m), 7.63-7.67 (2H, m), 7.75 (1H, d, J=1.2 Hz).

Synthesis Example 10

Preparation of 2-(2-acetylthioethylamino)-6-chloro-4-phenylquinazoline (compound No. Ic3-14)

To a solution of 292 mg of triphenylphosphine in dehydrated THF (3 ml) was added dropwise 563 mg of a 40% solution of diisopropylcarbodiimide in toluene under ice cooling, followed by stirring for 20 minutes. To the resulting suspension was added dropwise a solution of 167 mg of 6-chloro-2-(2-hydroxyethylamino)-4-phenylquinazoline (compound No. Ic3-1) in dehydrated THF (2 ml) under ice cooling, and immediately 127 mg of thioacetic acid was added dropwise. The resulting yellow clear solution was stirred for 1 hour under ice cooling, stirred at room temperature for 1 hour, poured into a saturated solution of sodium bicarbonate in water, and then extracted with chloroform. The extract was concentrated. The resulting residue was purified by silica gel column chromatography (chloroform:ethyl acetate=10:1) to obtain 170 mg of the titled compound. Mp.128.9° C. $^1$H NMR (CDCl$_3$): 2.34 (3H, s), 3.22 (2H, t, J=6.5 Hz), 3.73 (2H, q, J=6.5 Hz), 5.74 (1H, br. t, J=6.5 Hz), 7.53-7.62 (5H, m), 7.65-7.70 (2H, m), 7.77 (1H, s).

Synthesis Example 11

6-chloro-2-(2-mercaptoethylamino)-4-phenylquinazoline (compound No. Ic3-13) and bis[2-(6-chloro-4-phenyl-2-quinazolinyl)aminoethyl]disulfide (compound No. Ic3-15)

A mixture of 108 ma of 2-(2-acetylthioethylamino)-6-chloro-4-phenylquinazoline (compound No. Ic3-14), 2 ml of ethanol and 362 mg of an aqueous 10% sodium hydroxide solution was stirred at room temperature for 2 hours and stirred under heating under reflux for 30 minutes. Then insoluble substances were collected by filtration from the reaction solution. The collected product (solid) was purified by silica gel column chromatography (chloroform:ethyl acetate=10:1) to obtain 50 mg of 6-chloro-2-(2-mercaptoethylamino)-4-phenylquinazoline, first. Mp.165.9° C. $^1$H NMR (CDCl$_3$): 1.46 (1H, t, J=8.5 Hz), 2.84 (2H, q-like, J=7.2 Hz), 3.66 (2H, q-like, J=6.4 Hz), 5.79 (1H, br. t, J=5.4 Hz), 7.55-7.57 (3H, m), 7.60 (2H, s), 7.66-7.69 (2H, m), 7.77-7.78 (1H, m). Then, 28 mg of bis[2-(6-chloro-4-phenyl-2-quinazolinyl)aminoethyl]disulfide (compound represented by the following formula) was obtained.

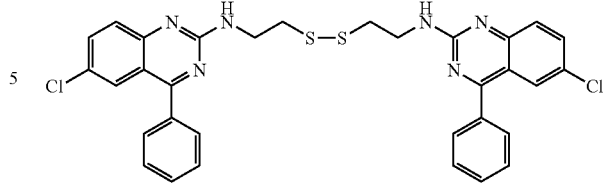

Mp.159.2° C. $^1$H NMR (CDCl$_3$): 3.02 (4H, t, J=6.4 Hz), 3.89 (4H, q, J=6.4 Hz), 5.81 (2H, br. t, J=6.4 Hz), 7.51-7.61 (10H, m), 7.63-7.68 (4H, m), 7.75 (2H, d, J=2.2 Hz).

Examples of compounds which can be prepared in the same manner as in Synthesis Examples described above and commercially available compounds are shown in Table 3, Table 4. Table 5 and Table 6 (also including the compounds prepared in Synthesis Examples described above).

Notes "a)", "b)", "c)" and "d)" in Table 4 and Table 5 are as follows.

TABLE 3

| Compound No. | R | Ar | (X)$_n$ | Melting point (° C.) |
|---|---|---|---|---|
| Ia1-1 | Cl | Ph | 5-Cl | 125.7 |
| Ia1-2 | Cl | Ph | 6-F | 131.9 |
| Ia1-3 | Cl | Ph | 6-Cl | 166.2 |
| Ia1-4 | Cl | Ph | 6-Br | 185.1 (decomposition) |
| Ia1-5 | Cl | Ph | 6-Me | 137.8 |
| Ia1-6 | Cl | Ph | 6-CF$_3$ | 117.5 (decomposition) |
| Ia1-7 | Cl | Ph | 6-NO$_2$ | 242.5 (decomposition) |
| Ia1-8 | Cl | Ph | 6-OMe | 148.6 |
| Ia1-9 | Cl | Ph | 6-CN | 206.8 (decomposition) |
| Ia1-10 | Cl | Ph | 7-Cl | 115.4 |
| Ia1-11 | Cl | Ph | 8-Cl | 154.4 |
| Ia1-12 | Cl | Ph | 6,8-Cl$_2$ | 160.3 |
| Ia1-13 | Cl | p-Cl-Ph | 6-Cl | 205.6 |
| Ia1-14 | Cl | m-Cl-Ph | 6-Cl | 161.3 |
| Ib4-1 | CHO | o-Cl-Ph | 6-Br | |
| Ic0-1 | NH(CH$_2$)$_2$OH | Ph | (n = 0) | |
| Ic1-1 | NH(CH$_2$)$_3$OH | Ph | 5-Cl | 175.7 |
| Ic2-1 | NH(CH$_2$)$_3$OH | Ph | 6-F | 99.3 |
| Ic3-1 | NH(CH$_2$)$_2$OH | Ph | 6-Cl | 137.9 |
| Ic3-2 | pyrrolidino | Ph | 6-Cl | |
| Ic3-3 | NH(CH$_2$)$_3$OH | Ph | 6-Cl | 135.9 |
| Ic3-4 | NH(CH$_2$)$_4$OH | Ph | 6-Cl | 115.6 |
| Ic3-5 | NH(CH$_2$)$_5$OH | Ph | 6-Cl | 117.2 |
| Ic3-6 | NMe(CH$_2$)$_2$OH | Ph | 6-Cl | 128.5 |
| Ic3-7 | NH(CH$_2$)$_2$OMe | Ph | 6-Cl | 89.7 |
| Ic3-8 | NHn-Pr | Ph | 6-Cl | 158.3 |
| Ic3-9 | NMe(CH$_2$)$_2$OMe | Ph | 6-Cl | 88.5 |

TABLE 4

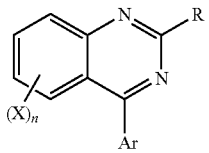

| Compound No. | R | Ar | (X)$_n$ | Melting point (° C.) |
|---|---|---|---|---|
| Ic3-10 | NH(CH$_2$)$_2$CHMe$_2$ | Ph | 6-Cl | 90.1 |
| Ic3-11 | NH(CH$_2$)$_6$OH | Ph | 6-Cl | 107.9 |
| Ic3-12 | NH(CH$_2$)$_2$CH(Me)CH$_2$OH | Ph | 6-Cl | 112.7 |
| Ic3-13 | NH(CH$_2$)$_2$SH | Ph | 6-Cl | 165.9 |
| Ic3-14 | NH(CH$_2$)$_2$SAc | Ph | 6-Cl | 128.9 |
| Ic3-15 | a) | | | 159.2 |
| Ic3-16 | Nhfurfuryl | Ph | 6-Cl | 142.0 |
| Ic3-17 | NHCH$_2$CH=CMe$_2$ | Ph | 6-Cl | 95.9 |
| Ic3-18 | NHCH$_2$CH=C(Me)CH$_2$OH | Ph | 6-Cl | 154.8 |
| Ic3-19 | NH$_2$ | Ph | 6-Cl | 157.8 |
| Ic3-20 | NHNH$_2$ | Ph | 6-Cl | 175.0 |
| Ic3-21 | NH(CH$_2$)$_2$NMe$_2$ | Ph | 6-Cl | 102.1 |
| Ic3-22 | NH(CH$_2$)$_4$NH$_2$ | Ph | 6-Cl | 118.0 |
| Ic3-23 | NHMe | Ph | 6-Cl | 186.9 |
| Ic3-24 | NHEt | Ph | 6-Cl | 156.7 |
| Ic3-25 | NMe$_2$ | Ph | 6-Cl | 141.8 |
| Ic3-26 | NHCH$_2$CN | Ph | 6-Cl | 208.6 (decomposition) |
| Ic3-27 | NMeNH$_2$ | Ph | 6-Cl | 155.9 |
| Ic3-28 | NHi-Pr | Ph | 6-Cl | 112.5 |
| Ic3-29 | NHCH$_2$CH=CH$_2$ | Ph | 6-Cl | 147.3 |
| Ic3-30 | NHCH$_2$C≡CH | Ph | 6-Cl | 168.4 |
| Ic3-31 | NHCH$_2$CONH$_2$ | Ph | 6-Cl | 140.3 |
| Ic3-32 | NHOMe | Ph | 6-Cl | 173.9 |
| Ic3-33 | NHCH$_2$CO$_2$Et | Ph | 6-Cl | 146.1 |
| Ic3-34 | NHCH$_2$CH$_2$CN | Ph | 6-Cl | 198.7 |
| Ic3-35 | NHCHO | Ph | 6-Cl | 252.1 |
| Ic3-36 | guanidine | Ph | 6-Cl | 253.4 (decomposition) |

TABLE 5

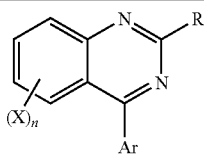

| Compound No. | R | Ar | (X)$_n$ | Melting point (° C.) |
|---|---|---|---|---|
| Ic3-37 | NHtetrahydrofurfuryl | Ph | 6-Cl | syrup, b) |
| Ic3-38 | NH(CH$_2$)$_3$OMe | Ph | 6-Cl | 89.1 |
| Ic3-39 | NHCH$_2$CH(OH)CH$_3$ | Ph | 6-Cl | 154.2 |
| Ic3-40 | NH(CH$_2$)$_2$O(CH$_2$)$_2$OH | Ph | 6-Cl | 117.4 |
| Ic3-41 | NHCH$_2$CH(OH)CH$_2$OH | Ph | 6-Cl | 147.0 |
| Ic3-42 | NHCH$_2$CO$_2$Me | Ph | 6-Cl | 190.5 |
| Ic3-43 | NHCH$_2$CH$_2$CO$_2$Me | Ph | 6-Cl | 117.1 |
| Ic3-44 | NHCH(Me)CH$_2$OH | Ph | 6-Cl | 52.8 |
| Ic3-45 | NHCH$_2$CH$_2$OEt | Ph | 6-Cl | syrup, c) |
| Ic3-46 | NH(CH$_2$)$_3$OEt | Ph | 6-Cl | syrup, d) |
| Ic4-1 | NH(CH$_2$)$_2$OH | Ph | 6-Br | |
| Ic4-2 | NH(CH$_2$)$_3$OH | Ph | 6-Br | 140.9 |
| Ic4-3 | NHCH$_2$CO$_2$Me | Ph | 6-Br | 183.1 (decomposition) |
| Ic5-1 | NH-p-Cl-Ph | Ph | 6-Me | |
| Ic5-2 | NHCH$_2$CONH$_2$ | Ph | 6-Me | |
| Ic5-3 | NHCH$_2$CO$_2$Et | Ph | 6-Me | |
| Ic5-4 | NH$_2$ | Ph | 6-Me | 151.8 |
| Ic5-5 | NH(CH$_2$)$_3$OH | Ph | 6-Me | 121.1 |
| Ic6-1 | NH$_2$ | Ph | 6-CF$_3$ | 160.4 |
| Ic6-2 | NH(CH$_2$)$_3$OH | Ph | 6-CF$_3$ | 135.1 |

TABLE 5-continued

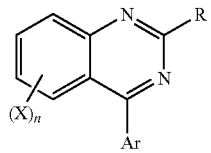

| Compound No. | R | Ar | (X)$_n$ | Melting point (° C.) |
|---|---|---|---|---|
| Ic7-1 | NH(CH$_2$)$_3$OH | Ph | 6-NO$_2$ | 177.4 |
| Ic8-1 | NH(CH$_2$)$_3$OH | Ph | 6-OMe | 115.9 |
| Ic9-1 | NH(CH$_2$)$_3$OH | Ph | 6-CN | 173.3 (decomposition) |
| Ic10-1 | NH(CH$_2$)$_3$OH | Ph | 7-Cl | 129.7 |

TABLE 6

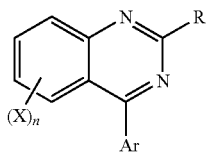

| Compound No. | R | Ar | (X)n | Melting point (° C.) |
|---|---|---|---|---|
| Ic11-1 | NH(CH$_2$)$_3$OH | Ph | 8-Cl | 115.5 |
| Ic12-1 | NH(CH$_2$)$_3$OH | Ph | 6,8-Cl$_2$ | 146.2 |
| Ic12-2 | NHCH$_2$CH$_2$OH | Ph | 6,8-Cl$_2$ | 168.8 |
| Ic12-3 | NHfurfuryl | Ph | 6,8-Cl$_2$ | 158.6 |
| Ic12-4 | NH$_2$ | Ph | 6,8-Cl$_2$ | 212.7 |
| Ic12-5 | NHCH$_2$CN | Ph | 6,8-Cl$_2$ | 204.7 |
| Ic12-6 | NHCH$_2$CO$_2$Me | Ph | 6,8-Cl$_2$ | 201.4 |
| Id3-1 | O(CH$_2$)$_2$NH$_2$ | Ph | 6-Cl | 134.9 |
| Ie3-1 | S(CH$_2$)$_2$OH | Ph | 6-Cl | 124.4 |
| Ie3-2 | S(CH$_2$)$_2$NH$_2$ | Ph | 6-Cl | 88.3 | a) The structure was described in Synthesis Example 11.

b) $^1$H NMR (CDCl$_3$): 1.66-1.75 (1H, m), 1.86-2.08 (3H, m), 3.57-3.64 (1H, m), 3.75-3.83 (2H, m), 3.89-3.59 (1H, m), 4.13-4.20 (1H, m), 5.70 (1H, br. s), 7.52-7.60 (5H, m), 7.64-7.69 (2H, m), 7.75-7.76 (1H, m).

c) $^1$H NMR (CDCl$_3$): 1.22 (3H, t, J=7.0 Hz), 3.55 (2H, q, J=7.0 Hz), 3.68 (2H, t, J=5.2 Hz), 3.78 (2H, q-like, J=5.2 Hz), 5.75 (1H, br. t), 7.53-7.60 (5H, m), 7.65-7.69 (2H, m), 7.75-7.77 (1H, m).

d) $^1$H NMR (CDCl$_3$): 1.22 (3H, t, J=7.0 Hz), 1.96 (2H, quintet, J=6.3 Hz), 3.50 (2H, q, J=7.0 Hz), 3.58 (2H, t, J=6.3 Hz), 3.67 (2H, q-like, J=6.3 Hz), 5.65 (1H, br. t), 7.53-7.60 (5H, m), 7.65-7.69 (2H, m), 7.74-7.76 (1H, m).

Reference Synthesis Example 1

Preparation of 8-chloro-4-phenyl-2(1H)-quinazolinone (compound No. II-11)

To 7.10 g of phenylmagnesium bromide (32% THF solution) was added dropwise a solution of 953 mg of 2-amino-3-chlorobenzonitrile in THF (7 ml) at room temperature, followed by heating under reflux for 30 minutes. To the resulting reaction product was added dropwise 885 mg of methyl chlorocarbonate under ice cooling, followed by heating under reflux for 40 minutes. The resulting reaction solution was cooled and poured into 40 ml of 2N-hydrochloric acid, and 8 g of sodium bicarbonate and 20 ml of MTBE were added thereto, followed by stirring. Precipitated crystals were collected by filtration to obtain 1.30 g of the titled compound. $^1$H NMR (DMSO-d$_6$): 7.24 (1H, t, J=8.0 Hz), 7.57-7.70 (6H, m), 7.90-7.93 (1H, m), 11.45 (br. s).

Reference Synthesis Example 2

4-phenyl-6-trifluoromethyl-2(1H)-quinazolinone (compound No. II-6)

To a solution of 762 mg of 2-amino-5-trifluoromethylbenzophenone in 10 ml of chloroform was added dropwise 349 mg of triethylamine, and then 627 mg of trichloroacetyl chloride was added dropwise under ice-cooling. After stirring at the same temperature for 30 minutes, 50 ml of water was added, thereby separating the solution. The organic layer was collected and then concentrated. The resulting residue was purified by silica gel column chromatography (hexane:ethyl acetate=5:1) to obtain 1.08 g of 2'-benzoyl-2,2,2-trichloro-4'-trifluoromethylacetanilide. $^1$H NMR (CDCl$_3$): 7.53-7.58 (2H, m), 7.66-7.75 (3H, m), 7.90-7.95 (2H, m), 8.81 (1H, d, J=8.6 Hz), 12.38 (1H, br. s).

A mixture of 1.08 g of 2'-benzoyl-2,2,2-trichloro-4'-trifluoromethylacetanilide, 10 ml of DMSO and 1.18 g of ammonium acetate was stirred at 75° C. for 1 hour. After cooling, 100 ml of water was added and precipitated crystals were collected by filtration. The resultant collected substance was dissolved in a mixture of hexane:ethyl acetate=1:1, dehydrated using anhydrous magnesium sulfate and then concentrated to obtain 765 mg of the titled compound. $^1$H NMR (CDCl$_3$): 7.58-7.68 (3H, m), 7.75 (1H, d, J=8.8 Hz), 7.79-7.83 (2H, m), 7.93 (1H, dd, J=8.8, 1.7 Hz), 8.17 (1H, br. s), 13.37 (1H, br. s).

Examples of compounds which can be prepared in the same manner as in Reference Synthesis Examples described above are shown in Table 7 (also including the compounds prepared in Reference Synthesis Examples described above).

Notes "a)" to "i)" in Table 7 are as follows.

TABLE 7

| Compound No. | Ar | (X)$_n$ | Melting point (° C.) |
|---|---|---|---|
| II-1 | Ph | 5-Cl | a) |
| II-2 | Ph | 6-F | b) |
| II-3 | Ph | 6-Cl | >300 |
| II-4 | Ph | 6-Br | c) |
| II-5 | Ph | 6-Me | 291.9 |
| II-6 | Ph | 6-CF$_3$ | d) |
| II-7 | Ph | 6-NO$_2$ | 280 (decomposition) |
| II-8 | Ph | 6-OMe | e) |
| II-9 | Ph | 6-CN | f) |
| II-10 | Ph | 7-Cl | g) |
| II-11 | Ph | 8-Cl | h) |
| II-12 | Ph | 6,8-Cl$_2$ | i) |
| II-13 | p-Cl-Ph | 6-Cl | 269.6 (decomposition) |
| II-14 | m-Cl-Ph | 6-Cl | 295 (decomposition) | a) $^1$H NMR (DMSO-d$_6$): 7.27 (1H, dd, J=7.7, 1.0 Hz), 7.38 (1H, dd, J=8.3, 1.1 Hz), 7.43-7.55 (5H, m), 7.69 (1H, t, J=8.1 Hz), 12.18 (1H, br. s).
b) $^1$H NMR (DMSO-d$_6$): 7.35 (1H, dd, J=9.2, 2.7 Hz), 7.43 (1H, dd, J=9.2, 4.8 Hz), 7.58-7.74 (6H, m), 12.05 (1H, br. s).
c) $^1$H NMR (DMSO-d$_6$): 7.35 (1H, d, J=9.2 Hz), 7.59-7.71 (6H, m), 7.91 (1H, dd, J=9.2, 2.2 Hz), 12.08 (1H, br. s).
d) $^1$H NMR described in Reference Synthesis Example 2
e) $^1$H NMR (CDCl$_3$): 3.78 (3H, s), 7.25-7.27 (1H, m), 7.36-7.40 (1H, m), 7.54-7.62 (4H, m), 7.81-7.85 (2H, m), 13.37 (1H, br. s).
f) $^1$H NMR (DMSO-d$_6$): 7.48 (1H, d, J=8.4 Hz), 7.60-7.68 (3H, m), 7.71-7.74 (2H, m), 8.05 (1H, s), 8.08-8.12 (1H, m), 12.36 (1H, br. s).
g) (not isolated and purified)
h) $^1$H NMR described in Reference Synthesis Example 1
i) $^1$H NMR (DMSO-d$_6$): 7.52-7.72 (6H, m), 8.10-8.12 (1H, m), 11.69 (1H, br. s).

Example 1

Construction of *Arabidopsis Thaliana* cDNA Phage Library for Cloning CER1

Seeds of *Arabidopsis thaliana*, Wassilewskija line was sterilized with 70% ethyl alcohol for one minute and then with 1.5% sodium hypochlorite for 10 minutes. The seeds were washed well with sterile water and then cultured in a GM medium (4.3 Murashige and Skoog's basal salt mixture, 1% sucrose, 10 ml of 5% MES-KOH (pH 5.7), 0.3% Phytage™ (SIGMA)) for 2 weeks to obtain 5 g of a plant. The plant was frozen in liquid nitrogen and then physically ground with a mortar. To the obtained ground product was added a mixture of 10 mg of extraction buffer (200 mM Tris-HCl (pH 8.5), 100 mM NaCl, 10 mM EDTA, 0.5% SDS, 14 mM β-mercaptoethanol) and 10 g of phenol. The mixture was stirred by a Voltex mixer. Then, 10 ml of chloroform was added to the mixture, followed by thorough stirring. Next, the obtained mixture was centrifuged at 10,000 rpm for 20 minutes, and an aqueous layer was collected. To the collected aqueous layer was added LiCl at a final concentration of 2M, followed by standing at −80° C. for 3 hours. The obtained frozen product was thawed and then centrifuged at 10,000 rpm for 20 minutes. A precipitate was collected. The collected precipitate was dissolved in 2 ml of TE (10 mM Tris-HCl (pH 8.0), 1 mM EDTA). After 0.2 ml of 3M sodium acetate (pH 5.2) and 5 ml ethanol were added to the solution, the mixture was centrifuged to collect RNA a precipitate. Next, RNA containing polyA was extracted from the collected precipitate (RNA) with Oligotex™ dT30super (manufactured by Roche Japan Co., Ltd.).

A phase cDNA library was constructed from the extracted RNA containing polyA by using ZAP-cDNASynthesis Kit (manufactured by Stratagene Co., Ltd.) according to the kit instruction. The titer of the constructed phage cDNA library was 500,000 PFU.

Example 2

Preparation of DNA Probe for CRE1

PCR reaction was performed by using a phage liquid (about 1,000,000 PFU) of the phage cDNA library prepared in Example 1 as a template and a DNA of SEQ ID NO:3 and a DNA of SEQ ID NO:4 as primers, using TAKARA LA Taq™ kit (manufactured by Takara Shuzo Co., Ltd.) to amplify a DNA. Details are described below.

A PCR reaction liquid was prepared by adding reaction compositions such as dNTP to 1,000,000 PFU of the phase and each 0.2 µM of primer DNAs according to the kit instruction. PCR was performed under the condition that after warm-keeping at 94° C. for 2 minutes, 40 cycles of at 94° C. for 30 seconds, at 55° C. for 30 seconds and at 68° C. for 5 minutes were run, to amplify the desired DNA fragment. Next, a probe labeled with $^{32}P$ was prepared by using the amplified DNA fragment as a template and using Megaprime DNA-labelling system kit (manufactured by Amersham Pharmacia). Here; a reaction liquid (25 µl) was prepared by adding 32PdCTP 2.0 MBq to 25 ng of the amplified DNA fragment and then adding reaction compositions specified by the kit thereto. Labelling reaction was performed at 37° C. for 10 minutes.

Example 3

Obtaining of Phage cDNA Clone Carrying CRE1 Gene

The desired DRE1 gene was cloned by plaque hybridization using the DNA probe prepared in Example 2. Details are described below.

Plaques were formed by using the cDNA phage library prepared in Example 1 according to the instructions of ZAP-cDNARSynthesis kit. DNAs were adsorbed on a nitrocellulose filter from the formed plaques, and then fixed onto the filter by an ultraviolet treatment. The filter thus prepared was kept at 65° C. in the presence of 6×SSC (0.9M NaCl, 0.09M sodium citrate), 5× Denhart solution (0.1% (w/v) Ficol 400, 0.1% (w/v) polyvinyl pyrrolidone, 0.1% BSA), 0.5% (w/v) SDS, and 100 µg/ml of denatured salmon sperm DNA or in a DIG EASY Hyb solution (Boehringer Mannheim Co., Ltd.) containing 100 µg/ml of denatured salmon sperm DNA, kept twice at room temperature for 15 minutes in the presence of 1×SSC (0.15M NaCl, 0.015M sodium citrate) and 0.5% SDS, and then kept at 68° C. for 30 minutes in the presence of 0.1×SSC (0.015M NaCl, 0.0015M sodium citrate) and 0.5% SDS to obtain a hybridized phage cDNA clone.

Example 4

Cloning of CRE1 cDNA

PCR reaction was performed by using cDNA of the phage cDNA clone obtained in Example 3 as a template and using a DNA of SEQ ID NO:5 and a DNA of SEQ ID NO:6 as primers to amplify a DNA having the nucleotide sequence of SEQ ID NO:5. Details are described below.

The PCR reaction was performed by using Herculase Enhanced DNA Polymerase (manufactured by TOYOBO Co., Ltd.) under the amplification condition that after warm-keeping at 94° C. for 1 minute, 25 cycles of at 94° C. for 30 seconds, at 55° C. for 30 seconds and at 72° C. for 4 minutes were run. Here, a PCR reaction liquid (5.0 µl) was prepared by adding reaction compositions such as dNTP to 500 ng of cDNA of the phage cDNA clone and each 100 ng of primer DNAs according to the kit instruction.

As described above, the desired DNA fragment was amplified.

Example 5

Construction of CRE1 Expression Plasmid

A yeast expression vector, p415CYC (Munberg et al. Gene: 156 119-122 (1995), available from ATCC library (No. 87382)) was digested with the restriction enzyme Sma I. Then, the DNA fragment obtained in Example 4 (a DNA having the nucleotide sequence of SEQ ID NO:2) was connected to a CYC1 promoter sequence of the expression vector p415CYC1 by using T4 DNA Ligase, and thus incorporated so that the desired protein could be expressed in yeast. It was confirmed that the nucleotide sequence of the DNA fragment was inserted in the correct direction and was a nucleotide sequence of SEQ ID NO: 2 by using a sequencer. Thus, the expression plasmid p415CYC-CRE1 was obtained.

Example 6

Production of Transformed Cell TM182-CRE1 and Transformed Cell TM182-p415CYC1

Each of the expression plasmid p451CYC-CRE1 obtained in Example 5 and the yeast expression vector p415CYC was used to transform a Sln1-gene deficient strain, TM182 (sln1Δ) (Maeda T et al. Nature: 369 242-245 (1994)). The transformation was performed by using a Polyethylene glycol/lithium acetate (PEG/LiAc)-mediated transformation method according to VII. Library Transformation & Screening Protocols described in CLONTECH Co., Ltd.: MATCHMAKER Two-Hybrid System 3 User Manual, page 22. Since a nutritional requirement of leucine disappears in the obtained transformed cell, transformed yeasts capable of growing in a DOLU+Gal medium were selected to obtain the transformed cell TM182-CRE1 and the transformed cell TM182-p415CYC1.

Example 7

Method for Searching Chemical Substance Capable of Inhibiting Intracellular Signaling from Plant-derived Cytokinin Receptor of Cell The transformed cell TM182-CRE1 and the transformed cell TM182-p415CYC1 obtained in Example 6 were each inoculated in 10 ml of a DOLU+Gal medium, and preincubated at 30° C. for 18 hours to obtain a preincubation liquid for each of the transformed cells. The preincubation liquid was diluted with a DOLU+Glu medium for the transformed cell TM182-CRE1 or with a DOLU+Gal medium for the transformed cell TM182-p415CYC1 until OD600=0.1 was reached, to obtain a preincubation dilution for each of the transformed cells.

To each well of a 96-well plate was added 1 µl of a 200 ppm solution of a test substance in dimethyl sulfoxide (DMSO) to prepare an Assay plate. At the same time, as controls, only 1 µl of DMSO was added to a part of wells. An assay plate for the transformed cell TM182-CRE1 and an assay plate for the transformed cell TM182-p415CYC1 were prepared.

A 10,000 ppm solution of trans-zeatin (cytokinin) in DMSO was 50-fold diluted with a DOLU+Gul medium to 200 ppm. The 200 ppm trans-zeatin solution was added in an amount of 3/1,000 volume to each of the above-described preincubation dilution to prepare each preincubation dilution containing trans-zeatin at 0.6 ppm. The 0.6 ppm preincubation dilution was added in an amount of 100 µl to each wells of the assay plate for each transformed cell. The plates were incubated at 30° C. for 24 hours. Then, turbidity (OD 600) of each well was measured by using a plate reader. The activity of the test substance for inhibiting intracellular signaling from a plant-derived cytokinin receptor of a cell was tested by comparing the measured turbidity with the turbidity of the control well. Results are shown in Tables 8 and 9.

For the transformed cell TM182-CRE1, a test substance which had a lower turbidity than the turbidity of the control well was selected as a chemical substance capable of inhibiting intracellular signaling from a plant-derived cytokinin receptor of a cell. For the transformed cell TM182-p415CYC1, however, a test substance which had a lower turbidity than the turbidity of the control well in which the degree of lowering is equivalent to or more than that in the case of the transformed cell TM182-CRE1 was toxic to yeast, and therefore was not selected as a chemical substance capable of inhibiting intracellular signaling from a plant-derived cytokinin receptor of a cell.

(Relative growth rate in test section to control section)
 [%]=[(Turbidity in test section)−(Turbidity in blank)]/[(Turbidity in control section)−(Turbidity in blank)]×100

(Activity of inhibiting intracellular signaling from plant-derived cytokinin receptor of cell)
 [%]=100−(Relative growth rate in test section to control section)

TABLE 8

| Chemical substance (compound No.) | Relative growth rate (%) in test section of test substance to control section | | Activity (%) of test substance for inhibiting intracellular signaling from plant-derived cytokinin receptor of cell |
|---|---|---|---|
| | Transformed cell TM182-CRE1 | Transformed cell TM182-p415CYC1 | |
| Ia1-3 | 5.5 | 113.9 | 94.5 |
| Ia1-7 | 1.2 | 78.8 | 98.8 |
| Ib4-1 | 8.7 | 110.9 | 91.3 |
| Ic11-1 | 2.2 | 114.5 | 97.8 |
| Ic12-1 | 2.8 | 106.3 | 97.2 |
| Ic2-1 | 2.8 | 124.6 | 97.2 |
| Ic3-1 | 5.4 | 114.1 | 94.6 |
| Ic3-3 | 1.4 | 108.6 | 98.6 |
| Ic3-4 | 1.4 | 106.4 | 98.6 |
| Ic3-5 | 3.5 | 115.4 | 96.5 |
| Ic3-6 | 2.8 | 114.6 | 97.2 |
| Ic3-7 | 2.8 | 104.1 | 97.2 |
| Ic3-9 | 1.5 | 122.0 | 98.5 |
| Ic3-11 | 3.9 | 84.6 | 96.1 |
| Ic3-12 | 5.6 | 90.9 | 94.4 |
| Ic3-16 | 3.2 | 97.0 | 96.8 |
| Ic3-18 | 4.0 | 105.3 | 96.0 |
| Ic3-19 | 2.4 | 102.7 | 97.6 |
| Ic3-20 | 5.0 | 86.5 | 95.0 |
| Ic3-21 | 5.0 | 121.6 | 95.0 |
| Ic3-22 | 4.9 | 110.6 | 95.1 |
| Ic3-23 | 4.1 | 108.1 | 95.9 |
| Ic3-24 | 2.1 | 112.5 | 97.9 |
| Ic3-25 | 6.0 | 122.0 | 94.0 |
| Ic3-26 | 5.3 | 110.7 | 94.7 |
| Ic3-27 | 2.3 | 107.4 | 97.7 |
| Ic3-29 | 1.6 | 92.7 | 98.4 |

In all cases, the existing concentration of trans-zeatin was adjusted to 0.6 ppm and the existing concentration of a chemical substance was adjusted to 2 ppm.

TABLE 9

| Chemical substance (compound No.) | Relative growth rate (%) in test section of test substance to control section | | Activity (%) of test substance for inhibiting intracellular signaling from plant-derived cytokinin receptor of cell |
|---|---|---|---|
| | Transformed cell TM182-CRE1 | Transformed cell TM182-p415CYC1 | |
| Ic3-30 | 2.2 | 108.9 | 97.8 |
| Ic3-32 | 4.5 | 89.2 | 95.5 |
| Ic3-33 | 1.0 | 114.6 | 99.0 |
| Ic3-34 | 0.2 | 118.5 | 99.8 |
| Ic3-37 | 3.5 | 114.2 | 96.5 |
| Ic3-38 | 1.2 | 99.4 | 98.8 |
| Ic3-39 | −1.3 | 108.1 | 101.3 |
| Ic3-40 | 0.7 | 123.4 | 99.3 |
| Ic3-41 | 8.8 | 123.3 | 91.2 |
| Ic3-42 | −0.7 | 111.5 | 100.7 |
| Ic3-43 | 0.8 | 122.0 | 99.2 |
| Ic3-44 | 7.0 | 101.4 | 93.0 |
| Ic3-45 | 0.8 | 98.7 | 99.2 |
| Ic3-46 | 1.3 | 92.2 | 98.7 |
| Ic4-1 | 4.6 | 95.0 | 95.4 |
| Ic4-2 | 0.9 | 109.3 | 99.1 |
| Ic5-4 | 8.9 | 116.8 | 91.1 |
| Ic5-5 | 7.2 | 126.3 | 92.8 |
| Ic7-1 | 6.7 | 115.8 | 93.3 |
| Id3-1 | 2.1 | 112.5 | 97.9 |
| Ie3-1 | 2.3 | 110.7 | 97.7 |

In all cases, the existing concentration of trans-zeatin was adjusted to 0.6 ppm and the existing concentration of a chemical substance was adjusted to 2 ppm. ppm.

Example 8

Method for Testing Dose Response of Chemical Substance Capable of Inhibiting Intracellular Signaling from Plant-derived Cytokinin Receptor of Cell The chemical substances (which inhibit intracellular signaling from a plant-derived cytokinin receptor of a cell) selected in Example 7 was tested at varying test concentrations in the same manner as in Example 7. The transformed cell TM182-CRE1 and the transformed cell TM182-p415CYC1 obtained in Example 6 were incubated under the same conditions as in Example 7 except that the test concentrations of the chemical substances (which inhibit intracellular signaling from a plant-derived cytokinin receptor of a cell) selected in Example 7 were varied within the range of 0.06 ppm to 6 ppm. The concentration of the chemical substance tested was adjusted with DMSO. After completion of incubation, dose response for activity of inhibiting intracellular signaling from a plant-derived cytokinin receptor of a cell was examined from the minimum test concentration at which a proliferative state of the transformed cell TM182-CRE1 was not observed, or from a dose-response growth inhibition curve obtained by a method as described below.

For making a dose-response growth inhibition curve, first, a relative growth rate was calculated as follows.

(Relative growth rate) [%]=(B)/(A)×100

(A)=[(Turbidity in 0.06 ppm test section)−(Turbidity in blank)]/[(Turbidity in control section)−(Turbidity in blank)]

(B)=[(Turbidity in each test section)−(Turbidity in blank)]/[(Turbidity in control section)−(Turbidity in blank)]

Then, a graph in which the X axis showed the concentration of a test chemical substance and the Y axis showed a relative growth rate (see FIG. 1, left figures: transformed cell TM182-CRE1, right figures: transformed cell TM182-p415CYC1) was made to obtain a dose-response growth inhibition curve.

Example 9

Root Growth-Promoting Activity Test

Enshi standard medium having the following composition (see Table 10) was prepared. To cluster tubes was dispensed each 4 μl of a solution of a chemical substance in DMSO to a final concentration of 0.001 ppm to 10 ppm, and then, was dispensed each 600 μl of the sterilized Enshi standard medium. Then the resulting solution was well mixed. In each of the cluster tubes, 10-20 seeds of *Arabidopsis thaliana* were sown, and cultured at 22° C. for 10 days in the light. Then, the length of main roots (average main roots) generated from the seeds of *Arabidopsis thaliana* was measured. An average of eight repeats was determined, and a root growth rate was determined according to the following equation. As a result, a chemical substance which exhibited a significant root growth rate (for example, a root growth rate of 120% or more) could be judged to have a root growth-promoting activity.

As detailed results, final concentrations which exhibited the highest root growth rates were shown in Table 11 and Table 12.

Root growth rate (%)=(Average main root length in chemical substance-treated section)/(Average main root length in control section)×100

TABLE 10

| Composition | | Concentration (mg/L) |
|---|---|---|
| Calcium nitrate | $Ca(NO_3)_2 \cdot 4H_2O$ | 950 |
| Potassium nitrate | $KNO_3$ | 810 |
| Magnesium sulfate | $MgSO_4 \cdot 7H_2O$ | 500 |
| Ammonium phosphate | $NH_4H_2PO_4$ | 155 |
| Chelate iron | Fe-EDTA | 22.62 |
| Boric acid | $H_3BO_3$ | 2.86 |
| Manganese sulfate | $MnSO_4 \cdot 4H_2O$ | 1.81 |
| Zinc sulfate | $ZnSO_4 \cdot 7H_2O$ | 0.22 |
| Copper sulfate | $CuSO_4 \cdot 5H_2O$ | 0.08 |
| Sodium molybdate | $Na_2MoO_4 \cdot 2H_2O$ | 0.025 |

Adjusted to pH 5.8

TABLE 11

| Compound No. | Test final concentration (ppm) | Root growth-promoting activity |
|---|---|---|
| Ic3-3 | 5 | 163.4 |
| Ic3-4 | 0.625 | 129.5 |
| Ic3-5 | 0.625 | 134.0 |
| Ic3-6 | 0.625 | 122.4 |
| Ic3-7 | 1.25 | 142.5 |
| Ic3-8 | 1.25 | 136.4 |
| Ia1-3 | 5 | 137.5 |
| Ie3-1 | 5 | 120.9 |
| Ie3-2 | 10 | 147.6 |
| Ic3-10 | 10 | 120.6 |
| Ic3-11 | 1.25 | 128.2 |
| Ic3-12 | 1.25 | 128.9 |
| Ic3-13 | 10 | 140.5 |
| Ic3-14 | 2.5 | 126.2 |
| Ic3-15 | 5 | 131.0 |
| Ic3-16 | 5 | 155.3 |

TABLE 11-continued

| Compound No. | Test final concentration (ppm) | Root growth-promoting activity |
|---|---|---|
| Ic3-17 | 10 | 121.3 |
| Ic3-18 | 2.5 | 139.5 |
| Ic3-19 | 1.25 | 155.6 |
| Ic3-20 | 10 | 137.8 |
| Ic3-21 | 2.5 | 131.7 |
| Ic3-22 | 0.156 | 129.3 |
| Ic3-23 | 10 | 150.0 |
| Ic3-24 | 1.25 | 122.8 |
| Ic3-25 | 10 | 140.0 |
| Ic3-26 | 5 | 136.4 |
| Ic3-27 | 2.5 | 127.8 |
| Ic5-4 | 2.5 | 136.6 |
| Ic5-5 | 2.5 | 157.8 |
| Ic3-28 | 10 | 120.4 |
| Ic3-29 | 10 | 122.4 |
| Ic3-31 | 10 | 142.2 |
| Ic3-32 | 5 | 123.4 |
| Ic3-33 | 5 | 123.9 |

TABLE 12

| Compound No. | Test final concentration (ppm) | Root growth-promoting activity |
|---|---|---|
| Ic3-35 | 10 | 144.4 |
| Ic3-36 | 2.5 | 123.1 |
| Ia1-1 | 5 | 133.3 |
| Ia1-2 | 10 | 139.7 |
| Ic2-1 | 2.5 | 127.4 |
| Ic9-1 | 10 | 141.5 |
| Ic1-1 | 2.5 | 150.9 |
| Ic10-1 | 10 | 163.6 |
| Ic11-1 | 5 | 143.9 |
| Ic12-1 | 2.5 | 184.6 |
| Ic6-2 | 2.5 | 155.9 |
| Ia1-6 | 0.625 | 126.9 |
| Ic8-1 | 10 | 162.1 |
| Ic3-37 | 5 | 138.5 |
| Ic3-38 | 5 | 141.9 |
| Ic3-39 | 10 | 169.0 |
| Ic3-40 | 0.625 | 125.8 |
| Ic3-41 | 5 | 134.5 |
| Ic3-42 | 0.625 | 128.6 |
| Ic3-43 | 2.5 | 137.9 |
| Ic3-44 | 1.25 | 126.5 |
| Ic3-46 | 2.5 | 121.6 |
| Ic12-3 | 2.5 | 138.8 |
| Ia1-14 | 0.156 | 129.3 |
| II-5 | 10 | 124.4 |
| II-7 | 5 | 124.4 |
| II-14 | 2.5 | 126.1 |

Example 10

Evaluation Using Lettuce of Root Growth-promoting Activity of Substance Capable of Inhibiting Cytokinin Signaling With respect to the chemical substance Ic3-1 and the chemical substance Ic7-1 (which inhibit intracellular signaling from a plant-derived cytokinin receptor of a cell) selected in Example 7, a main root-growth promoting activity was evaluated using lettuce (*Lactuca sativa* Red wave). Aqueous solutions of the chemical substance having different concentrations (0.6 ppm, 1.2 ppm, 2.5 ppm, 5 ppm, 10 ppm, 20 ppm, each containing 0.1% DMSO) were prepared, and added in an amount of 1 ml onto a filter paper having a diameter of 50 mm in a 60ϕ plastic petri dish. Then, 30 lettuce seeds were sowed on the plastic petri dish. After culture in the light at 22° C. for 4 days, the length of a main root was measured. An average of 3 repeats was determined and a root growth rate was determined by the following equation.

Root growth rate (%)=(Average main root length in chemical substance-treated section)/(Average main root length in control section)×100−100

Figure 2:
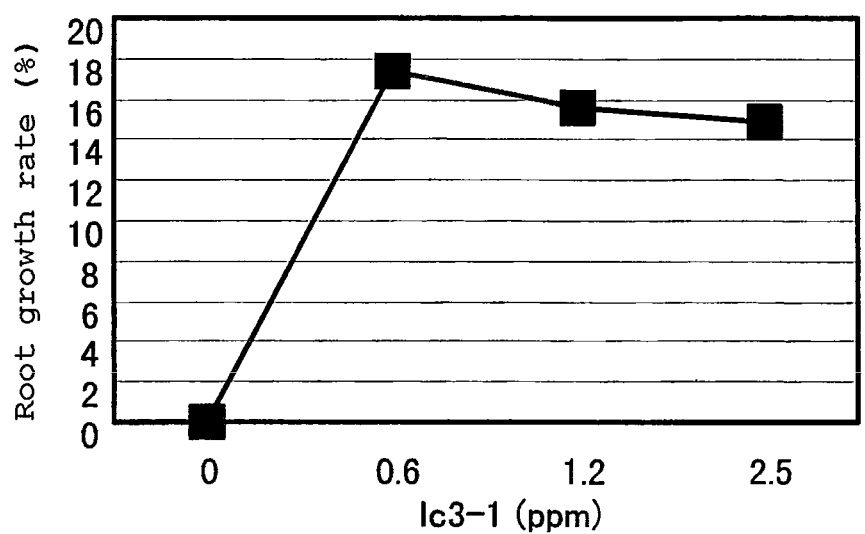
FIG. 2 shows results of evaluation of the root growth-promoting activity of a cytokinin signaling-inhibiting substance using lettuce in Example 10. In the figure, a data line represents a dose-response growth promotion curve, in which X axis represents the concentration of a tested chemical substance (chemical substance Ic3-1) and Y axis represents a root growth rate (%).
Figure 3:
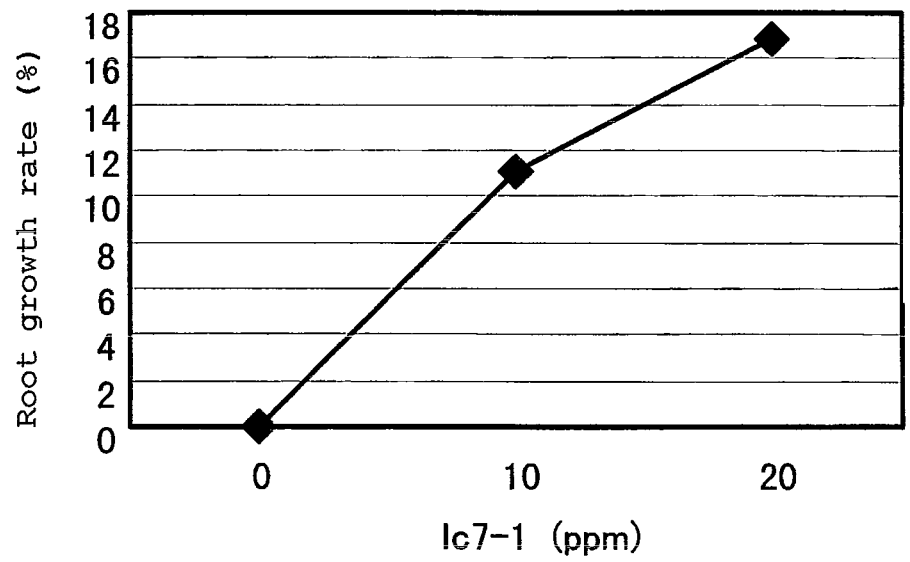
FIG. 3 shows results of evaluation of the root growth-promoting activity of a cytokinin signaling-inhibiting substance using lettuce in Example 10. In the figure, a data line represents a dose-response growth promotion curve, in which X axis represents the concentration of a tested chemical substance (chemical substance Ic7-1) and Y axis represents a root growth rate (%).

Results are shown in FIG. 2 and FIG. 3. In the case of the chemical substance Ic3-1, the main root growth at 0.6 ppm to 2.5 ppm was increased by 15 to 17% relative to the control section (see FIG. 2). In the case of the chemical substance Ic7-1, the main root extension at 10 ppm to 20 ppm was increased by 10 to 17% relative to the control section (see FIG. 3). Results of Dunnett's test showed that there was significant difference at a significant level of 5% in all treatment sections, and therefore, there was remarkable root growth promoting effect.

Example 11

Evaluation Using Rice of Root Growth-promoting Activity of Substance Capable of Inhibiting Cytokinin Signaling With respect to the chemical substance Ic3-1 and the chemical substance Ic7-1 (which inhibit intracellular signaling from a plant-derived cytokinin receptor of a cell) selected in Example 7, a main root-growth promoting activity was evaluated using rice (*Oriza sativa L. japonica*). Aqueous solutions of the chemical substance having different concentrations (10 ppm, 25 ppm, each containing 0.1% DMSO) were prepared. A naper towel was impregnated with 17 ml of the chemical solution, wherein the heavy paper was placed in a seed growth pouch for observation of root growth (177 mm×163 mm, manufactured by Daiki Rika Kogyo Co., Ltd.), and 3 rice seeds were sowed on the paper towel. The pouch was put in a plastic container, and then sealed. After culture in the light at 25° C. for 7 days, the length of a main root was measured. An average of 3 repeats was determined and a root growth rate was determined by the following equation.

Root growth rate (%)=(Average main root length in chemical substance-treated section)/(Average main root length in control section)×100−100

Figure 4:
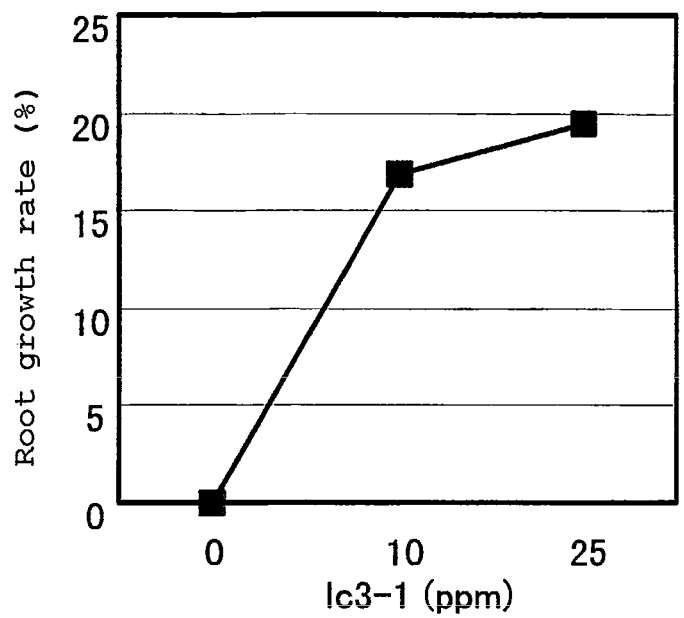
FIG. 4 shows results of evaluation of the root growth-promoting activity of a cytokinin signaling-inhibiting substance using rice in Example 11. In the figure, a data line represents a dose-response growth promotion curve, in which X axis represents the concentration of a tested chemical substance (chemical substance Ic3-1) and Y axis represents a root growth rate (%).
Figure 5:
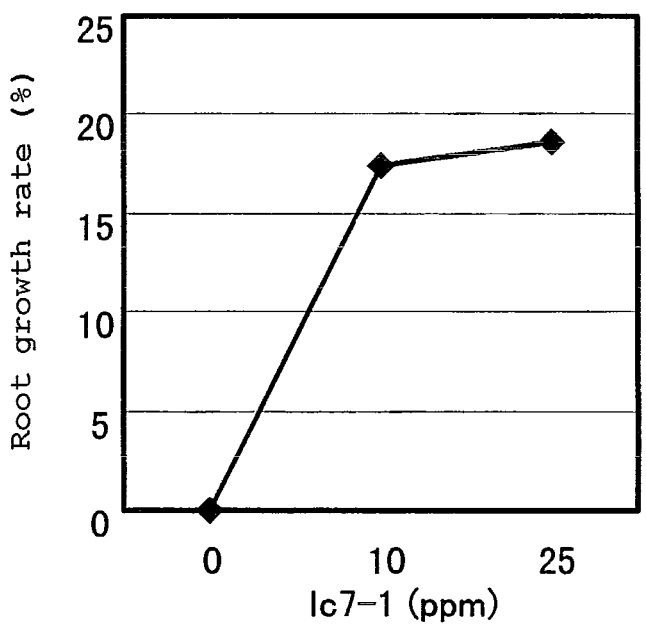
FIG. 5 shows results of evaluation of the root growth-promoting activity of a cytokinin signaling-inhibiting substance using rice in Example 11. In the figure, a data line represents a dose-response growth promotion curve, in which X axis represents the concentration of a tested chemical substance (chemical substance Ic7-1) and Y axis represents a root growth rate (%).

Results are shown in FIG. 4 and FIG. 5. In the case of the chemical substance Ic3-1, the main root growth at 10 ppm was increased by 17% and the main root growth at 25 ppm was increased by 20%, relative to the control section (see FIG. 4). In the case of the chemical substance Ic7-1, the main root growth at 10 ppm was increased by 17% and the main root growth at 25 ppm was increased by 19%, relative to the control section (see FIG. 5). Results of Dunnett's test showed that there was significant difference at a significant level of 5% in all treatment sections, and therefore, there was remarkable root growth promoting effect.

Example 12

Evaluation of Root Growth-promoting Activity of Substance Capable of Inhibiting Cytokinin Signaling by Rice Seed Treatment With respect to the chemical substance Ic3-1 and the chemical substance Ic7-1 (which inhibit intracellular signaling from a plant-derived cytokinin receptor of a cell) selected in Example 7, a main root-growth promoting activity induced by seed treatment was evaluated using rice (*Oriza sativa L. japonica*). The chemical substance was dissolved in acetone to prepare a 10,000 ppm solution. The acetone chemical substance solution (300 μl) thus prepared was put in an eppendorf tube. Then, 15 seeds were put in the eppendorf tube. The resulting mixture was mixed for about 30 seconds. The seeds thus chemical-treated were spread and dried on a filter paper.

Figure 6:
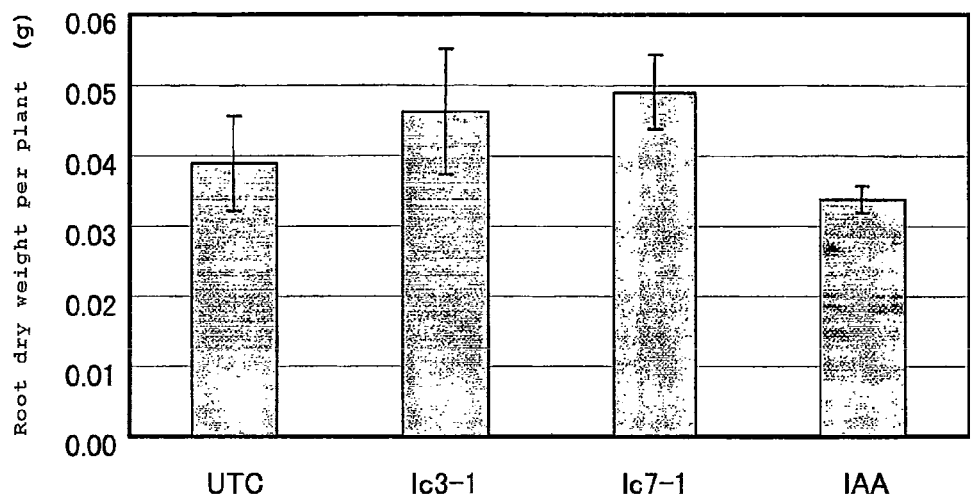
FIG. 6 shows results of evaluation of the root growth-promoting activity of a cytokinin signaling-inhibiting substance by rice seed treatment in Example 12. In the figure, "UTC" represents a result of a control test in which only acetone was used in the seed treatment. "IAA" represents a result of a test in which an auxin compound IAA was used.

About 820 ml of culture soil was placed in a plastic container (120 mm in length, 97 mm in height) with a hole in the bottom. The chemical-treated seeds were sowed in the plastic container (15 seeds per plastic container). The seeds were cultivated in a dark place at 30° C. for 4 days and then cultivated in a greenhouse for 35 days. Roots of the plant thus cultivated were removed and the soil adhered to the plant was washed away, followed by freeze-drying. Then, the weight of roots after freeze-drying was measured. A test was repeated 3 times for each treatment section, and an average was determined. Results are shown in FIG. 6.

In the case of the compound Ic3-1, the dry weight of roots per plant increased to 119% of the control section. In the case of the compound Ic7-1, the dry weight of roots per plant increased to 126% of the control section. In both cases, remarkable root growth promoting effect was found. In the case of an auxin compound IAA, the weight of roots was suppressed to 87% of the control section, and thus, root growth inhibiting effect was found.

Example 13

Evaluation of Plant Differentiation-promoting Activity of Substance Capable of Inhibiting Cytokinin Signaling, Using Hypocotyl of *Arabidopsis thaliana*

With respect to the chemical substance Ic3-1 and the chemical substance Ic7-1 (which inhibit intracellular signaling from a plant-derived cytokinin receptor of a cell) selected in Example 7, a plant differentiation-promoting activity was evaluated by examining an adventitious root formation activity using an hypocotyl of *Arabidopsis thaliana* Columbia.

First, an agar medium for sowing *Arabidopsis thaliana* was prepared. The agar medium contains, as components per 1 liter of an aqueous solution, 1 parcel of mixed salts for Murashige-Scoog plant medium (Wako Pure Chemical Industries, Ltd.) for 1 liter, 10 g of sucrose, 10 ml of an aqueous 5% MES (2-(N-Morpholino)ethanesulfonic acid) solution adjusted to pH 5.7 with potassium hydroxide, 100 mg of inositol, 1 ml of vitamins stock solution (10 g of thiamine hydrochloride, 1 g of pyridoxine hydrochloride, and 1 g of nicotinic acid per 1 liter of an aqueous solution) and 8 g of agar. Then, the agar medium was subjected to autoclave at 120° C. for 20 minutes, dispensed to circular petri dishes, and then solidified.

Seeds of *Arabidopsis thaliana* (about 25 μl) were put in a 1.5 ml tube. Thereto was added 1 ml of a 10-fold diluted solution of a sodium hypochlorite solution (Nacalai Tesque) with sterilized distilled water. The seed were sterilized while stirring for about 1 minute with a tube mixer (TOMY, MT-360, MIXING SPEED10). After the seeds were sedimented by a portable small-sized centrifuge, the diluted solution of the sodium hypochlorite solution was removed from the tube. After 1 ml of sterilized distilled water was newly added to the tube, the seeds were washed by stirring with the tube mixer for about 1 minute. The seeds were sedimented by a portable small-sized centrifuge, and then water after washing was removed from the tube. The washing operation was repeated 3 times. After completion of washing, the seeds were sown on the agar medium in the circular petri dish, and germinated and grown in a dark place at 22° C.

Separately, the chemical substance was dissolved in DMSO to prepare a 10,000 ppm solution. Furthermore, the solution was diluted with DMSO to prepare solutions of 6,000 ppm, 2,000 ppm, 600 ppm and 200 ppm. In each well of a 12-well multi-plate (SUMITOMO BAKELITE Co., Ltd.), 2 µl of the DMSO solution containing one kind of the chemical substance at one concentration was dispensed. In a well as control, 2 µl of DMSO was dispensed in place of the chemical substance DMSO solution. Then, trans-zeatin was dissolved in DMSO to prepare a 10,000 ppm solution. The solution was diluted with sterilized distilled water to prepare a 10 ppm solution. An agar medium having the above composition was prepared, autoclaved and then cooled to about 50° C. To this agar medium was added the 10 ppm trans-zeatin solution to a final concentration of 0.01 ppm, followed by mixing. The trans-zeatin-containing agar medium (2 ml each) was dispensed in each well of the 12-well multi-plate in which the chemical substance DMSO solution or DMSO has been dispensed, and then solidified.

Figure 7:
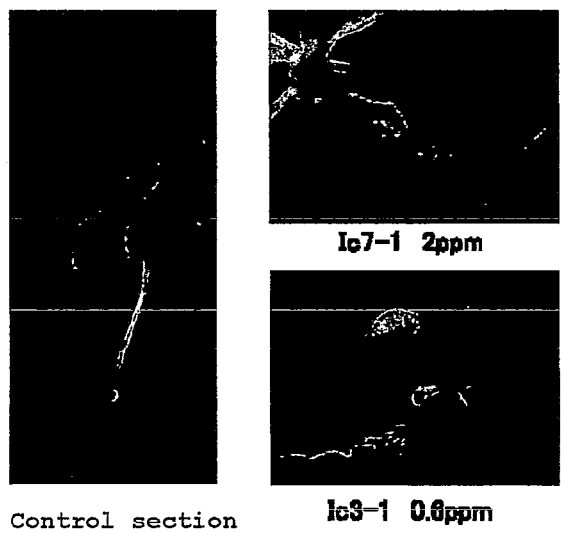
FIG. 7 shows results of measurement of the adventitious root formation activity of a cytokinin signaling-inhibiting substance using hypocotyl of A. thaliana for evaluating the plant differentiation-promoting activity in Example 13. In the figure, "control section" shows a result in a control test using an agar medium as described in Example 13.

A seedling of *Arabidopsis thaliana* after germination and growing in a dark place at 22° C. was cut at the hypocotyl portion, and the hypocotyl at the side with cotyledons was used for measurement of an adventitious root formation activity as described below. The hypocotyl at the side with roots was discarded. Specifically, the hypocotyl with cotyledons was inserted into the agar medium in each well of the 12-well multi-plate up to about 5 mm from the cut portion. The multi-plate was allowed to stand in the light at 22° C. for 16 hours (in the dark for 8 hours) As a result, adventitious roots were formed from the hypocotyl portion inserted into the agar medium containing the chemical substance Ic3-1 (in all test sections each having a final concentration of 6 ppm, 2 ppm, 0.6 ppm or 0.2 ppm) and the hypocotyl portion inserted into the agar medium containing the chemical substance Ic7-1 (in test sections each having a final concentration of 6 ppm or 2 ppm). In the control section in which DMSO was added in place of the chemical substance DMSO solution, formation of adventitious roots from the hypocotyl portion could not be found. Test results in the case of the embryonic axis inserted into the agar medium containing the chemical substance Ic3-1 having a final concentration of 0.6 ppm, the hypocotyl inserted into the agar medium containing the chemical substance Ic7-1 having a final concentration of 2 ppm, and the hypocotyl inserted into the agar medium of the control section are shown in FIG. 7.

Example 14

Measurement Using Rice of Root Growth-promoting Activity of Substance Capable of Inhibiting Cytokinin Signaling With respect to the chemical substance Ic3-3, a root growth promoting activity was measured using rice (*Oriza sativa japonica* Nipponbare).

Figure 8:
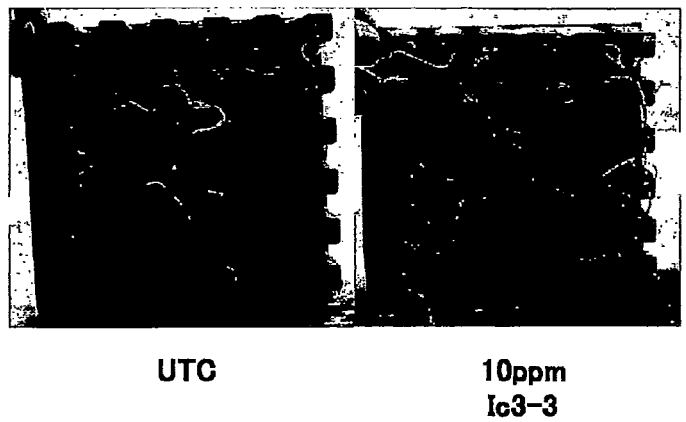
FIG. 8 shows results of measurement of the root growth-promoting activity of a cytokinin signaling-inhibiting substance using rice in Example 14. In the figure, "UTC" shows a result of a control test using only acetone in soil-drenching treatment.
Figure 9:
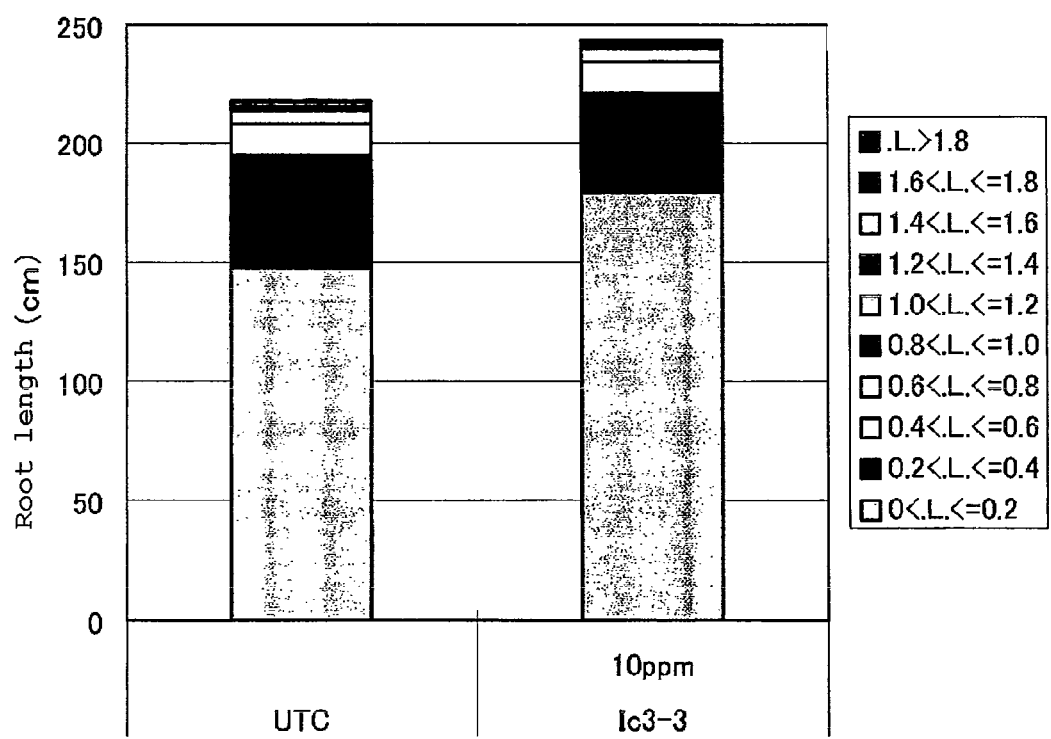
FIG. 9 shows analysis results of the root growth-promoting activity of a cytokinin signaling-inhibiting substance using rice by using an image analysis apparatus for measuring the root length in Example 14. Regarding data lines in the figure, X axis represents the concentration of a tested chemical substance (chemical substance Ic3-3) and Y axis represents the total sum (total root length) of the root lengths of each of root diameters. In the figure, "UTC" shows a result of a control test using only acetone in soil-drenching treatment. The legend value (L) represents a root diameter (mm).

First, an acetone solution containing a predetermined concentration of the chemical substance was prepared and then 100-fold diluted with distilled water to 10 ppm (containing 1% acetone) to obtain a chemical substance solution. Seeds were immersed in water for 2 days to stimulate germination. The seeds were sowed in a 288-well plug tray (3 seeds per well), and then soil was drenched with the above chemical substance solution in an amount of 500 µl per well. After covering with soil, the plug tray was put in a plastic bag and then placed in an air-conditioned room (dark place at 30° C.) for 3 days. After removing the plastic bag from the plug tray, the plug tray was placed under light conditions of light/dark=16 h/8 h for 4 days while the bottom was irrigated at all times. Thus, rice seeds were cultivated to obtain grown rice. The resulting rice roots were washed and the total root length was analyzed using a root length measurement image analyzer WinRHIZO (manufactured by Regent Instruments). In the chemical substance Ic3-3-treated section, root growth was remarkably promoted, as compared with the control section (UTC) in which only acetone was used in soil drenching treatment. A photograph is shown in FIG. 8. Analytical results obtained by the root length measurement image analyzer showed an increase of the total root length in the chemical substance Ic3-3-treated section. Results are shown in FIG. 9.

Example 15

Cloning of CRE1 cDNA, No. 2

PCR reaction was performed by using the expression plasmid p415CYC-CRE1 obtained in Example 5 as a template and using a DNA of SEQ ID NO: 7 and a DNA of SEQ ID NO: 8 as primers to amplify a DNA having the nucleotide sequence of SEQ ID NO: 2. Details are described below.

The PCR reaction was performed by using KOD Plus DNA Polymerase (manufactured by TOYOBO Co., Ltd.) under the amplification condition that after warm-keeping at 94° C. for 1 minute, 30 cycles of at 94° C. for 15 seconds, at 58° C. for 30 seconds and at 68° C. for 3 minutes and 30 seconds were run. Here, a PCR reaction liquid (50 µl) was prepared by adding reaction compositions such as dNTP to 500 ng of the plasmid p415CYC-CRE1 and each 100 ng of primer DNAs according to the kit instruction.

The desired DNA fragment thus amplified was cloned into a pCR-Blunt II-TOPO vector (Invitrogen Corporation) according to the instruction attached to the kit. In this case, the desired DNA fragment was inserted into the pCR-Blunt II-TOPO vector in the direction which enables the nucleotide sequence of SEQ ID NO: 7 to be close to a T7 promotor and the nucleotide sequence of SEQ ID NO: 8 to be close to a Sp6 promoter. It was confirmed that the nucleotide sequence of the DNA fragment was inserted in the correct direction and was a nucleotide sequence of SEQ ID NO: 2 by using a sequencer.

Example 16

Construction of CRE1 Expression Plasmid

A yeast expression vector, p425GPD (Munberg et al. Gene: 156 119-122 (1995), available from ATCC library (No. 87359)) was digested with the restriction enzyme BamHI. Then, the DNA fragment obtained in Example 15 (a DNA having the nucleotide sequence of SEQ ID NO:2) was connected to a GPD promoter sequence of the expression vector p425GPD by using T4 DNA Ligase, and thus incorporated so that the desired protein could be expressed in yeast. It was confirmed that the nucleotide sequence of the DNA fragment was inserted in the correct direction and was a nucleotide sequence of SEQ ID NO: 2 by using a sequencer. Thus, the expression plasmid p425GPD-CRE1 was obtained.

Example 17

Production of Transformed Cell TM182-p425GPD-CRE1

The expression plasmid obtained in Example 16 was used to transform a Sln1-gene deficient strain, TM182 (sln1Δ)

(Maeda T et al. Nature: 369 242-245 (1994)). The transformation was performed by using *S. cerevisiae* Direct Transformation Kit Wako (manufactured by Wako Pure Chemical Industries, Ltd.) according to the accompanying manual. Since a nutritional requirement of leucine disappears in the obtained transformed cell, a transformed yeast capable of growing in a DOLU+Gal medium was selected to obtain the transformed cell TM182-p425GPD-CRE1.

In the same manner, the transformed cell TM182-p425GPD was obtained by using the yeast expression vector p425GPD.

Example 18

Preparation of Membrane Protein Fraction Containing CRE1

The transformed cell TM182-p425GPD-CRE1 obtained in Example 17 was broken with glass beads and then supercentrifuged to prepare a membrane protein fraction containing CRE1. Details are described below.

The transformed cell TM182-p425GPD-CRE1 obtained in Example 17 was seeded in 100 ml of a DOLU+Gal medium and then incubated at 30° C. for 16 hours to obtain an incubation liquid having OD600=about 1.4. The incubation liquid was dispensed in a 50 ml centrifuge tube and then centrifuged at 4° C. and 7,400×g for 5 minutes to collect cells of the transformed cell TM182-p425GPD-CRE1. The resulting cells were suspended again in a phosphate buffer (prepared by mixing an aqueous 50 mM sodium dihydrogenphosphate solution with an aqueous 50 mM disodium hydrogenphosphate solution in a mixing ratio of 4:6 and adjusting to pH 7.0) cooled to 4° C., dispensed in a 2 ml tube and then centrifuged at 4° C. and 1,000×g for 5 minutes to collect cells of the transformed cell TM182-p425GPD-CRE1. The resulting cells were suspended again in the phosphate buffer cooled to 4° C. and then centrifuged at 4° C. and 1,000×g for 5 minutes to collect cells of the transformed cell TM182-p425GPD-CRE1. The resulting cells were suspended again in a phosphate buffer containing DTT (dithiothiothreitol) and PMSF (phenylmethylsulfonyl fluoride) (prepared by adding 5 mM DTT and 0.5 mM PMSF to the above-described phosphate buffer) in a 3-fold amount (based on cells). Then, 200 μl of the suspension was dispensed in a 1.5 ml tube containing 250 μl of glass beads (0.25 to 0.5 mm in diameter) previously cooled to 4° C. The 1.5 ml tube was stirred with a microtube mixer (MT-360 manufactured by TOMY) at the maximum output for 30 seconds and then cooled in ice for 1 minute, and this operation was repeated once again. Furthermore, the 1.5 ml tube was stirred with a multi-beads shocker (MB-200, Yasui Kikai Corporation) at an output (SPEED METER) of 2,000 for 30 seconds and then cooled in ice for 1 minute, and this operation was repeated further two times. Then, the 1.5 ml tube was centrifuged at 4° C. and 1,500×g for 10 minutes to collect a supernatant. The supernatant was transferred to a new 1.5 ml tube and centrifuged at 4° C. and 10,000×g for 3 minutes to collect a supernatant. The supernatant was centrifuged at 4° C. and 100,000×g for 1 hour using a supercentrifuge to collect a precipitate. The resulting precipitate was dissolved in a phosphate buffer containing 1% sucrose monocaprate (prepared by adding 1% sucrose monocaprate to the above-described phosphate buffer) to obtain a membrane protein fraction of the transformed cell TM182-p425GPD-CRE1.

In the same manner, a membrane protein fraction of the transformed cell TM182-p425GPD was prepared.

Example 19

Method for Examining Inhibition of Binding of Cytokinin to Cytokinin Receptor by Chemical Substance The membrane protein fraction of the transformed cell TM182-p425GPD-CRE1 obtained in Example 18 and cytokinin which was labeled with a radioisotope of hydrogen, tritium so as to become highly radioactive were used to examine that a test substance inhibited the binding of cytokinin to a cytokinin receptor. Details are described below.

As the cytokinin labeled with a radioisotope of hydrogen, tritium so as to become highly radioactive, [3H]N-6-(isopent-2-enyl)Adenine manufactured by Amersham Biosciences (hereinafter, referred to as radiolabel 2IP) was used. It had a specific radioactivity of 74.0 GBq/mmol and a radioactivity concentration of 37.0 MBq/ml.

Figure 10:
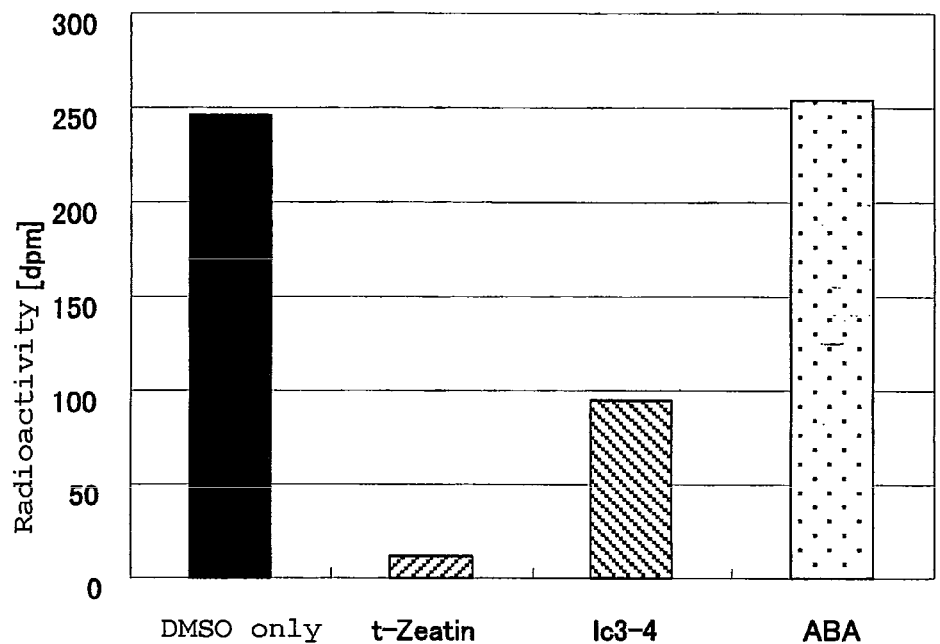
FIG. 10 shows results of an inhibition test of the binding of cytokinin to a cytokinin receptor by a test substance in Example 19. In the figure, "DMSO only" represents a control in which a test substance was not added and only DMSO, which was used as a solvent for a test substance, was added instead of a DMSO solution of a test substance. "t-Zeatin" represents addition of trans-zeatin as a test substance, "Ic3-4" represents addition of Ic3-4 as a test substance, and "ABA" represents addition of abscisic acid as a test substance. The concentration of the radioactive label 2IP is 10 nM, and the concentration of each test substance is 10 µM.
Figure 11:
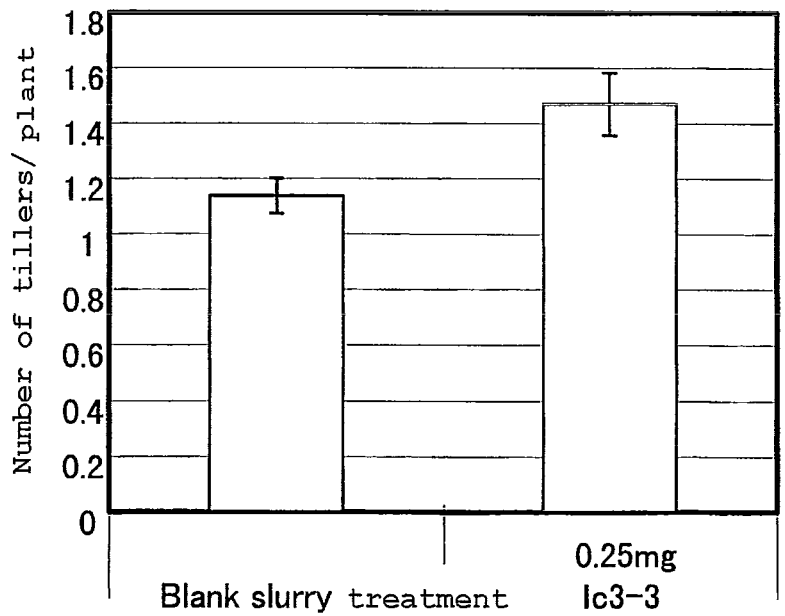
FIG. 11 shows evaluation results of the rice tillering-promoting activity of a cytokinin signaling-inhibiting substance in a test system in which seeds treatmented with the test substance were cultured by direct dry seeding in Example 21. In the figure, "Ic3-3" shows the number of tillers per plant in the case of using a Blank slurry solution of the test substance Ic3-3 for the seed treatment, and "Blank slurry treatment" shows the number of tillers per plant in the case of using a Blank slurry solution for the seed treatment instead of the Ic3-3 solution.

First, 100 μg of the membrane protein fraction of the transformed cell TM182-p415CYC1, a radiolabel 2IP dilution at a predetermined concentration with a phosphate buffer and 1 μl of a test substance dilution at a predetermined concentration with DMSO were mixed in a phosphate buffer to prepare 100 μl of a reaction liquid. Next, the reaction liquid was allowed to stand in ice for 1 hour and then filtered with a glass filter GF/B (manufactured by Whatman) to collect a membrane protein fraction of the transformed cell TM182-p425GPD-CRE1. The glass filter was immersed in a liquid scintillation cocktail Ultima Gold (manufactured by PerkinElmer Co., Ltd.), and radioactivity was measured by a liquid scintillation counter. For control, the same test was carried out using a membrane protein fraction of the transformed cell TM182-p425GPD. In order to eliminate influence of radioactivity due to nonspecific binding of the radiolabel 2IP, a value of radioactivity obtained in the test using the membrane protein fraction of the transformed cell TM182-p425GPD was subtracted from a value of radioactivity obtained in the test using the membrane protein fraction of the transformed cell TM182-p425GPD-CRE1. Test results are shown in FIG. 10.

In the case where the test substance was trans-zeatin or Ic3-4, the radioactivity was decreased as compared with the case where the test substance was not added (only DMSO which was used as a solvent of a test substance) or the test substance was abscisic acid.

Example 20

Evaluation of Rice Stand Establishment-promoting Activity of Substance Capable of Inhibiting Cytokinin Signaling by Seed Treatment in a Direct Seeding Test on Flooded Field Seeds of rice (*Oryza sativa japonica* Nipponbare) were treated with the chemical substance Ic3-1 (which inhibits intracellular signaling from a plant-derived cytokinin receptor of a cell) selected in Example 7, and were grown under direct seeding conditions. Then, a stand establishment rate was examined, and thus a rice stand establishment-promoting activity of the chemical substance was evaluated.

First, a Blank slurry solution containing 5% (v/v) Color Coat Red (manufactured by BECKER UNDERWOOD), 5% (v/v) CF-Clear (manufactured by BECKER UNDERWOOD) and 0.42% (v/v) Maxim-XL (manufactured by Syngenta) was prepared. In 1.3 ml of the Blank slurry solution, 6.25 mg, 12.5 mg, 25 mg or 50 mg of the chemical substance Ic3-3 was dissolved. Seeds were treated with the solution in an amount of 1.3 ml per 50 g of seeds (each corresponding to 0.125 mg, 0.25 mg, 0.5 mg and 1 mg/g seed) using a Hege11 seed treating device (manufactured by Hans-Ulrich Hege).

Then, a concrete pot (50 cm×50 cm) placed outdoors was flooded at a flooding depth of 5 cm, and 50 seeds per pot were sown. On day 23 after sowing, the number of seedlings whose leaf apex appeared on the water surface was examined. As a result, a stand establishment rate was increased at a seed treatment concentration of 0.125 to 1 mg/g seed, as compared with the Blank slurry-treated section. Test results (average) of each treatment section (four repeats) are shown in Table 13.

[Stand establishment rate (%)]=[Number of seedlings whose leaf apex appears on the water surface]/[Number of sown seeds]×100

TABLE 13

| Chemical substance | Amount of substance (mg/g seed) | Stand establishment rate (%) on day 23 after sowing |
| --- | --- | --- |
| Blank slurry |  | 76.7 |
| Ic3-3 | 0.125 | 87.3 |
|  | 0.25 | 82.7 |
|  | 0.5 | 79.3 |
|  | 1 | 84.0 |

Example 21

Evaluation of Rice Tillering-promoting Activity of Substance Capable of Inhibiting Cytokinin Signaling by Seed Treatment in a Direct Seeding Test on Dry Field Seeds of rice (*Oryza sativa japonica* Nipponbare) were treated with the chemical substance Ic3-1 (which inhibits intracellular signaling from a plant-derived cytokinin receptor of a cell) selected in Example 7, and were grown under direct seeding on dry field-conditions. Then, the number of tillers was examined, and thus a tillering-promoting activity of the chemical substance was evaluated.

First, a Blank slurry solution containing 5% (v/v) Color Coat Red (manufactured by BECKER UNDERWOOD), 5% (v/v) CF-Clear (manufactured by BECKER UNDERWOOD) and 0.42% (v/v) Maxim-XL (manufactured by Syngenta) was prepared. In 1.3 ml of the Blank slurry solution, 12.5 mg of the chemical substance Ic3-3 was dissolved. Seeds were treated with the solution in an amount of 1.3 ml per 50 g of seeds (corresponding to 0.25 mg/g seed) using a Hege11 seed treating device (manufactured by Hans-Ulrich Hege).

The, 20 seeds per pot of the treated seeds were sown in a 1/5000a Wagner pot at a depth of 1 cm and then cultured in a greenhouse. On day 10 after sowing, water was charged at a flooding depth of 5 cm and culture was continued. On day 30 after sowing, the number of tillers was examined. As a result, the number of tillers per stock was increased, as compared with the Blank slurry-treated section. Test results (average) of each treatment section (three repeats) are shown in Table 11.

Hereinafter, the compound (XI) used in the present invention will be described in more specifically by way of Synthesis Examples and Reference Synthesis Examples, but the compound (XI) is not limited to these examples.

In Synthesis Examples and Reference Synthesis Examples, "room temperature" usually means a temperature of 10 to 30° C. "$^1$H NMR" means a proton magnetic resonance spectrum. Using tetramethylsilane as an internal standard, the measurement was carried out with a spectrometer (400 MHz), Model JNM-AL400, manufactured by JEOL Ltd. and chemical shifts (δ) were expressed as ppm. "Mp" means a melting point and was measured with a melting point meter, Model Mettler FP61.

Abbreviations used in the following Synthesis Examples, Reference Synthesis Examples and Tables 2, 3, 4 and 5 have the following meanings. $CDCl_3$: deuterated chloroform, $DMSO-d_6$: deuterated dimethyl sulfoxide, s: singlet, d: doublet, t: triplet, q: quartet, dd: double doublet, m: multiplet, br: broad, J: coupling constant, Me: methyl, Et: ethyl, Pr: propyl, i-Pr: isopropyl, t-Bu: tertiary butyl, Ph: phenyl, Ac: acetyl, THF: tetrahydrofuran, DMF: N,N-dimethylformamide, DMSO: dimethyl sulfoxide and MTBE: methyl tertiary butyl ether Synthesis Example 12

Preparation of 2-amino-6,8-dichloro-4-phenylquinazoline (compound No. Ie-4)

A mixture of 300 mg of 2,6,8-trichloro-4-phenylquinazoline (compound No. II-5), 30 g of an aqueous 28% ammonia solution and 6 ml of acetonitrile was reacted in a pressure-resistant reaction vessel at 105° C. for 1.5 hours. The resulting reaction solution was cooled and then poured into 100 ml of water. The mixture was extracted with 60 ml of ethyl acetate and the resultant extract was concentrated. The resulting residue was purified by silica gel column chromatography (chloroform) to obtain 230 mg of the titled compound. Mp. 212.7° C. $^1$H NMR ($CDCl_3$): 5.56 (2H, br. s), 7.54-7.60 (3H, m), 7.63-7.68 (2H, m), 7.74 (1H, d, J=2.3 Hz), 7.79 (1H, d, J=2.3 Hz).

Synthesis Example 13

Preparation of 6-chloro-2-furfurylamino-4-phenylquinazoline (compound No. Ib-8)

A mixture of 275 mg of 2,6-dichloro-4-phenylquinazoline (compound No. II-2) and 486 mg of furfurylamine was stirred at 85° C. for 40 minutes and then poured into 50 ml of water. The mixture was extracted with ethyl acetate, and the resultant extract was washed with water and then concentrated. The resulting residue was recrystallized from ethanol to obtain 280 mg of the titled compound. Mp.142.0° C. $^1$H NMR ($CDCl_3$): 4.77 (2H, d, J=5.6 Hz), 5.70 (1H, br. t, J=5.6 Hz), 6.29-6.32 (2H, m), 7.36 (1H, dd, J=1.8, 0.9 Hz), 7.53-7.70 (7H, m), 7.78 (1H, d, J=2.2 Hz).

Synthesis Example 14

Preparation of 6-chloro-2-ethoxycarbonylmethylamino-4-phenylquinazoline (compound No. Ib-15)

To 550 mg of 2,6-dichloro-4-phenylquinazoline (compound No. II-2) and 419 mg of glycine ethyl ester hydrochloride were added 3 ml of DMF and 607 mg of triethylamine, followed by stirring at 85° C. for 5.5 hours. The resulting reaction solution was poured into 100 ml of water and extracted with ethyl acetate, and then the extract was concentrated. The resulting residue was purified by silica gel column chromatography (hexane:ethyl acetate=6:1 to 3:1) to obtain 503 mg of the titled compound. Mp.146.1° C. $^1$H NMR (CDCl$_3$): 1.30 (3H, t, J=7.2 Hz), 4.25 (2H, q, J=7.2 Hz), 4.31 (2H, d, J=5.2 Hz), 5.97 (1H, br. s), 7.54-7.63 (5H, m), 7.67-7.70 (2H, m), 7.79 (1H, s).

Synthesis Example 15

Preparation of 6-chloro-2-formamido-4-phenylquinazoline (compound No. Ib-17)

To a solution of 54 mg of dry formamide in DMF (5 ml) was added 48 mg of sodium hydride (60%), followed by stirring at room temperature for 30 minutes. To the reaction mixture was added 275 mg of 2,6-dichloro-4-phenylquinazoline (compound No. II-2), followed by warming to 85° C. and further stirring for 3 hours. The resulting reaction solution was poured into 100 ml of water and extracted with ethyl acetate, and then extract was concentrated. The resulting residue was purified by silica gel column chromatography (ethyl acetate:hexane=1:3) to obtain 64 mg of the titled compound. Mp. 252.1° C. $^1$H NMR: 7.59-7.66 (3H, m), 7.72-7.81 (3H, m), 7.88 (1H, d, J=8.8 Hz), 8.02 (1H, d, J=2.0 Hz), 8.37 (1H, br. d, J=10.4 Hz), 9.71 (1H, d, J=10.4 Hz).

Examples of compounds which can be prepared in the same manner as in Synthesis Examples described above are shown in Table 14 and Table 15 (also including the compounds prepared in Synthesis Examples described above). Notes "a)", "b)" and "c)" in Table 14 and Table 15 are as follows.

a) $^1$H NMR (CDCl$_3$): 1.66-1.75 (1H, m), 1.86-2.08 (3H, m), 3.57-3.64 (1H, m), 3.75-3.83 (2H, m), 3.89-3.59 (1H, m), 4.13-4.20 (1H, m), 5.70 (1H, br. s), 7.52-7.60 (5H, m), 7.64-7.69 (2H, m), 7.75-7.76 (1H, m).

b) $^1$H NMR (CDCl$_3$): 1.22 (3H, t, J=7.0 Hz), 3.55 (2H, q, J=7.0 Hz), 3.68 (2H, t, J=5.2 Hz), 3.78 (2H, q-like, J=5.2 Hz), 5.75 (1H, br. t), 7.53-7.60 (5H, m), 7.65-7.69 (2H, m), 7.75-7.77 (1H, m).

c) $^1$H NMR (CDCl$_3$): 1.22 (3H, t, J=7.0 Hz), 1.96 (2H, quintet, J=6.3 Hz), 3.50 (2H, q, J=7.0 Hz), 3.58 (2H, t, J=6.3 Hz), 3.67 (2H, q-like, J=6.3 Hz), 5.65 (1H, br. t), 7.53-7.60 (5H, m), 7.65-7.69 (2H, m), 7.74-7.76 (1H, m).

TABLE 14

| Compound No. | R$^{11}$ | m | X$_1$ | n | X$_2$ | Melting point (° C.) |
|---|---|---|---|---|---|---|
| Ia-1 | (CH$_2$)$_3$OH | 1 | 5-Cl | 0 | — | 175.7 |
| Ib-1 | (CH$_2$)$_4$OH | 0 | — | 1 | Cl | 115.6 |
| Ib-2 | (CH$_2$)$_5$OH | 0 | — | 1 | Cl | 117.2 |
| Ib-3 | (CH$_2$)$_2$OMe | 0 | — | 1 | Cl | 89.7 |
| Ib-4 | n-Pr | 0 | — | 1 | Cl | 158.3 |
| Ib-5 | (CH$_2$)$_2$CHMe$_2$ | 0 | — | 1 | Cl | 90.1 |
| Ib-6 | (CH$_2$)$_6$OH | 0 | — | 1 | Cl | 107.9 |
| Ib-7 | (CH$_2$)$_2$CH(Me)CH$_2$OH | 0 | — | 1 | Cl | 112.7 |
| Ib-8 | furfuryl | 0 | — | 1 | Cl | 142.0 |
| Ib-9 | CH$_2$CH=CMe$_2$ | 0 | — | 1 | Cl | 95.9 |
| Ib-10 | CH$_2$CH=C(Me)CH$_2$OH | 0 | — | 1 | Cl | 154.8 |
| Ib-11 | Et | 0 | — | 1 | Cl | 156.7 |
| Ib-12 | i-Pr | 0 | — | 1 | Cl | 112.5 |

TABLE 14-continued

| Compound No. | R$^{11}$ | m | X$_1$ | n | X$_2$ | Melting point (° C.) |
|---|---|---|---|---|---|---|
| Ib-13 | CH$_2$CH=CH$_2$ | 0 | — | 1 | Cl | 147.3 |
| Ib-14 | CH$_2$C≡CH | 0 | — | 1 | Cl | 168.4 |
| Ib-15 | CH$_2$CO$_2$Et | 0 | — | 1 | Cl | 146.1 |
| Ib-16 | CH$_2$CH$_2$CN | 0 | — | 1 | Cl | 198.7 |
| Ib-17 | CHO | 0 | — | 1 | Cl | 252.1 |
| Ib-18 | tetrahydrofurfuryl | 0 | — | 1 | Cl | syrup, a) |
| Ib-19 | (CH$_2$)$_3$OMe | 0 | — | 1 | Cl | 89.1 |
| Ib-20 | CH$_2$CH(OH)CH$_3$ | 0 | — | 1 | Cl | 154.2 |
| Ib-21 | (CH$_2$)$_2$O(CH$_2$)$_2$OH | 0 | — | 1 | Cl | 117.4 |
| Ib-22 | CH$_2$CH(OH)CH$_2$OH | 0 | — | 1 | Cl | 147.0 |
| Ib-23 | CH$_2$CO$_2$Me | 0 | — | 1 | Cl | 190.5 |
| Ib-24 | CH$_2$CH$_2$CO$_2$Me | 0 | — | 1 | Cl | 117.1 |
| Ib-25 | CH(Me)CH$_2$OH | 0 | — | 1 | Cl | 52.8 |
| Ib-26 | CH$_2$CH$_2$OEt | 0 | — | 1 | Cl | syrup, b) |
| Ib-27 | (CH$_2$)$_3$OEt | 0 | — | 1 | Cl | syrup, c) |

TABLE 15

| Compound No. | R$^{11}$ | m | X$_1$ | n | X$_2$ | Melting point (° C.) |
|---|---|---|---|---|---|---|
| Ic-1 | (CH$_2$)$_3$OH | 1 | 7-Cl | 0 | — | 129.7 |
| Id-1 | (CH$_2$)$_3$OH | 1 | 8-Cl | 0 | — | 115.5 |
| Ie-1 | (CH$_2$)$_3$OH | 1 | 8-Cl | 1 | Cl | 146.2 |
| Ie-2 | CH$_2$CH$_2$OH | 1 | 8-Cl | 1 | Cl | 168.8 |
| Ie-3 | furfuryl | 1 | 8-Cl | 1 | Cl | 158.6 |
| Ie-4 | H | 1 | 8-Cl | 1 | Cl | 212.7 |
| Ie-5 | CH$_2$CN | 1 | 8-Cl | 1 | Cl | 204.7 |
| Ie-6 | CH$_2$CO$_2$Me | 1 | 8-Cl | 1 | Cl | 201.4 |
| If-1 | (CH$_2$)$_3$OH | 0 | — | 1 | Br | 140.9 |
| If-2 | CH$_2$CO$_2$Me | 0 | — | 1 | Br | 183.1 (decomposition) |
| Ig-1 | H | 0 | — | 1 | CF$_3$ | 160.4 |
| Ig-2 | (CH$_2$)$_3$OH | 0 | — | 1 | CF$_3$ | 135.1 |
| Ih-1 | (CH$_2$)$_3$OH | 0 | — | 1 | CN | 173.3 (decomposition) |

Reference Synthesis Example 3

Preparation of 2,8-dichloro-4-phenylquinazoline (compound No. II-4)

To 1.24 g of 8-chloro-4-phenyl-2(1H)-quinazolinone (compound No. IV-4) was added 6.65 g of phosphorus oxychloride, followed by stirring at 95° C. for 1 hour. The resulting reaction solution was poured into 200 ml of ice water and sodium bicarbonate was added thereto, thereby adjusting the pH 9. Then, precipitated crystals were collected by filtration and recrystallized from ethanol to obtain 1.07 g of the titled compound. Mp.154.4.° C. $^1$H NMR (CDCl$_3$): 7.52-7.65 (4H, m), 7.76-7.80 (2H, m), 8.02-8.08 (2H, m).

Examples of compounds which can be prepared in the same manner as in Reference Synthesis Example 3 described above are shown in Table 16 (also including the compounds prepared in Reference Synthesis Example 3).

TABLE 16 structure: quinazoline with $(X_1)_m$ at positions 7,8; $(X_2)_n$ at positions 5,6; 2-Cl; 4-Ph

| Compound No. | m | $X_1$ | n | $X_2$ | Melting point (°C.) |
|---|---|---|---|---|---|
| II-1 | 1 | 5-Cl | 0 | — | 125.7 |
| II-2 | 0 | — | 1 | Cl | 166.2 |
| II-3 | 1 | 7-Cl | 0 | — | 115.4 |
| II-4 | 1 | 8-Cl | 0 | — | 154.4 |
| II-5 | 1 | 8-Cl | 1 | Cl | 160.3 |
| II-6 | 0 | — | 1 | Br | 185.1 (decomposition) |
| II-7 | 0 | — | 1 | $CF_3$ | 117.5 (decomposition) |
| II-8 | 0 | — | 1 | CN | 206.8 (decomposition) |

Reference Synthesis Example 4

Preparation of
8-chloro-4-phenyl-2(1H)-quinazolinone (compound No. IV-4)

To 7.10 g of phenylmagnesium bromide (32% THF solution) was added dropwise a solution of 953 mg of 2-amino-3-chlorobenzonitrile in THF (7 ml) at room temperature, followed by heating under reflux for 30 minutes. To the resulting reaction product was added dropwise 885 mg of methyl chlorocarbonate under ice cooling, followed by heating under reflux for 40 minutes. The resulting reaction solution was cooled and poured into 40 ml of 2N-hydrochloric acid, and 8 g of sodium bicarbonate and 20 ml of MTBE were added thereto, followed by stirring. Then, precipitated crystals were collected by filtration to obtain 1.30 g of the titled compound.
$^1$H NMR (DMSO-$d_6$): 7.24(1H, t, J=8.0 Hz), 7.57-7.70 (6H, m), 7.90-7.93 (1H, m), 11.45 (1H,br. s).

Reference Synthesis Example 5

Preparation of
4-phenyl-6-trifluoromethyl-2(1H)-quinazolinone (compound No. IV-7)

To a solution of 762 mg of 2-amino-5-trifluoromethylbenzophenone in 10 ml of chloroform was added dropwise 349 mg of triethylamine, and then 627 mg of trichloroacetyl chloride was added dropwise under ice cooling. After stirring at the same temperature for 30 minutes, 50 ml of water was added, thereby separating layers. The organic layer was collected and concentrated. The resulting residue was purified by silica gel column chromatography (hexane:ethyl acetate=5:1) to obtain 1.08 g of 2'-benzoyl-2,2,2-trichloro-4'-trifluoromethylacetanilide. $^1$H NMR (CDCl$_3$): 7.53-7.58 (2H, m), 7.66-7.75 (3H, m), 7.90-7.95 (2H, m), 8.81 (1H, d, J=8.6 Hz), 12.38 (1H, br. s).

A mixture of 1.08 g of 2'-benzoyl-2,2,2-trichloro-4'-trifluoromethylacetanilide, 10 ml of DMSO and 1.18 g of ammonium acetate was stirred at 75° C. for 1 hour. After cooling, 100 ml of water was added to the mixture. Precipitated crystals were collected by filtration. The collected substance was dissolved in a mixture of hexane:ethyl acetate=1:1, dehydrated using anhydrous magnesium sulfate, and then concentrated to obtain 765 mg of the titled compound. $^1$H NMR (CDCl$_3$): 7.58-7.68 (3H, m), 7.75 (1H, d, J=8.8 Hz), 7.79-7.83 (2H, m), 7.93 (1H, dd, J=8.8, 1.7 Hz), 8.17 (1H, br. s), 13.37 (1H, br. s).

Examples of compounds which can be prepared in the same manner as in Reference Synthesis Example 4 described above are shown in Table 17 (also including the compounds prepared in Reference Synthesis Example 4 described above). Notes "a)" to "g)" in Table 17 are as follows.
a) $^1$H NMR (DMSO-$d_6$): 7.27 (1H, dd, J=7.7, 1.0 Hz), 7.38 (1H, dd, J=8.3, 1.1 Hz), 7.43-7.55 (5H, m), 7.69 (1H, t, J=8.1 Hz), 12.18 (1H, br. s).
b) (not isolated and purified)
c) $^1$H NMR described in Reference Synthesis Example 4
d) $^1$H NMR (DMSO-$d_6$): 7.52-7.72 (6H, m), 8.10-8.12 (1H, m), 11.69 (1H, br. s).
e) $^1$H NMR (DMSO-$d_6$): 7.35 (1H, d, J=9.2 Hz), 7.59-7.71 (6H, m), 7.91 (1H, dd, J=9.2, 2.2 Hz), 12.08 (1H, br. s).
f) $^1$H NMR described in Reference Synthesis Example 5
g) $^1$H NMR (DMSO-$d_6$): 7.48 (1H, d, J=8.4 Hz), 7.60-7.68 (3H, m), 7.71-7.74 (2H, m), 8.05 (1H, s), 8.08-8.12 (1H, m), 12.36 (1H, br. s).

TABLE 17 structure: quinazolin-2(1H)-one with $(X_1)_m$ at positions 7,8; $(X_2)_n$ at positions 5,6; NH at 1; 2-oxo; 4-Ph

| Compound No. | m | $X_1$ | n | $X_2$ | Melting point (°C.) |
|---|---|---|---|---|---|
| IV-1 | 1 | 5-Cl | 0 | — | a) |
| IV-2 | 0 | — | 1 | Cl | >300 |
| IV-3 | 1 | 7-Cl | 0 | — | b) |
| IV-4 | 1 | 8-Cl | 0 | — | c) |
| IV-5 | 1 | 8-Cl | 1 | Cl | d) |
| IV-6 | 0 | — | 1 | Br | e) |
| IV-7 | 0 | — | 1 | $CF_3$ | f) |
| IV-8 | 0 | — | 1 | CN | g) |

Example 22

Root Growth-Promoting Activity Test

Enshi standard medium having the following composition (see Table 18) was prepared. To cluster tubes was dispensed each 4 µl of a solution of a chemical substance in DMSO to a final concentration of 0.001 ppm to 10 ppm, and then, was dispensed each 600 µl of the sterilized Enshi standard medium. Then the resulting solution was well mixed. In each of the cluster tubes, 10-20 seeds of *Arabidopsis thaliana* were sown, and cultured at 22° C. for 10 days in the light. Then, the length of main roots (average main roots) generated from the seeds of *Arabidopsis thaliana* was measured. An average of eight repeats was determined, and a root growth rate was determined according to the following equation. As a result, a chemical substance which exhibited a significant root growth rate (for example, a root growth rate of 120% or more) could be judged to have a root growth-promoting activity.

As detailed results, final concentrations which exhibited the highest root growth rates were shown in Table 19.

Root growth rate (%)=(Average main root length in chemical substance-treated section)/(Average main root length in control section)×100

Enshi standard medium determined having the following composition (Table 18) was prepared. A DMSO solution of a chemical substance was dispensed by 4 µl to cluster tubes to a final concentration of 0.001 ppm to 10 ppm and the sterilized Enshi standard medium was dispensed by 600 µl and then the resulting solution was well mixed. 10-20 seeds of *A. thaliana* per cluster tube were sown in the cluster tubes. After culture at 22° C. for 10 days in bright light, the length of main roots (average main roots) took from seeds of *A. thaliana* was measured. An average of eight repeats was determined and the root growth rate was determined. As a result, a chemical substance exhibited significant root growth rate (for example, the root growth rate is 120% or more) could be rated to be a chemical substance with root growth-promoting activity.

As detailed results, a value exhibited the highest root growth rate in the above final concentration was shown in Table 19.

Root growth rate (%)=(Average main root length of chemical substance-treated section)/(Average main root length of control section)×100

TABLE 18

| Composition | | Concentration (mg/L) |
|---|---|---|
| Calcium nitrate | $Ca(NO_3)_2 \cdot 4H_2O$ | 950 |
| Potassium nitrate | $KNO_3$ | 810 |
| Magnesium sulfate | $MgSO_4 \cdot 7H_2O$ | 500 |
| Ammonium phosphate | $NH_4H_2PO_4$ | 155 |
| Chelate iron | Fe-EDTA | 22.62 |
| Boric acid | $H_3BO_3$ | 2.86 |
| Manganese sulfate | $MnSO_4 \cdot 4H_2O$ | 1.81 |
| Zinc sulfate | $ZnSO_4 \cdot 7H_2O$ | 0.22 |
| Copper sulfate | $CuSO_4 \cdot 5H_2O$ | 0.08 |
| Sodium molybdate | $Na_2MoO_4 \cdot 2H_2O$ | 0.025 |

Adjusted to pH 5.8

TABLE 19

| Compound No. | Test final concentration (ppm) | Root growth-promoting activity |
|---|---|---|
| Ia-1 | 2.5 | 150.9 |
| Ib-1 | 0.625 | 129.5 |
| Ib-2 | 0.625 | 134.0 |
| Ib-3 | 1.25 | 142.5 |
| Ib-4 | 1.25 | 136.4 |
| Ib-5 | 10 | 120.6 |
| Ib-6 | 1.25 | 128.2 |
| Ib-7 | 1.25 | 128.9 |
| Ib-8 | 5 | 155.3 |
| Ib-9 | 10 | 121.3 |
| Ib-10 | 2.5 | 139.5 |
| Ib-11 | 1.25 | 122.8 |
| Ib-12 | 10 | 120.4 |
| Ib-13 | 10 | 122.4 |
| Ib-15 | 10 | 140.4 |
| Ib-17 | 2.5 | 134.0 |
| Ib-18 | 5 | 138.5 |
| Ib-19 | 5 | 141.9 |
| Ib-20 | 10 | 169.0 |
| Ib-21 | 0.625 | 125.8 |
| Ib-22 | 5 | 134.5 |
| Ib-23 | 0.625 | 128.6 |
| Ib-24 | 2.5 | 137.9 |
| Ib-25 | 1.25 | 126.5 |
| Ib-27 | 2.5 | 121.6 |
| Ic-1 | 10 | 163.6 |
| Id-1 | 5 | 143.9 |
| Ie-1 | 2.5 | 184.6 |
| Ie-3 | 2.5 | 138.8 |
| Ig-2 | 2.5 | 155.9 |
| Ih-1 | 10 | 141.5 |

Formulations of media used in the present invention are described below.

(a) DOLU+Glu medium
Bacto-yeast nitrogen base without amino acids 6.7 g
Glucose 20 g
SC-HIS-LEU-URA (Q-BIOgene) 1.66 g
Histidine 0.076 g
Distilled water 1000 ml (b) DOLU+Gal medium
Bacto-yeast nitrogen base without amino acids 6.7 g
Glucose 20 g
SC-HIS-LEU-URA (Q-BIOgene) 1.66 g
Histidine 0.076 g
Distilled water 1000 ml Industrial Applicability According to the present invention, it is possible to provide an agent capable of controlling the growth or differentiation of a plant, and a method for searching a chemical substance having a useful biological activity whose target has been made clear, that is, a method for screening a chemical substance using an activity on a specific target as an indicator so as to chemically control a target site.

Sequence Listing Free Text
SEQ ID NO: 3
Designed oligonucleotide primer for PCR
SEQ ID NO: 4
Designed oligonucleotide primer for PCR
SEQ ID NO: 5
Designed oligonucleotide primer for PCR
SEQ ID NO: 6
Designed oligonucleotide primer for PCR
SEQ ID NO: 7
Designed oligonucleotide primer for PCR
SEQ ID NO: 8
Designed oligonucleotide primer for PCR

The invention claimed is:

1. A plant growth regulating method comprising applying an effective amount of a compound represented by the general formula (I):

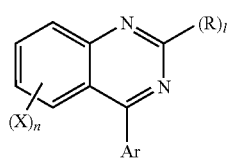

wherein R represents a group represented by NR$^1$R$^2$, and X represents an optionally substituted hydrocarbon group, a group represented by NR$^1$R$^2$, a group represented by OR$^3$, a group represented by S(O)$_m$R$^4$, a nitro group or a halogen atom, in which R$^1$ represents a hydrogen atom or an optionally substituted hydrocarbon group, R$^2$ represents a hydrogen atom, an optionally substituted hydrocarbon group, a group represented by NR$^5$R$^6$ (in which R$^5$ and R$^6$ are the same or different and represent a hydrogen atom or an optionally substituted C1-6 alkyl group) or a group represented by OR$^7$ (in which R$^7$ represents a hydrogen atom or an optionally substituted C1-6 alkyl group), or R$^1$ and R$^2$ are taken together with the nitrogen atom to which they are attached to form an optionally substituted cyclic amino group, R$^3$ and R$^4$ each represent an optionally substituted hydrocarbon group, l represents an integer of 0 to 1, m represents an integer of 0 to 2, n represents an integer of 0 to 4, when n is 2 or more, each X is the same or different from each other, and Ar represents a phenyl group which is optionally substituted by at least one halogen or C1-3 alkyl group or an agriculturally acceptable salt thereof to a plant or a habitat of the plant.

2. The plant growth regulating method according to claim 1, wherein the optionally substituted hydrocarbon group is a C1-3 alkyl group which is optionally substituted with (a) halogen atom(s) or (an) oxo group(s).

3. The plant growth regulating method according to claim 1, wherein l is 1.

4. The plant growth regulating method according to claim 1, wherein R$^1$ represents a hydrogen atom or a C1-3 alkyl group, R$^2$ represents a hydrogen atom, an amino group, a C1-3 alkylamino group, a di C1-3 alkylamino group, an amidino group, a C1-3 alkoxy group, a phenyl group, a C1-3 acyl group, a C1-6 alkyl group, a C3-6 alkenyl group or a C3-6 alkynyl group, in which the phenyl group is optionally substituted with 1 to 3 same or different C1-3 alkyl groups, the phenyl group, the acyl group, the alkyl group, the alkenyl group and the alkynyl group are optionally substituted with 1 to 3 same or different substituents selected from a halogen atom, a hydroxyl group, a C1-3 alkoxy group, a hydroxy C1-3 alkoxy group, a carboxyl group, a C1-3 alkoxycarbonyl group, a carbamoyl group, an amino group, a C1-3 alkylamino group, a di C1-3 alkylamino group, a mercapto group, a C1-3 acylthio group, a cyano group, a furyl group and a tetrahydrofuryl group, or R$^1$ and R$^2$ are taken together with the nitrogen atom to which they are attached to form a pyrrolidino group, a piperidino group or a morpholino group.

5. The plant growth regulating method according to claim 1, wherein R$^1$ represents a hydrogen atom, R$^2$ represents a hydrogen atom, a formyl group, a C1-6 alkyl group, a C3-6 alkenyl group or a C3-6 alkynyl group, in which the alkyl group, the alkenyl group and the alkynyl group are optionally substituted with (a) substituent(s) selected from a hydroxyl group, a methoxy group, a methoxycarbonyl group, an ethoxycarbonyl group, a cyano group and a furyl group.

6. The plant growth regulating method according to claim 1, wherein R$^3$ is a C1-3 alkyl group is optionally substituted with an amino group.

7. The plant growth regulating method according to claim 1, wherein R$^4$ is a C1-3 alkyl group which is optionally substituted with an amino group or a hydroxyl group, and m is 0.

8. The plant growth regulating method according to claim 1, wherein the halogen atom is a chlorine atom.

9. The plant growth regulating method according to claim 1, wherein n is from 1 to 2 and X is a C1-3 alkyl group, a C1-3 alkoxy group, a C1-3 haloalkyl group, a cyano group, a halogen atom or a nitro group.

10. The plant growth regulating method according to claim 1, wherein X is a chlorine atom, a bromine atom or a nitro group, and X is at the 6-position and/or the 8-position.

11. The plant growth regulating method according to claim 1, wherein Ar is a phenyl group which is optionally substituted with a halogen atom or a C1-3 alkyl group.

12. A compound represented by the formula (XI):

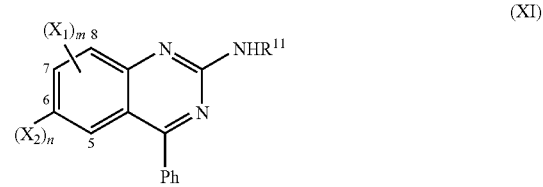

wherein Ph represents a phenyl group, R$^{11}$ represents a formyl group, a C1-6 alkyl group, a C3-6 alkenyl group or a C3-6 alkynyl group, in which the alkyl group, the alkenyl group and the alkynyl group are optionally substituted with at least one substituent selected from a hydroxyl group, a C1-3 alkoxy group, a C1-3 alkoxycarbonyl group, a cyano group, a 2-furyl group and a 2-tetrahydrofuryl group, m represents an integer of 0 to 3, n represents an integer of 0 to 1, at least one of m and n is not 0, X$_1$ and X$_2$ are the same or different and represent a chlorine atom, a bromine atom, a trifluoromethyl group, a cyano group or a nitro group, when m is 2 or more, each $X_1$ is the same or different from each other; provided that a) when m is 1, $X_1$ is a 5-chlorine atom or a 7-chlorine atom and $R^{11}$ represents a methyl group, n represents an integer of 1, or
b) when n is 1 and any one of conditions (1) to (3) is satisfied, m represents an integer of 1 to 3:
(1) $X_2$ is a chlorine atom, and $R^{11}$ is selected from the group consisting of a methyl group, a 2-hydroxyethyl group, a 3-hydroxypropyl group, a 2,2-dimethoxyethyl group and a cyanomethyl group,
(2) $X_2$ is a bromine atom, and $R^{11}$ is a group selected from a 2-hydroxyethyl group, a 3-hydroxypropyl group and a 2-methoxyethyl group, and
(3) $X_2$ is a nitro group, and $R^{11}$ is a 3-hydroxypropyl group; or an agriculturally acceptable salt thereof.

13. The compound according to claim 12, wherein $R^{11}$ represents a formyl group, a methyl group, an ethyl group, a 2-hydroxyethyl group, a 2-methoxyethyl group, a furfuryl group, a methoxycarbonylmethyl group or an ethoxycarbonylmethyl group, m is 0, n is 1, and $X_2$ is a chlorine atom or a nitro group, or an agriculturally acceptable salt thereof.

14. The compound according to claim 12, wherein $R^{11}$ represents a formyl group, a methyl group, an ethyl group, a 2-hydroxyethyl group, a 3-hydroxypropyl group, a 2-methoxyethyl group, a furfuryl group, a methoxycarbonylmethyl group or an ethoxycarbonylmethyl group, m is 1, n is 1, $X_1$ is an 8-chlorine atom, and $X_2$ represents a chlorine atom or a nitro group, or an agriculturally acceptable salt thereof.

15. The compound according to claim 12, wherein m is an integer of 1 to 3 and n is 0, or an agriculturally acceptable salt thereof.

16. The compound according to claim 12, wherein $R^{11}$ represents a formyl group, a C4-6 alkyl group, a C3-6 alkenyl group or a C3-6 alkynyl group in which the alkyl group, alkenyl group and alkynyl group are optionally substituted with (a) hydroxyl group(s) or (a) C1-3 alkoxy group(s), or $R^{11}$ represents a C1-3 alkoxycarbonylmethyl group, a C1-3 alkoxy C1-3 alkyl group or a furfuryl group, m is 0,
n is 1, and
$X_2$ is a chlorine atom, or an agriculturally acceptable salt thereof.

17. The compound according to claim 12, wherein n is 1, or an agriculturally acceptable salt thereof.

18. The compound according to claim 12, wherein m is 1 to 3 and n is 1, or an agriculturally acceptable salt thereof.

19. The compound according to claim 12, wherein $R^{11}$ is a C1-3 alkoxycarbonylmethyl group or a furfuryl group, or an agriculturally acceptable salt thereof.

20. The compound according to claim 12, wherein n is 1 and $X_2$ is a trifluoromethyl group or a cyano group.

* * * * *